(12) United States Patent
Nishiyama et al.

(10) Patent No.: US 8,328,712 B2
(45) Date of Patent: Dec. 11, 2012

(54) IMAGE PROCESSING SYSTEM, EXTERNAL DEVICE AND IMAGE PROCESSING METHOD

(75) Inventors: Takeshi Nishiyama, Akishima (JP); Katsuyoshi Taniguchi, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 267 days.

(21) Appl. No.: 12/886,856

(22) Filed: Sep. 21, 2010

(65) Prior Publication Data

US 2011/0218397 A1   Sep. 8, 2011

Related U.S. Application Data

(63) Continuation of application No. PCT/JP2009/070188, filed on Dec. 1, 2009.

(30) Foreign Application Priority Data

Mar. 23, 2009   (JP) .................................. 2009-070939

(51) Int. Cl.
   *A61B 1/04*   (2006.01)
(52) U.S. Cl. .......................... 600/109; 600/118; 600/113
(58) Field of Classification Search .................. 600/113, 600/160, 118, 109; 348/65, 74
   See application file for complete search history.

(56) References Cited

U.S. PATENT DOCUMENTS

| | | | |
|---|---|---|---|
| 6,939,292 B2 | 9/2005 | Mizuno | |
| 7,486,981 B2 | 2/2009 | Davidson | |
| 7,803,108 B2 | 9/2010 | Honda | |
| 8,194,096 B2* | 6/2012 | Hirakawa et al. | 345/619 |
| 2005/0043583 A1* | 2/2005 | Killmann et al. | 600/109 |
| 2006/0100486 A1* | 5/2006 | Maschke | 600/160 |
| 2006/0106318 A1* | 5/2006 | Davidson | 600/476 |
| 2006/0164511 A1* | 7/2006 | Krupnik | 348/65 |
| 2006/0217593 A1* | 9/2006 | Gilad et al. | 600/160 |
| 2007/0142710 A1* | 6/2007 | Yokoi et al. | 600/173 |
| 2007/0191683 A1 | 8/2007 | Fujimori | |
| 2007/0270642 A1* | 11/2007 | Bayer et al. | 600/109 |
| 2008/0039692 A1* | 2/2008 | Hirakawa | 600/160 |
| 2008/0242926 A1 | 10/2008 | Nishino | |
| 2008/0312504 A1* | 12/2008 | Kimoto | 600/118 |

(Continued)

FOREIGN PATENT DOCUMENTS

JP    10-02014    1/1998

(Continued)

OTHER PUBLICATIONS

International Search Report dated Jan. 26, 2010 received from the Japan Patent Office.

(Continued)

*Primary Examiner* — John P Leubecker
(74) *Attorney, Agent, or Firm* — Scully, Scott, Murphy & Presser, P.C.

(57) ABSTRACT

An image processing method includes the steps of: receiving image data from a body-insertable apparatus having a plurality of imaging units that captures an image of inside of a subject and generates image data and an identification information adding unit that adds identification information for identifying an imaging unit that generates the image data to the image data; displaying a list of the selected image data by the identification information; and switching image data to be displayed in the list displaying step from image data of the one identification information being displayed to image data of the other identification information.

27 Claims, 58 Drawing Sheets

U.S. PATENT DOCUMENTS

| | | |
|---|---|---|
| 2009/0003732 A1 | 1/2009 | Oda |
| 2009/0019381 A1 | 1/2009 | Kimoto |
| 2009/0022400 A1 | 1/2009 | Matsuzaki |
| 2009/0043155 A1 | 2/2009 | Fujimori |
| 2009/0043157 A1* | 2/2009 | Hirakawa et al. ............. 600/109 |
| 2010/0010304 A1* | 1/2010 | Kawano ........................ 600/117 |
| 2010/0016670 A1 | 1/2010 | Segawa et al. |
| 2010/0067808 A1 | 3/2010 | Matsuzaki |
| 2010/0182412 A1 | 7/2010 | Taniguchi et al. |
| 2011/0122146 A1* | 5/2011 | Nie et al. ...................... 345/589 |

FOREIGN PATENT DOCUMENTS

| | | |
|---|---|---|
| JP | 2003-070728 | 3/2003 |
| JP | 2006-142017 | 6/2006 |
| JP | 2006-288832 | 10/2006 |
| JP | 2006-301535 | 11/2006 |
| JP | 2007-075155 | 3/2007 |
| JP | 3898781 | 3/2007 |
| JP | 2007-130263 | 5/2007 |
| JP | 2007-282794 | 11/2007 |
| JP | 2008-006301 | 1/2008 |
| JP | 2008-22918 | 2/2008 |
| JP | 2008-173490 | 7/2008 |
| JP | 2008-237640 | 10/2008 |
| JP | 2008-246147 | 10/2008 |
| JP | 2009-005020 | 1/2009 |
| JP | 2009-005866 | 1/2009 |
| WO | WO 2006/109370 A1 | 10/2006 |
| WO | WO 2009/008125 A1 | 1/2009 |
| WO | WO 2009/013940 A1 | 1/2009 |

OTHER PUBLICATIONS

Japanese Official Action mailed Oct. 19, 2010, together with English-language translation.

* cited by examiner

FIG.25
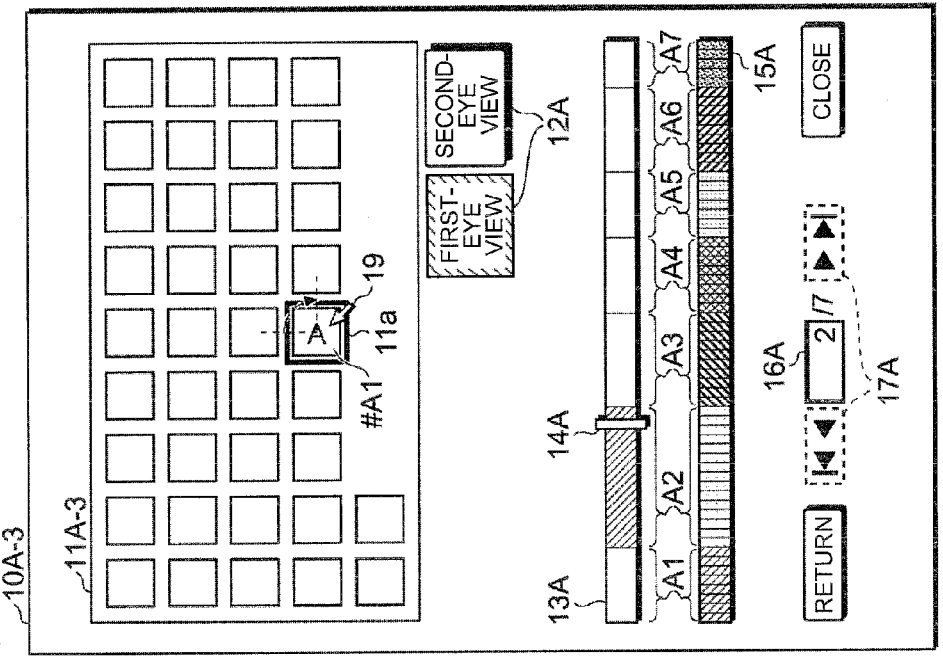
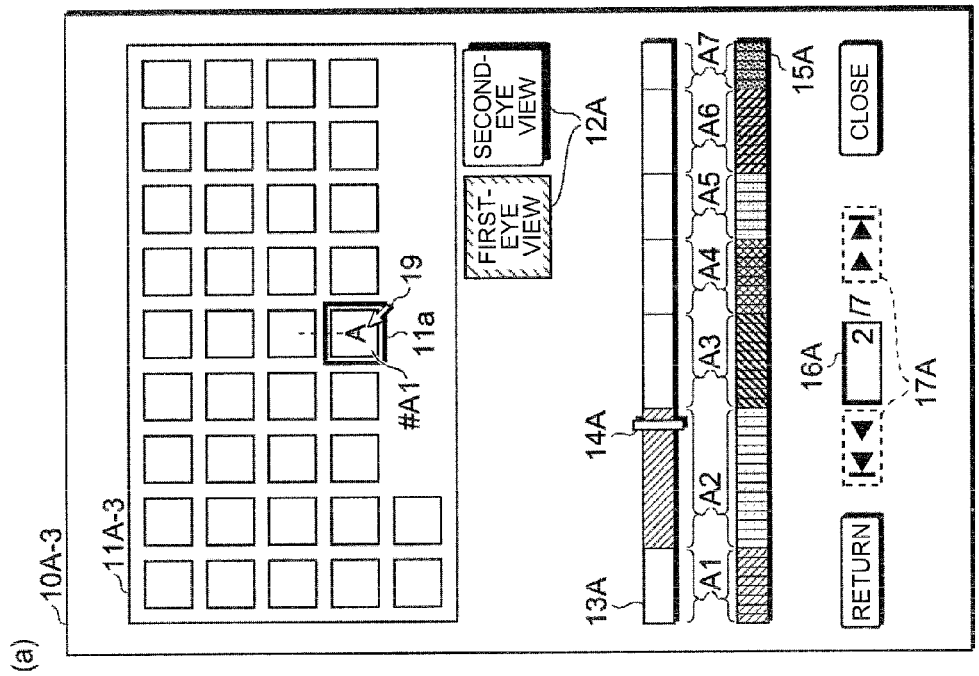

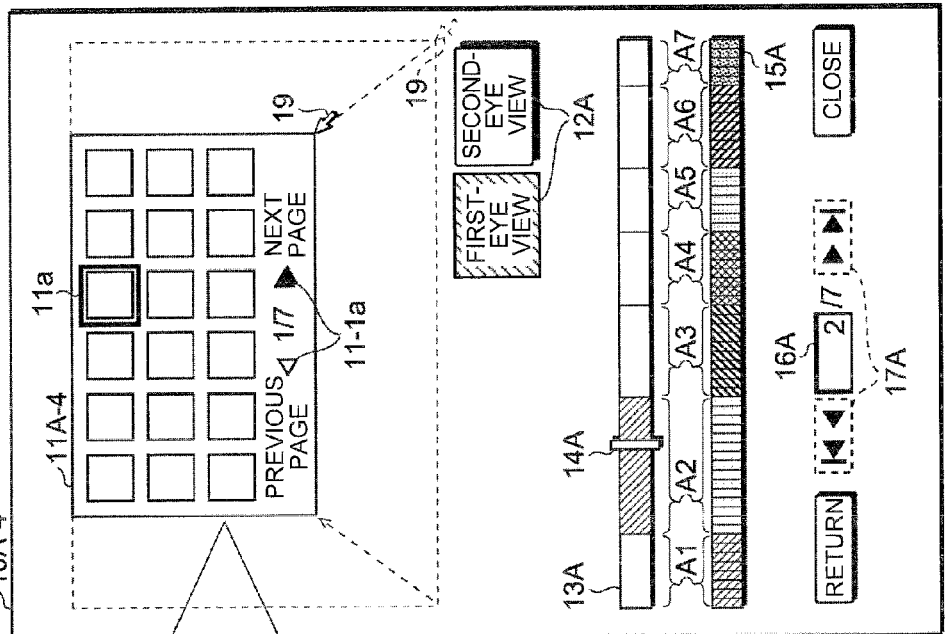
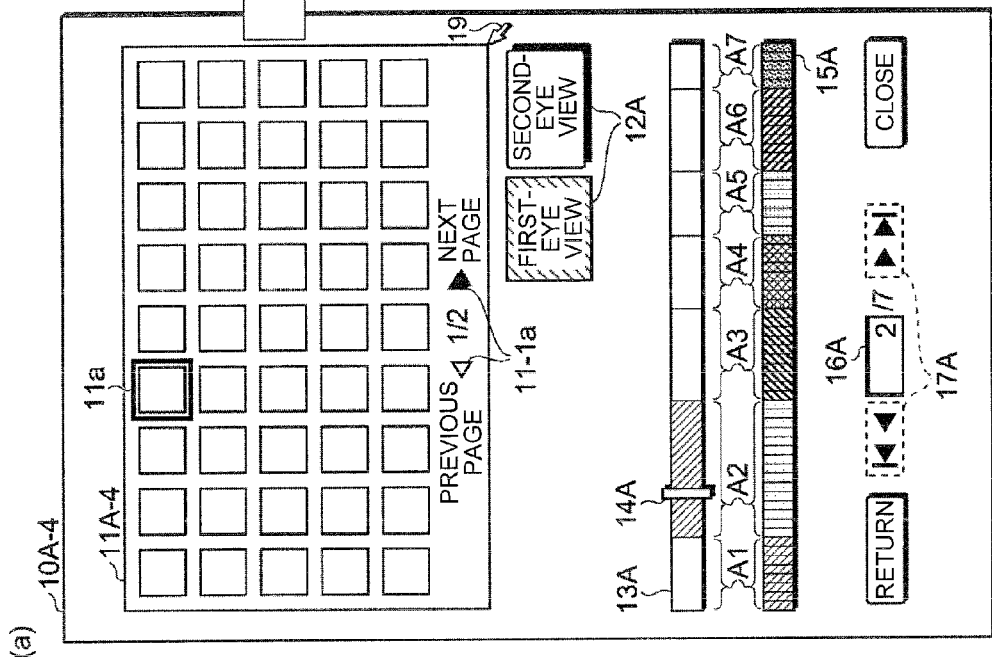
FIG.26

FIG. 41
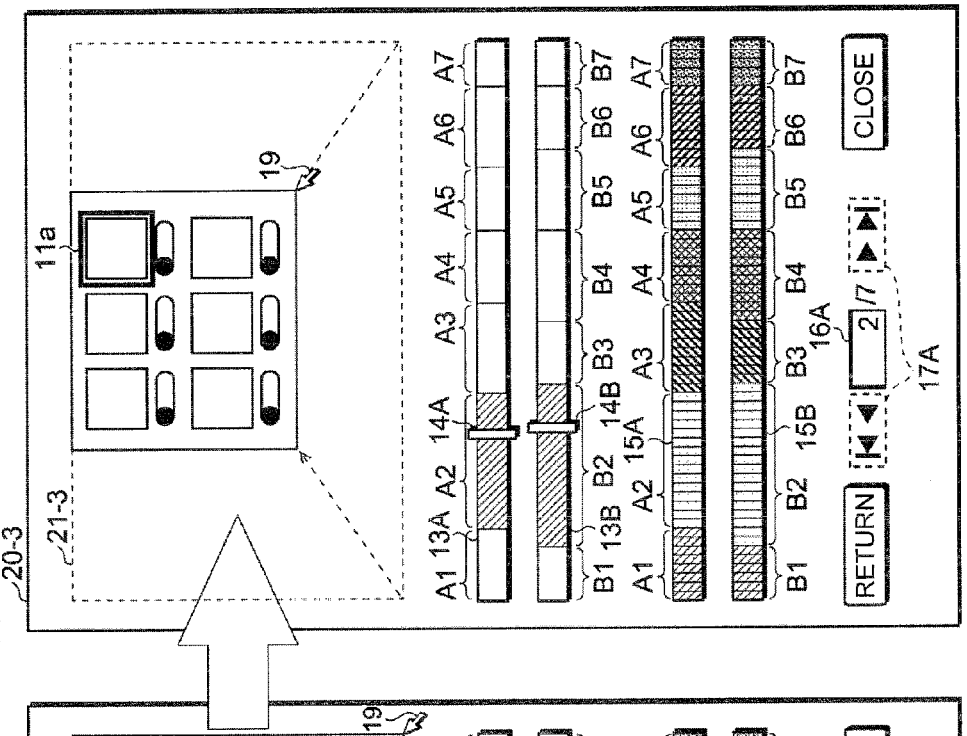
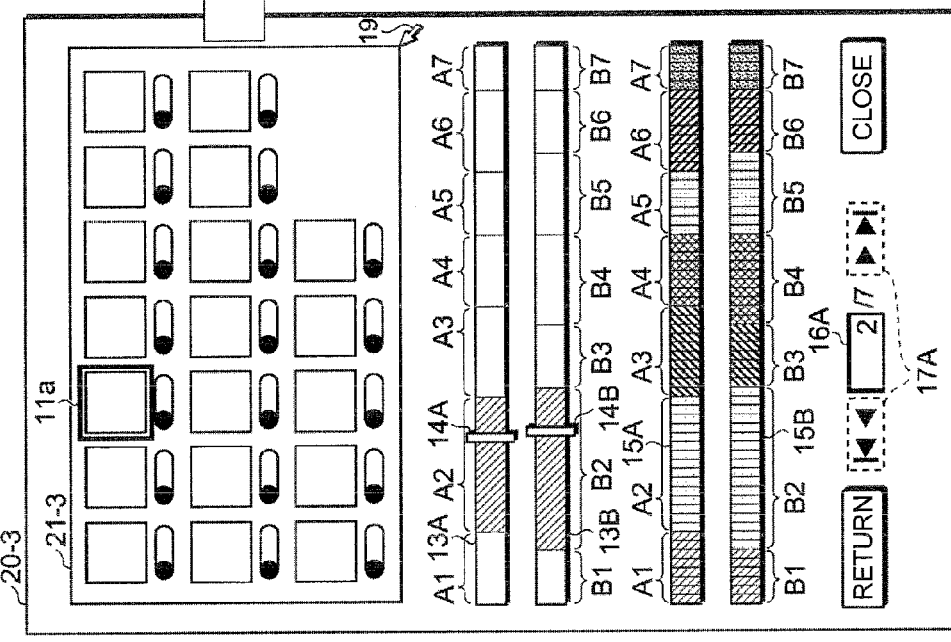

IMAGE PROCESSING SYSTEM, EXTERNAL DEVICE AND IMAGE PROCESSING METHOD

CROSS-REFERENCE TO RELATED APPLICATION

This application is a continuation of PCT international application Ser. No. PCT/JP2009/070188 filed on Dec. 1, 2009 which designates the United States, incorporated herein by reference.

BACKGROUND OF THE INVENTION

1. Field of the Invention

The present invention relates to an image processing system, an external device, and an image processing method.

2. Description of the Related Art

Devices for observing the inside of a subject such as a human being or an animal include a tube-type endoscope and a capsule endoscope (hereinbelow, simply called a body-insertable apparatus). The tube-type endoscope includes an electronic endoscope whose distal end is provided with a Charge Coupled Device (CCD) sensor and a fiber scope in which a bundle of optical fibers is inserted in a tube, and obtains images of the inside of a subject by inserting the tube from the mouse, the anus, or the like of a subject (refer to, for example, Japanese Patent No. 3,898,781). The body-insertable apparatus is small enough that a human, an animal, or the like can swallow it. For example, the body-insertable apparatus is introduced orally and periodically captures images of the inside of the subject. The images of the inside of the subject captured are transmitted as wireless signals to an external receiving device. The observer individually or continuously reproduced a plurality of images obtained by the tube-type endoscope or the body-insertable apparatus by a display device and diagnoses the inside of the subject by examining the images.

In recent years, a so-called multi-eye body-insertable apparatus having a plurality of (for example, two) imaging units is disclosed. With the multi-eye body-insertable apparatus, the inside of a subject can be imaged from many directions, so that more specific, accurate diagnosis can be realized (refer to, for example, Japanese Laid-open Patent Publication No. 2008-246147).

In recent years, to address a demand for improving the efficiency of diagnosis by image reading, there is proposed a medical system in which a display device is provided with a so-called overview function of reducing a plurality of pieces of image data obtained by a test and displaying a list of the reduced image data (refer to, for example, Japanese Laid-open Patent Publication No. 2007-75155).

SUMMARY OF THE INVENTION

An image processing system according to an aspect of the present invention includes a body-insertable apparatus that includes a plurality of imaging units that capture inside of a subject to generate image data, an identification information adding unit that adds identification information for identifying an imaging unit that generates image data to the image data, and an output unit that outputs the image data to which the identification information is added to the outside; and an external device that includes an input unit that receives the image data, a selecting unit that selects image data to be displayed on the basis of a result of image process on successive image data in a series of image data pieces of identification information, a list displaying unit that displays a list of the selected image data by the identification information, and a switching unit that switches image data to be displayed by the list displaying unit from image data of the identification information being displayed to image data of the other identification information.

An external device according to another aspect of the present invention includes an input means for receiving image data from a body-insertable apparatus that includes a plurality of imaging means for capturing an image of inside of a subject to generate image data, and an identification information adding means for adding identification information for identifying an imaging means that generates the image data to the image data; a selecting means for selecting image data to be displayed on the basis of a result of image process on successive image data in a series of image data pieces of one identification information; a list displaying means for displaying a list of the selected image data by the identification information; and a switching means for switching image data to be displayed by the list displaying means from image data of the one identification information being displayed to image data of the other identification information.

An image processing method according to still another aspect of the present invention includes receiving image data from a body-insertable apparatus that includes a plurality of imaging means for capturing an image of inside of a subject to generate image data and an identification information adding means for adding identification information for identifying an imaging means that generates the image data to the image data; selecting image data to be displayed on the basis of a result of image process on successive image data in a series of image data pieces of one identification information; displaying a list of the selected image data by the identification information; and switching image data to be displayed in the list from image data of the one identification information being displayed to image data of the other identification information.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 25 is a diagram showing an example of an overview screen according to modification 1-3 of the first embodiment of the invention;

FIG. 26 is a diagram showing an example of an overview screen according to the modification 1-4 of the first embodiment of the invention;

FIG. 41 is a diagram showing an example of an overview screen according to modification 2-3 of the second embodiment of the invention;

DETAILED DESCRIPTION OF THE PREFERRED EMBODIMENTS

Figure 1:
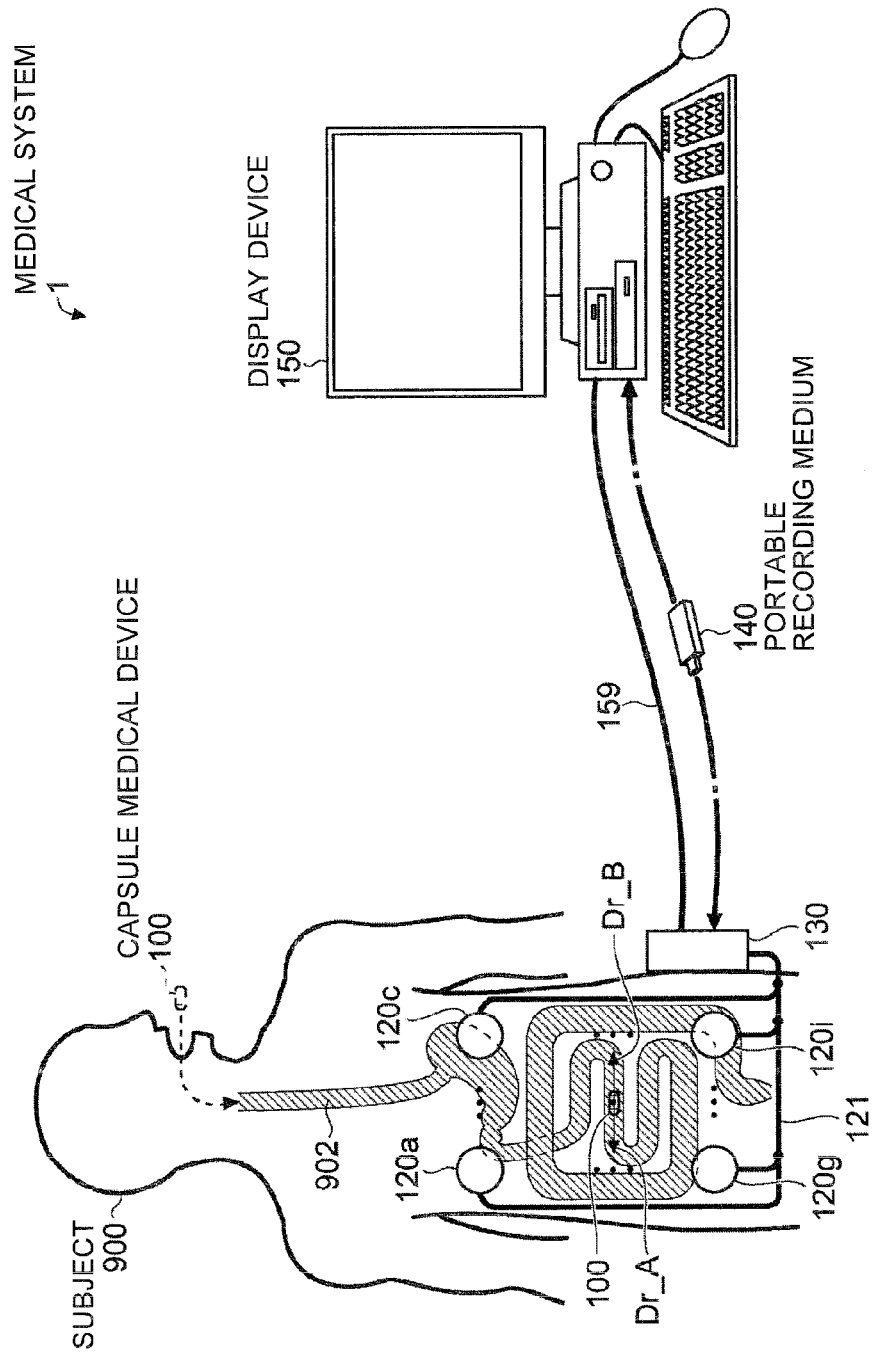
FIG. 1 is a schematic diagram showing a schematic configuration of a medical system according to a first embodiment of the present invention.

Best modes for carrying out the present invention will be described in detail below with reference to the drawings. In the following description, the drawings just schematically show shapes, sizes, and positional relations to a degree that the content of the present invention can be understood. Therefore, the present invention is not limited to the shapes, sizes, and positional relations shown in the drawings. In the drawings, to clearly show the configuration, a part of hatching in cross sections is omitted.

First Embodiment

In the following, the configuration and operation of a medical system 1 as an image processing system according to a first embodiment of the invention will be described in detail below with reference to the drawings. In the first embodiment, the case of using a capsule body-insertable apparatus (hereinbelow, called capsule medical device) 100 introduced in a subject 900 orally and capturing images of the inside of the subject 900 by executing imaging operation while traveling in a lumen 902 (refer to FIG. 1) from the stomach to the anus of the subject 900 will be described as an example. The invention, however, is not limited to the case but can be variously modified to, for example, the case of using a capsule medical device floating in liquid stored in a stomach, small intestine, large intestine, or the like of the subject 900.

Configuration

FIG. 1 is a schematic diagram showing a schematic configuration of the medial system 1 according to the first embodiment. As illustrated in FIG. 1, the medical system 1 has the capsule medical device 100 introduced in the subject 900, for example, via the oral route, a receiving device 130 for transmitting/receiving image data, a control instruction, and the like to/from the capsule medical device 100 by performing wireless communication with the capsule medical device 100, and a display device 150 for performing predetermined process on the image data received from the capsule medical device 100 by the receiving device 130 and displaying the processed image data to the observer. The receiving device 130 and the display device 150 are external devices disposed on the outside of the subject 900.

To the receiving device 130, a portable recording medium 140 such as a flash memory (registered trademark) or a smart card (registered trademark) can be inserted. In the portable recording medium 140, for example, image data and the like received from the capsule medical device 100 is stored. The observer moves the portable recording medium 140 from the receiving device 130 to the display device 150, thereby moving the image data received from the capsule medical device 100 by the receiving device 130 to the display device 150. The invention is not limited to the case but image data received by the receiving device 130 may be transmitted to the display device 150 via a communication cable 159 or the like in an almost real-time manner. The observer executes a predetermined process such as a reproducing process or a converting process on the image data stored in the portable recording medium 140 by using the display device 150. As the display device 150, an information processor such as a personal computer or a workstation, a display such as a liquid crystal display or an organic EL display can be used.

Capsule Medical Device

Figure 2:
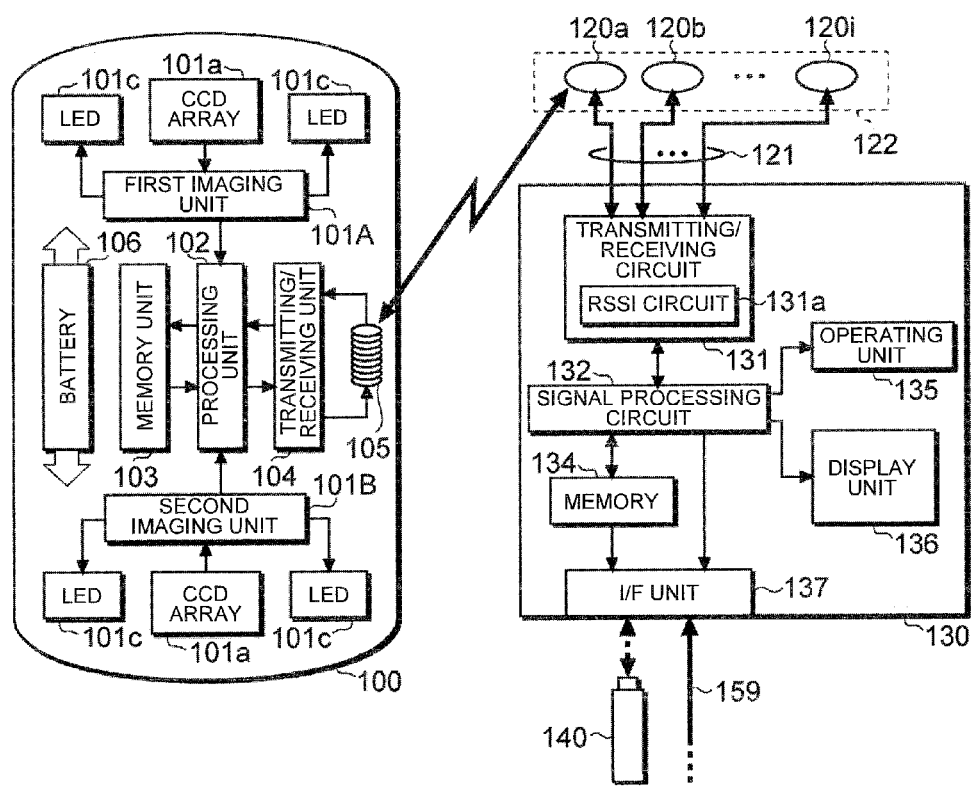
FIG. 2 is a block diagram showing a schematic internal configuration of a capsule medical device according to any of first to fourth embodiments or its modifications of the invention and a receiving device performing wireless communication with the capsule medical device.
Figure 3:
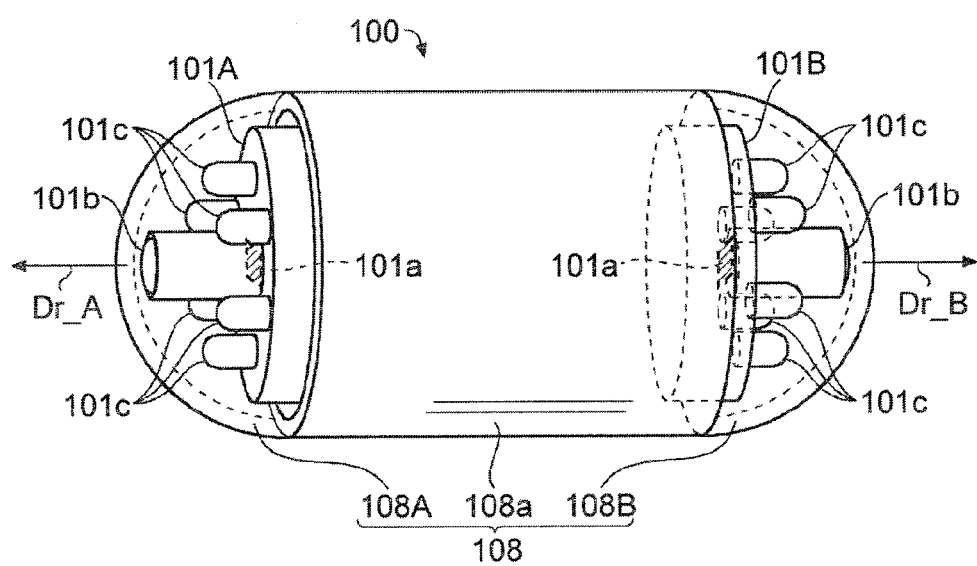
FIG. 3 is a perspective view illustrating schematic appearance of the capsule medical device according to any of the first to fourth embodiments of the invention and their modifications.

An example of the schematic configuration of the capsule medical device 100 is shown in FIGS. 2 and 3. FIG. 2 is a block diagram showing a schematic internal configuration of the capsule medical device 100 and the receiving device 130 performing wireless communication with the capsule medical device 100. FIG. 3 is a perspective view showing a schematic appearance of the capsule medical device 100.

As shown in FIG. 2, the capsule medical device 100 includes: two imaging units for illuminating and imaging the inside of the subject 900 (hereinbelow, for convenience, called first and second imaging units 101A and 101B), a processing unit 102 for executing a process on the image data generated by the first and second imaging units 101A and 101B and other various processes, a memory unit 103 for storing the image data and the like processed by the processing unit 102, a transmitting/receiving unit 104 and an antenna 105 for transmitting/receiving a signal to/from the receiving device 130, and one or more batteries 106 for supplying power to the internal of the capsule medical device 100.

The first and second imaging units 101A and 101B, the processing unit 102, the memory unit 103, the transmitting/receiving unit 104, and the battery 106 are housed in a water-tight casing 108 made by a container 108a and caps 108A and 108B. As shown in FIG. 3, the container 108a has a hollow cylindrical shape. On the other hand, the caps 108A and 108B each having a hollow hemispherical shape are fit in two aperture formed in the container 108a, thereby water-tightly sealing the casing 108. At least the caps 108A and 108B are made of transparent resin or the like.

Each of the first and second imaging units 101A and 101B is imaging means for imaging the inside of the subject 900 and generating image data and has an LED 101c for illuminating the inside of the subject 900, a CCD array 101a in which Charge Coupled Devices (CCDs) as light emitting elements are arranged in a matrix, an objective lens 101b disposed on the light reception face side of the each CCD array 101a, and a drive circuit (not shown) for driving the LED 101c and a drive circuit (not shown) for driving the CCD array 101a. Each of the first and second imaging units 101A and 101B periodically operates (for example, twice per second), thereby imaging the inside of the subject 900 and generating image data. The generated image data is read by the drive circuit and supplied to the processing unit 102 in an almost real-time manner.

The processing unit 102 executes predetermined signal process on input image data and supplies the processed image data to the transmitting/receiving unit 104. The transmitting/receiving unit 104 mainly functions as output means for outputting image data generated by the first or second imaging unit 101A or 101B to the receiving device 130 on the outside. Therefore, the image data subjected to the predetermined signal process by the processing unit 102 is transmitted by radio in an almost real-time manner from the transmitting/receiving unit 104 to the receiving device 130 via the antenna 105. The invention, however, is not limited to the case. Image data subjected to the predetermined image signal process may be stored in the memory unit 103 and, after the capsule medical device 100 is taken from the subject 900, the image data may be taken from the memory unit 103.

To the transmitted/accumulated image data, for example, a camera ID for identifying the first or second imaging unit 101A or 101B is added by the processing unit 102 so that the imaging unit (the first or second imaging unit 101A or 101B) which has generated the image data is identified. To the transmitted/accumulated image data, a time stamp indicative of imaging time is also added by the processing unit 102 so that the imaging time of the image data is known. That is, the processing unit 102 functions as identification information adding means that adds, to image data, a camera ID as identification information for identifying an imaging unit which generates the image data and imaging time adding means that adds imaging time to the image data. In the following description, the camera ID="1" is added to the first imaging unit 101A, and the camera ID="2" is added to the second imaging unit 101B.

As shown in FIGS. 1 and 3, the LED 101c and the CCD array 101a in the first imaging unit 101A are disposed in the casing 108 so that an illuminating/imaging direction Dr_A is directed to the outside of the casing 108 via the transparent cap 108A. Similarly, as shown in FIGS. 1 and 3, the LED 101c and the CCD array 101a in the second imaging unit 101B are disposed in the casing 108 so that an illuminating/imaging direction Dr_B is directed to the outside of the casing 108 via the transparent cap 108B. The CCD array 101a is disposed in an almost center in a section perpendicular to the longitudinal direction of the casing 108. A plurality of LEDs 101c are disposed point-symmetrical or line-symmetrical so as to surround the CCD array 101a in the section.

As the antenna 105 of the capsule medical device 100, for example, a loop antenna is used. The invention is not limited to the loop antenna. Various antennas such as a dipole antenna can be used regardless of directivity.

Receiving Device

As shown in FIGS. 1 and 2, image data transmitted by radio from the capsule medical device 100 is received by a plurality of antennas 120a to 120i (hereinbelow, reference numeral of arbitrary one of the antennas 120a to 120i will be set as 120) disposed on the surface of the subject 900 and input to the receiving device 130 disposed on the outside of the subject 900 via a cable 121. An example of a schematic configuration of the receiving device 130 according to the first embodiment will be described with reference to FIG. 2.

As shown in FIG. 2, the receiving device 130 has a transmitting/receiving circuit 131 for transmitting/receiving a signal to/from the capsule medical device 100 via the antenna 120, a signal processing circuit 132 for executing a predetermined process on the signal (particularly, image data) input from the transmitting/receiving circuit 131, a memory 134 for storing the image data or the like subjected to the predetermined process, and an operating unit 135 and a display unit 136 realizing the Graphical User Interface (GUI) function for making the observer input various operations and instructions to the capsule medical device 100 and the receiving device 130.

The plurality of antennas 120 are, for example, dipole antennas, loop antennas, or the like and are fixed to a jacket 122 the subject 900 can wear. The number of antennas 120, an arrangement pattern, and an object to which the antennas 120 are fixed can be variously changed.

Image data input from the capsule medical device 100 via the antenna 120 is supplied to the signal processing circuit 132 via the transmitting/receiving circuit 131, subjected to a predetermined signal process in the signal processing circuit 132 and, after that, temporarily stored in the memory 134. After that, the image data stored in the memory 134 is accumulated in the portable recording medium 140 via an interface (I/F) 137 or transmitted from the interface (I/F) 137 to the display device 150 via the communication cable 159 in an almost real-time manner. The interface 137 can be variously changed according to the data input/output method such as a Universal Serial Bus (USB) interface or a communication interface used for Local Area Network (LAN) or the like.

Display Device

Figure 4:
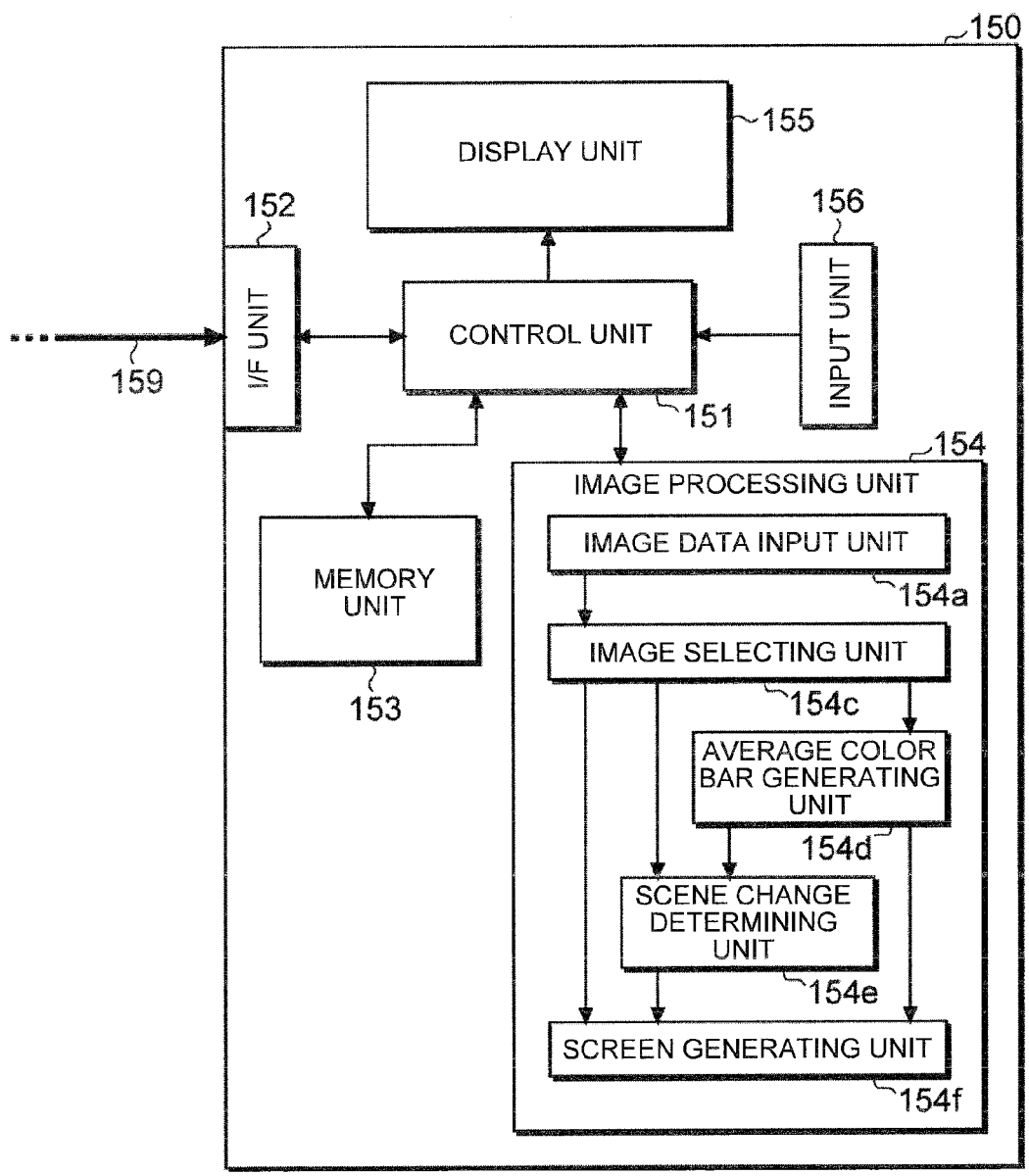
FIG. 4 is a block diagram showing an example of a schematic configuration of the display device according to the first embodiment of the invention.

As described above, the display device 150 is a display such as an information processor, a liquid crystal display, or an organic EL display of a personal computer, a workstation, or the like. An example of the configuration of the display device 150 according to the first embodiment will be described in detail with reference to FIGS. 1 and 4. FIG. 4 is a block diagram showing a schematic configuration example of the display device 150 according to the first embodiment.

As shown in FIGS. 1 and 4, the display device 150 has a control unit 151 for controlling internal operations and input/output of data, a memory unit 153 for temporarily storing image data or the like input from an interface unit 152 via the portable recording medium 140 or the communication cable 159, an image processing unit 154 for executing a predetermined process on input image data and generating a GUI screen provided to the observer, a display unit 155 for displaying the GUI screen generated by the image processing unit 154, and an input unit 156 with which the observer inputs various instructions on the basis of the GUI screen displayed on the display unit 155.

The interface unit 152 functions as input means that receives image data output from the capsule medical device 100 via the receiving device 130. The image data input from the interface unit 152 is temporarily stored in the memory unit 153 via the control unit 151. After that, the image data is properly input to the image processing unit 154 and is subjected to a predetermined process. The processed image data may be stored again in, for example, the memory unit 153.

The image processing unit 154 executes a predetermined process which will be described later on the input image data and, after that, generates a GUI screen to be provided for the observer by using the processed image data. The GUI screen generated is supplied to the display unit 155 via the control unit 151 and displayed on the display unit 155. The display unit 155 and the input unit 156 provides the GUI function using the GUI screen being displayed to the observer. The observer selects a target function by variously operating the input unit 156 such as a mouse and a keyboard, and displays/reproduces a desired image on the display unit 155. The observer reads a displayed/reproduced image, thereby diagnosing the inside of the subject 900.

The image processing unit 154 will be described more specifically. As shown in FIG. 4, the image processing unit 154 includes an image data input unit 154a for receiving image data from the control unit 151 or the like, an image selecting unit 154c for selecting image data to be displayed, an average color bar generating unit 154d that generates average color bars 15A and 15B to be described later by using the selected image data, a scene change determining unit 154e that determines a scene change in a series of image data, and a screen generating unit 154f that generates a GUI screen by using the selected image data and the average color bars 15A and 15B.

The image data input to the image processing unit 154 is, first, input to the image selecting unit 154c by the image data input unit 154a.

The image selecting unit 154c selects image data to be displayed on the basis of image process results on successive image data in the image data input from the image data input unit 154a. As an image process result, for example, the degree of similarity, the degree of correlation, a motion vector, or the like of successive image data calculated from feature points in image data can be used. That is, for example, the image selecting unit 154c performs image process on image data input from the image data input unit 154a and selects image data to be displayed on the basis of the degree of similarity, the degree of correlation, a motion vector, or the like of the successive image data obtained by the image process. As described above, the image selecting unit 154c functions as selecting means that selects image data to be displayed in a series of image data by camera IDs. The selected image data is, for example, supplied to each of the average color bar generating unit 154d, the scene change determining unit 154e, and the screen generating unit 154f.

The average color bar generating unit 154d calculates an average color of the image data. The average color bar generating unit 154d generates the average color bars 15A and 15B by connecting images of the calculated average colors by imaging units, that is, by camera IDs in accordance with the order of image data. The average color bar generating unit 154d may divide image data to a plurality of regions and calculate an average color of each of the divided plurality of regions. For example, the average color bar generating unit 154d may divide image data into four regions which are arranged in the vertical direction, calculate an average color for each of the divided regions, connect images of the calculated average colors in the divided regions, thereby generating the average color bars 15A and 15B. In this case, the average color bars 15A and 15B become an image of a band shape made of a plurality of lanes arranged along the time base (time series) of the image data.

The scene change determining unit 154e determines image data whose scene is changed from image data input from the image selecting unit 154c and supplies the result to the screen generating unit 154f. The invention is not limited to the case but the scene change determining unit 154e may receive images of the average color bars 15A and 15B generated by the average color bar generating unit 154d and determine the image data whose scene has changed. The image in which a scene change occurs may be properly selected by the observer.

Image data in which a scene change occurs is, for example, image data obtained when the capsule medical device 100 passes through a predetermined region (such as pylorus, intenstinal cerum, hepatic flexure, splenic flexure, and sigmoid) in the lumen 902 in the subject 900. In the first embodiment, a series of image data is divided into a plurality of regions (called scenes) divided as specific regions in the lumen 902 in the subject 900.

Figure 5:
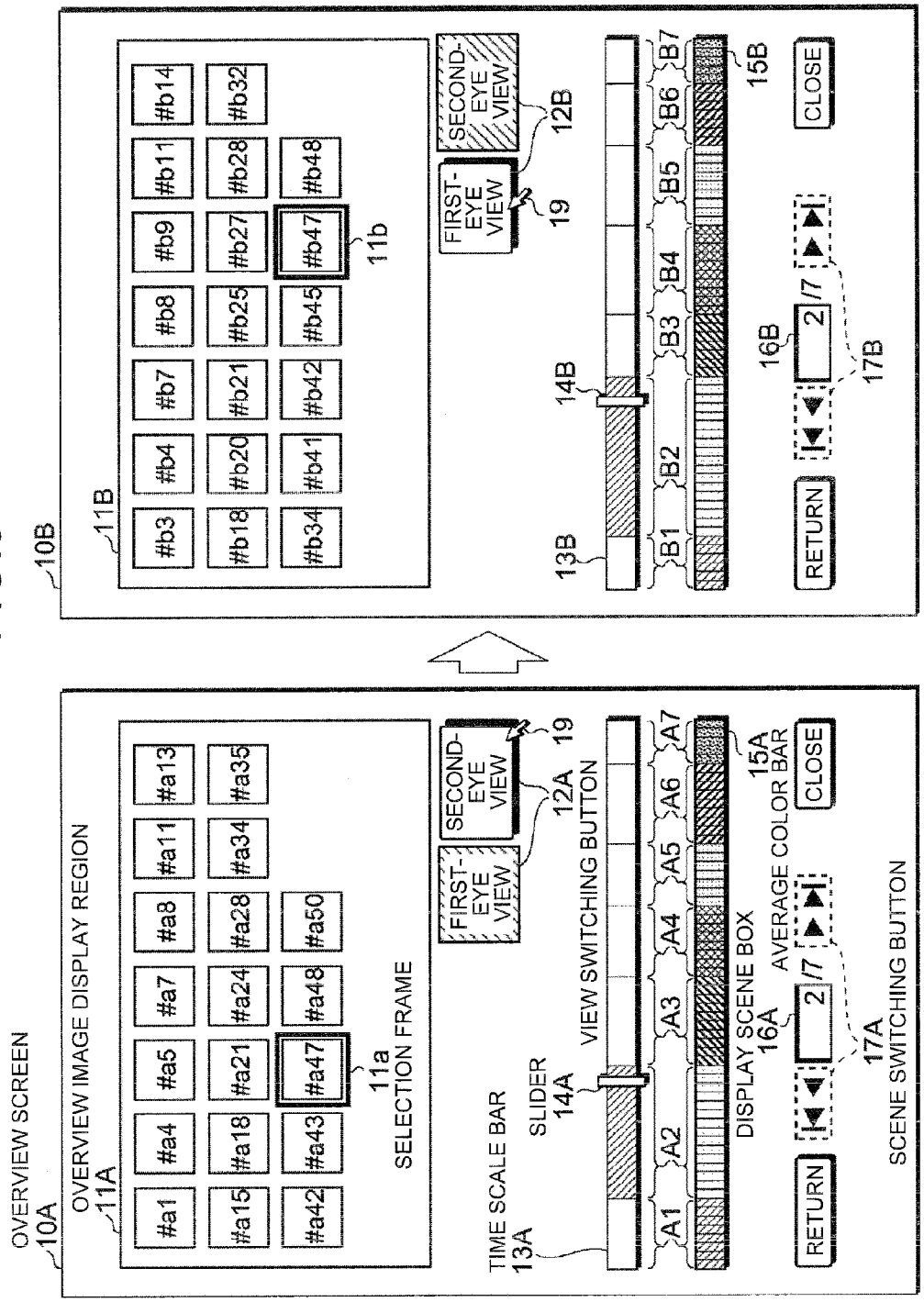
FIG. 5 is a diagram showing an example of an overview screen in the first embodiment of the invention.

FIG. 5 shows an example of the GUI screen (overview screens 10A and 10B) generate by the screen generating unit 154f in the first embodiment.

As shown in FIG. 5, the GUI screen according to the first embodiment includes, mainly, the overview screens 10A and 10B. The overview screen 10A includes an overview image display region 11A as a GUI screen displaying a list of image data captured by the first imaging unit 101A (camera ID=1) by pages, and displaying a list of the image data in the pages reduced to a predetermined size, view switching buttons 12A for switching a display screen between the overview screens 10A and 10B, a time scale bar 13A linked to the imaging time base of entire image data, a slider 14A indicating the position of a reduced image being selected in the overview image display region 11A, in the imaging time base of the entire image data and providing the observer with the GUI function of switching the page displayed, an average color bar 15A linked to the time scale bar 13A, a display scene box 16A indicative of the order of a scene being displayed in the overview image display region 11A in all of scenes (refer to scenes A1 to A7 and B1 to B7 in FIG. 5), and a scene switching button 17A for switching the scene to be displayed in the overview image display region 11A. In the overview image display region 11A, for example, a selection frame 11a indicative of a frame being selected is added to the reduced image being selected.

Similarly, the overview screen 10B includes an overview image display region 11B as a GUI screen displaying a list of image data captured by the second imaging unit 101B (camera ID=2) by scenes, and displaying a list of the image data in the scenes reduced to a predetermined size, view switching buttons 12B for switching a display screen between the overview screens 10A and 10B, a time scale bar 13B linked to the imaging time base of entire image data, a slider 14B indicating the position of a reduced image being selected in the overview image display region 11B, in the imaging time base of the entire image data and providing the observer with the GUI function of switching the page displayed, an average color bar 15B linked to the time scale bar 13B, a display scene box 16B indicative of the order of a scene being displayed in the overview image display region 11B in all of scenes, and a scene switching button 17B for switching the scene to be displayed in the overview image display region 11B. In the overview image display region 11B, for example, a selection frame 11b indicative of a frame being selected is added to the reduced image being selected.

The screen generating unit 154f (in the following description, properly replaced with a screen generating unit 154f, 254f, 354f, or 454f), the overview screens 10A and 10B generated by the screen generating unit 154f (in the following description, properly replaced with overview screens 10A-1 and 10B-1, 10A-2a and 10B-2a, 10A-2b and 10B-2b, 10A-2c and 10B-2c, 10A-2d and 10B-2d, 10A-3 and 10A-4, 10-5, 10-6, 10-7, 10A-8 and 10B-8, 20, 20-2, 20-3, 30, 30-1a, 30-1b, 30-1c, 30-1d, 30-2, 30-3, 30-4, or 40), and the display unit 155 function as list display means that displays a list of image data.

By seeing the list of reduced images being displayed in the overview image display regions 11A and 11B of the overview screens 10A and 10B, the observer can know the entire image in the subject 900 in each of the scenes. For example, by clicking the view switching button 12A by operating a pointer 19 using the mouse, keyboard, joystick, or the like of the input unit 156, the observer switches the GUI screen displayed in the display unit 155 between the overview screens 10A and 10B. The view switching buttons 12A and 12B, the input unit 156 for operating the buttons and inputting instructions, and the screen generating unit 154f operating on the basis of a switching instruction from the view switching buttons 12A and 12B function as switching means that switches image data to be displayed from image data with one of the camera IDs being displayed to image data with the other camera ID.

In the first embodiment as described above, a list of reduced images is displayed by the imaging units (the first eye (that is, the first imaging unit 101A) and the second eye (that is, the second imaging unit 101B)) generating image data and by scenes in one screen. Consequently, even in the medical system 1 using the capsule medical device 100 having a plurality of eyes (for example, two eyes), the number of pieces or size of image data presented at a time to the observer does not have to be decreased. As a result, also in the case of using the capsule medical device 100 having the plurality of eyes (for example, two eyes), the amount of information, which can be presented at a time to the observer, can be prevented from decreasing.

A sign indicated with "#" in the description is a number assigned to image data by scenes in accordance with a time series and is an image ID for identifying image data (or a reduced image).

When the observer clicks any of reduced images with the pointer 19, the reduced image to be clicked is selected, and the selection frame 11a/11b is added to the selected image. When the observer makes, for example, the slider 14A/14B slide along the time scale bars 13A and 13B, responding reduced images on the time base of the time scale bars 13A and 13B are automatically selected in the positions of the sliders 14A and 14B, respectively. When each of the sliders 14A and 14B moves over two scenes, the scene displayed in the overview image display region 11A or 11B is switched. Further, when the observer operates the scene switching button 17A with the pointer 19, a list of reduced images in scenes operated is displayed in the overview image display region 11A/11B, and the slider 14A/14B travels to the position on the time scale bar 13A/13B corresponding to, for example, the head of the switched scene. As an initial selected image, for example, the reduced image at the head is set automatically.

Operation

Figure 6:
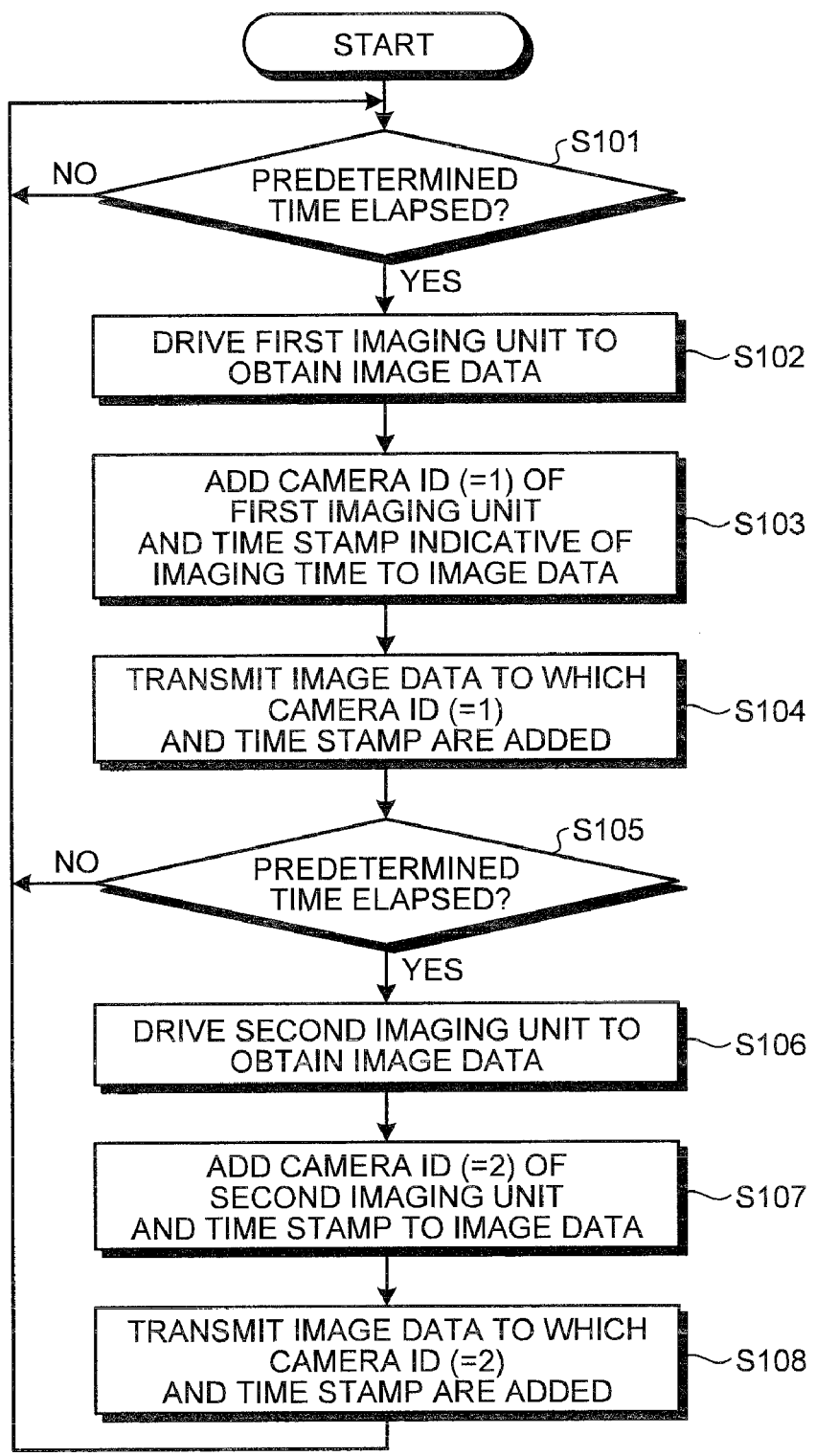
FIG. 6 is a flowchart showing an example of outline operation of the capsule medical device according to the first embodiment of the invention.
Figure 7:
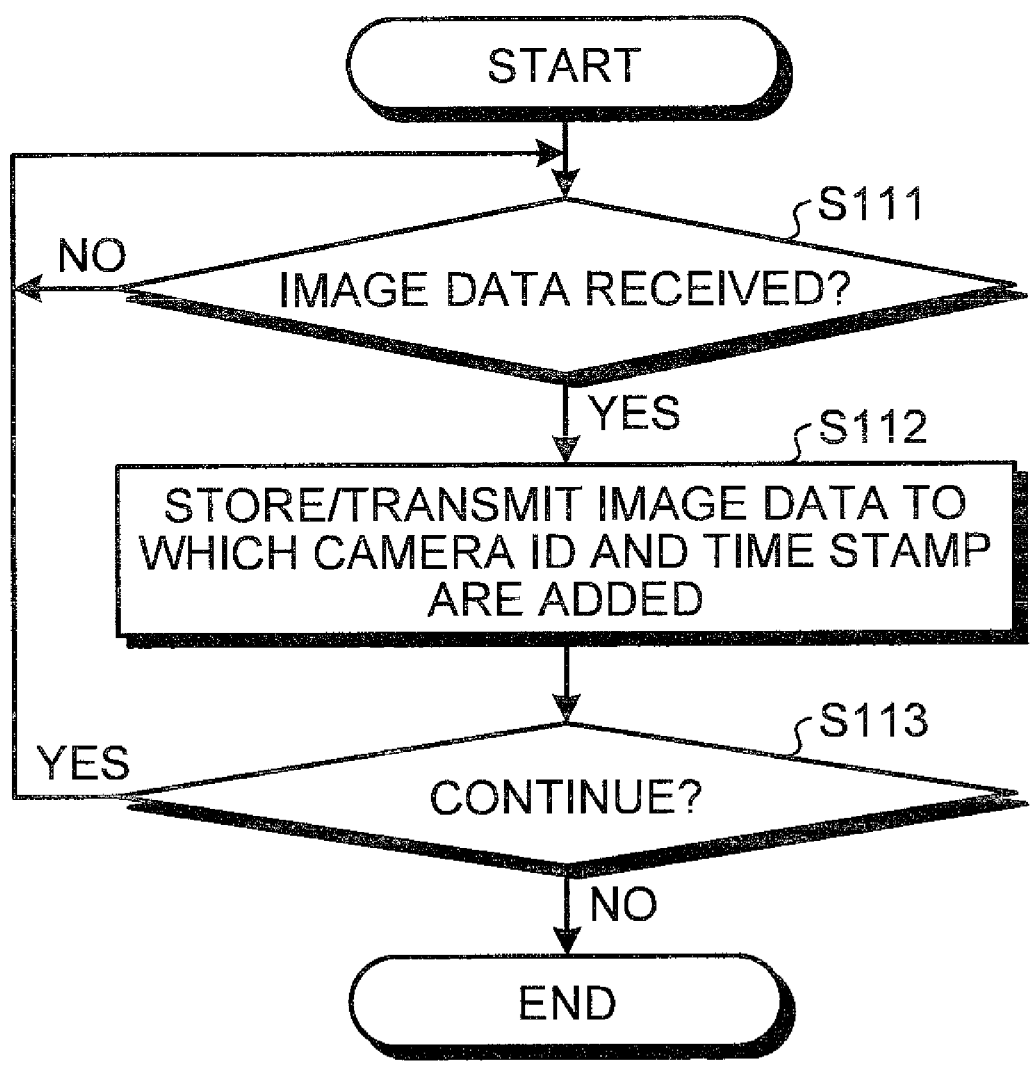
FIG. 7 is a flowchart showing an example of outline operation of a receiving device in the first embodiment of the invention.
Figure 8:
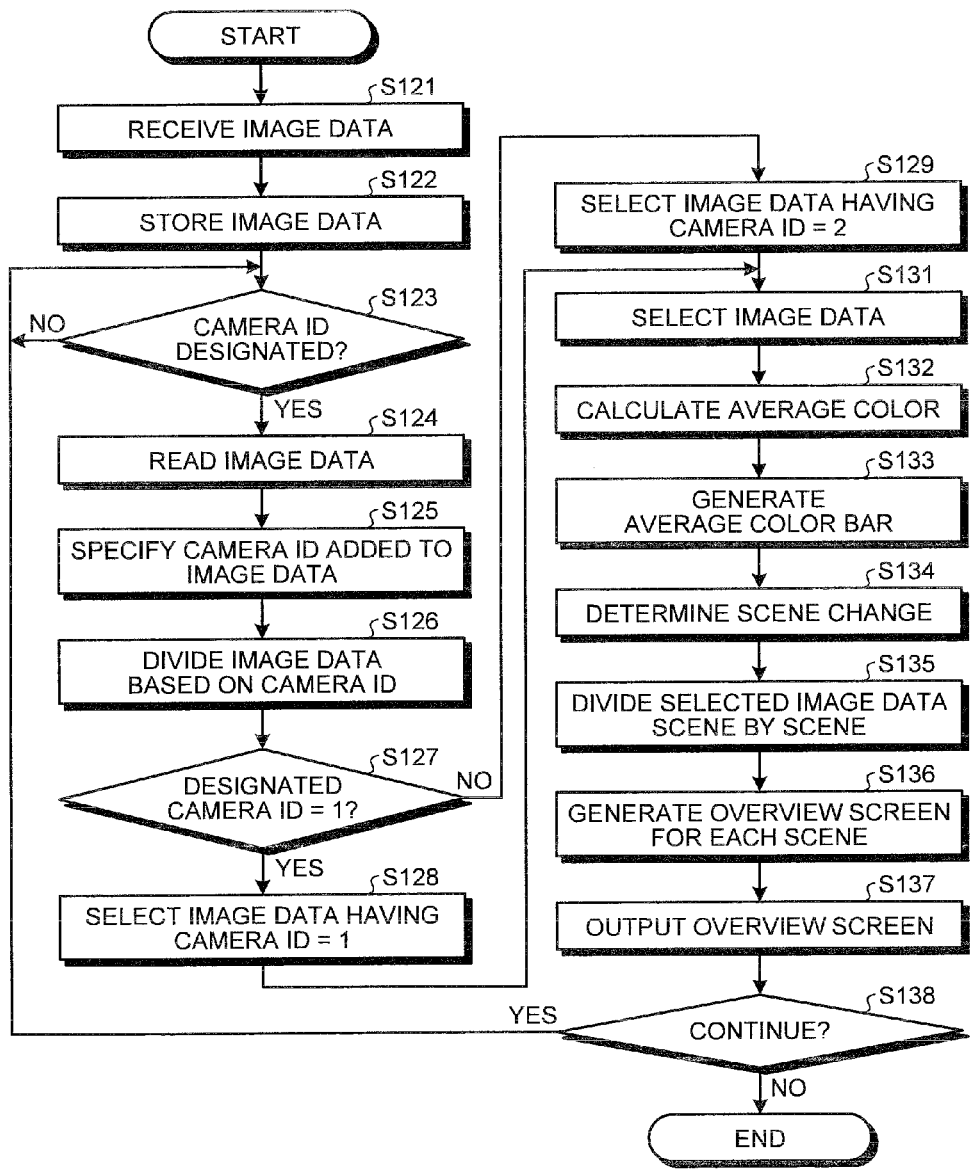
FIG. 8 is a flowchart showing an example of outline operation of the display device in the first embodiment of the invention.

The operation of the medical system 1 according to the first embodiment will now be described in detail with reference to the drawings. FIG. 6 is a flowchart showing an example of schematic operation of the capsule medical device 100 according to the first embodiment. FIG. 7 is a flowchart showing an example of schematic operation of the receiving device 130 according to the first embodiment. FIG. 8 is a flowchart showing an example of schematic operation of the display device 150 according to the first embodiment.

First, the operation of the capsule medical device 100 will be described. As shown in FIG. 6, after startup, the capsule medical device 100 drives the first imaging unit 101A periodically (at predetermined intervals), thereby obtaining image data from the first imaging unit 101A (Yes at step S101, and S102). Subsequently, the capsule medical device 100 adds the camera ID (=1) given to the first imaging unit 101A to the image data obtained from the first imaging unit 101A, obtains time at which the image data is obtained, and adds a time stamp indicative of the time to the image data (step S103). The capsule medical device 100 transmits, as a wireless signal, the image data to which the camera ID (=1) and the time stamp are added from the transmitting/receiving unit 104 to the receiving device 130 via the antenna 105 (step S104).

The capsule medical device 100 determines whether predetermined time has elapsed since the determination in step S101 (step S105). When the predetermined time has elapsed (Yes at step S105), the capsule medical device 100 drives the second imaging unit 101B, thereby obtaining image data from the second imaging unit 101B (step S106). Subsequently, the capsule medical device 100 adds the camera ID (=2) given to the second imaging unit 101B to the image data obtained from the second imaging unit 101B, obtains time at which the image data is obtained, and adds a time stamp indicative of the time to the image data (step S107). The capsule medical device 100 transmits, as a wireless signal, the image data to which the camera ID (=2) and the time stamp are added from the transmitting/receiving unit 104 to the receiving device 130 via the antenna 105 (step S108), and returns to step S101. By such operations, image data obtained by the first and second imaging units 101A and 101B is periodically transmitted by radio from the capsule medical device 100 to the receiving device 130. The operations of the capsule medical device 100 shown in FIG. 6 are continued until no power of the battery 106 in the capsule medical device 100 remains.

On the other hand, as shown in FIG. 7, the receiving device 130, for example, always monitors whether image data is received from the capsule medical device 100 (No at step S111). In the case where image data is received (Yes at step S111), the receiving device 130 stores the received image data to which the camera ID and the timestamp are added from the interface 137 into the portable recording medium 140 or transmits the image data from the interface 137 to the display device 150 via the communication cable 159 (step S112). After that, the receiving device 130 determines whether the operation is continued, for example, whether an operation end instruction is received from the operating unit 135 (step S113). In the case of continuing the operation (Yes at step S113), the receiving device 130 returns to step S111 and waits for reception of next image data. On the other hand, in the case where the operation is not continued (No at step S113), the operation is finished.

As shown in FIG. 8, when the display device 150 receives image data from the interface unit 152 using the portable recording medium 140 or the communication cable 159 as a medium (step S121), the display device 150 temporarily stores the image data in the memory unit 153 or the like via the control unit 151 (step S122).

Next, the display device 150 monitors whether the camera ID is designated (No at step S123). At the startup of the overview screen, for example, it is set so that the camera ID (=1) of the first imaging unit 101A is automatically designated. That is, in response to an instruction to start the GUI function, the camera ID=1 is automatically designated in the startup operation. After the overview screen 10A or 10B is displayed, the observer clicks the view switching button 12A/12B with the input unit 156 using the mouse or the like to designate the camera ID.

When the camera ID is designated (Yes at step S123), the display device 150 reads stored image data from the memory unit 153 or the like (step S124). The read image data is supplied to the image data input unit 154a in the image processing unit 154. To the image data input unit 154a, the camera ID designated in step S123 is also supplied. In the following, description will be given paying attention to the operations of the units realizing the steps (refer to FIG. 4).

The image data input unit 154a specifies each of the camera IDs attached to input image data (step S125) and divides the image data by the imaging units (101A and 101B), that is, by the camera IDs on the basis of the camera IDs (step S126).

Next, the image data input unit 154a determines whether the camera ID=1 is designated in step S123 (step S127). In the case where the camera ID=1 is designated (Yes at step S127), the image data input unit 154a selects image data having the camera ID=1 (step S128). On the other hand, in the case where the camera ID designated is not "1" (No at step S127), that is, in the case where the camera ID=2 is selected, the image data input unit 154*a* selects image data having the camera ID=2 (step S129). The image processing unit 154 receives image data from the control unit 151 at the time point when the image data is fetched from the I/F unit 152 and performs the imaging process by camera IDs. As a result, an object of a representative image is determined for each camera ID.

The image selecting unit 154*c* specifies image data to be displayed on the basis of an image process result obtained by performing the imaging process on input image data and selects it (step S131). The selected image data is input to each of the average color bar generating unit 154*d*, the scene change determining unit 154*e*, and the screen generating unit 154*f*.

The average color bar generating unit 154*d* to which the selected image data is input selects image data by camera IDs and calculates an average color of each image data (or each of divided regions obtained by dividing the image data) (step S132) and, on the basis of the calculation results, generates the average color bar 15A/15B obtained by connecting images of average colors along time series of the image data (step S133). The connection of images along time series can be performed, for example, in accordance with the time stamps attached to the selected image data. An average color may be calculated in accordance with the color of a feature part included in each image data (or each of divided regions of the image data). Further, the generated average color bar 15A/15B is supplied to the screen generating unit 154*f*. Alternatively, the generated average color bar 15A/15B may be supplied to the scene change determining unit 154*e*.

The scene change determining unit 154*e* determines image data in which a scene change occurs on the basis of image process results of successive image data in the image data input from the image selecting unit 154*c* (step S134). The scene change determination result is supplied to the screen generating unit 154*f*.

The screen generating unit 154*f* divides the selected image data supplied, the scene change determination result, and the image data selected by camera ID scene by scene (step S135). Subsequently, the screen generating unit 154*f* generates the overview screens 10A and 10B shown in FIG. 5 from the image data divided scene by scene and the images of the average color bars 15A and 15B (step S136) and outputs it to the display unit 155 via the control unit 151 (step S137). As a result, the overview screens 10A and 10B as the GUI screens are displayed in the display unit 155, and the GUI function using them is provided to the observer.

After that, the display device 150 determines whether the operation is continued, for example, whether an operation end instruction is input from the input unit 156 (step S138). In the case where the operation is continued (Yes at step S138), the display device 150 returns to step S123 and waits for the next designation of a camera ID. On the other hand, in the case where the operation is not continued (No at step S138), the operation is finished.

As described above, in the first embodiment, a list of reduced images is displayed by the imaging units (the first eye (that is, the first imaging unit 101A) and the second eye (that is, the second imaging unit 101B)) generating image data and by scenes in one screen. Consequently, even in the medical system 1 using the capsule medical device 100 having a plurality of eyes (for example, two eyes), the number of pieces or size of image data presented at a time to the observer does not have to be decreased. As a result, also in the case of using the capsule medical device 100 having the plurality of eyes (for example, two eyes), the amount of information, which can be presented at a time to the observer, can be prevented from decreasing.

Modification 1-1

Figure 9:
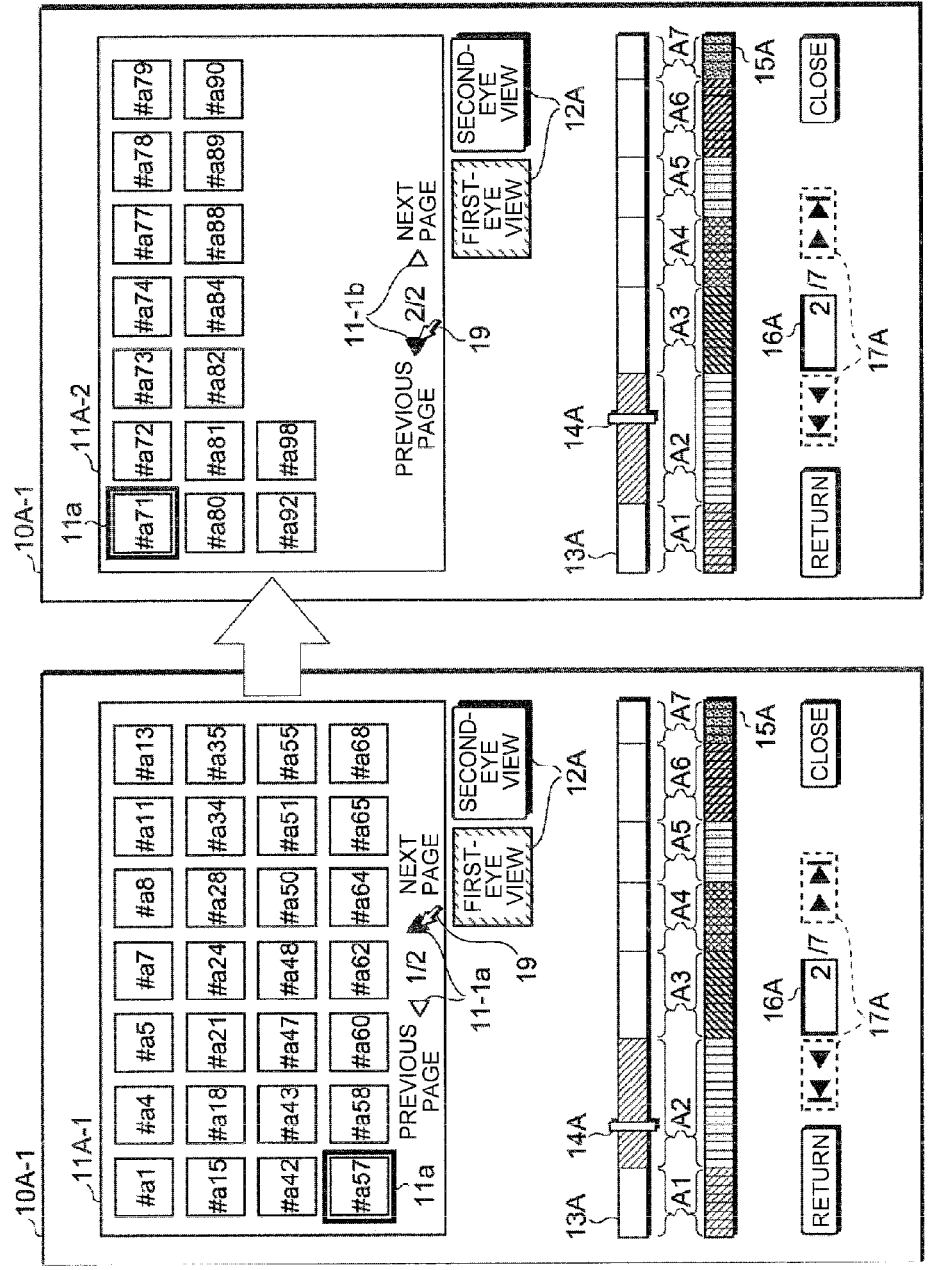
FIG. 9 is a diagram showing an example of an overview screen according to modification 1-1 of the first embodiment of the invention.

Although a list of reduced images of all of image data included in each scene is displayed at a time in the overview image display region 11A in the overview screen 10A in the first embodiment, the invention is not limited to the case. That is, as shown in an overview screen 10A-1 according to the modification 1-1 of the first embodiment of FIG. 9, the number of reduced images displayed in one overview image display region 11A-1 is fixed. When the number of reduced images in each scene to be displayed exceeds the limitation number of the overview image display region 11A-1 of each page, the remaining reduced images may be displayed in an overview image display region in a following page (for example, an overview image display region 11A-2 in the second page). In this case, a page being displayed is switched by, for example, clicking page switching buttons 11-1*a* and 11-1*b* in the overview image display regions 11A-1 and 11A-2.

Since such page division of the overview image display region can be easily realized by the screen generating unit 154*f* in the image processing unit 154 in FIG. 4, the detailed description will not be repeated. The modification 1-1 is similarly applied to the overview screen 10B.

Modification 1-2a

In the case of disposing the two imaging units (101A and 101B) so that the illuminating/imaging directions Dr_A and Dr_B are opposite to each other in the longitudinal direction of the capsule medical device 100, an imaging unit whose illuminating/imaging direction matches the travel direction (for convenience of explanation, the first imaging unit 101A) captures an image of a region p1 (specific region p1) such as a projection in the lumen 902 just before it passes through the specific region p1. On the other hand, an imaging unit whose illuminating/imaging direction is opposite to the travel direction (for convenience of explanation, the second imaging unit 101B) captures an image of the specific region p1 after it passes through the specific region p1.

Figure 10:
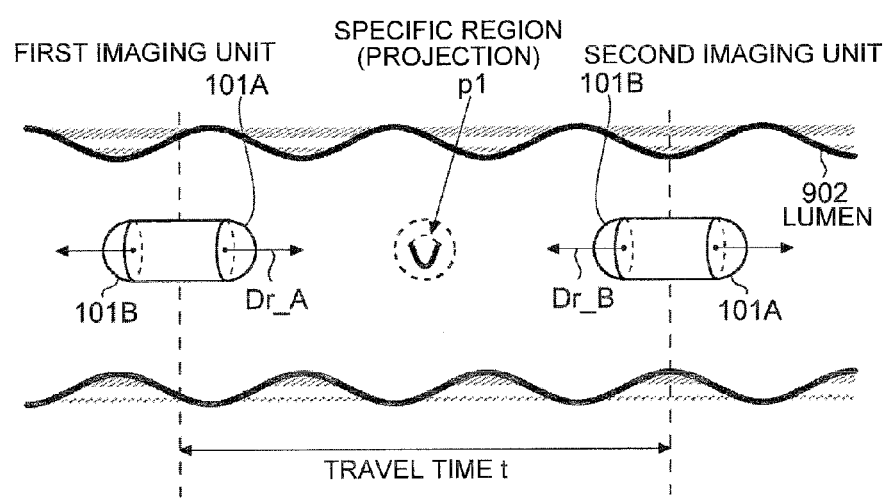
FIG. 10 is a conceptual diagram showing the flow of image capturing performed by first and second imaging units disposed so as to face each other over a specific region (projection) in a lumen in modification 1-2a of the first embodiment of the invention.
Figure 11:
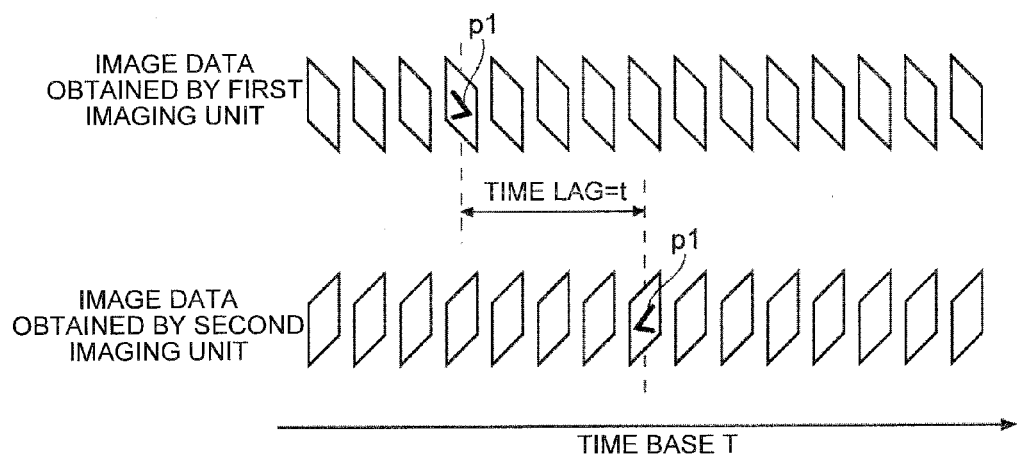
FIG. 11 is a diagram for explaining the order along time base T, of image data obtained by the first imaging unit and image data obtained by the second imaging unit in the modification 1-2a of the first embodiment of the invention.

When travel time required for the capsule medical device 100 to pass through the specified region p1 is set to "t" as shown in FIG. 10, as illustrated in FIG. 11, a time lag of the travel time "t" necessary for the capsule medical device 100 passes through the specified region p1 occurs between the timing at which the first imaging unit 101A images the specified region p1 and the timing at which the second imaging unit 101B images the specified region p1. FIG. 10 is a conceptual diagram showing the flow of capturing images by the first and second imaging units 101A and 101B disposed so as to be opposed to each other over the same specified region (projection) p1 in the lumen 902. FIG. 11 is a diagram for explaining the order along the time base T (actual time base of imaging operation) of image data captured by the first imaging unit 101A and image data captured by the second imaging unit 101B.

In the modification 1-2a, a sync interval of an image of image data of the camera ID=1 and an image of image data of the camera ID=2 of the same position in the subject 900 is changed on the basis of the travel time "t" so that the image data can be processed as the image data captured at the same timing or close timings. By the operation, the image data of the same position can be displayed while adjusting the positions on the overview image display regions 11A-2*a* and 11B-2*a* between the overview screen (refer to an overview screen 10A-2*a* in FIG. 15) displaying a list of image data of one of camera IDs (=1) and an overview screen (refer to an overview screen 10B-2a of FIG. 15 displaying a list of image data of the other camera ID (=2). In the following description, the changing of the sync intervals of images will be called synchronization. The case of displaying image data obtained by the first imaging unit 101A and image data obtained by the second imaging unit 101B while adjusting them between different overview screens (11A-2a and 11B-2a) will be described in detail as the modification 1-2a of the embodiment with reference to the drawings.

Image data to which different camera IDs are added can be synchronized by, for example, specifying the imaging unit (101A or 101B) directed opposite to the travel direction of the capsule medical device 100 and adding the travel time "t" to the timing of obtaining the image data by the specified imaging unit (in the description, it is assumed that the imaging unit directed in the travel direction is the second imaging unit 101B). The invention is not limited to the case but it can be variously modified. For example, information indicative of the order in time series (image numbers) is added to image data, and image data of different camera IDs are synchronized on the basis of the information. As the imaging timing, any information by which the imaging timing can be specified can be used such as the time stamps added to image data or lapse time counted since startup of the capsule medical device 100 (which is to be added to image data).

By making the travel time "t" as a factor of synchronization freely changeable, synchronization precision can be further increased. For example, there is a case that the travel speed of the capsule medical device 100 varies among regions (scenes) in the lumen 902. In the modification 1-2a, by changing the travel speed (that is, travel time "t") of the capsule medical device 100 scene by scene, image data is synchronized. The travel speed of the capsule medical device 100 in the lumen 902 can be specified by an experiment, simulation, or empirically. By designing the system so that the value of the factor of synchronization such as the travel time "t" or image number can be properly changed by the observer, an administrator, or the like before or during use of the medical system, accuracy or flexibility of synchronization can be further increased.

The medical system according to the modification 1-2a has a configuration similar to that of the medical system 1 according to the first embodiment. In the modification 1-2a, the display device 150 is replaced with a display device 150-2a shown in FIG. 12. In the following description, the same reference numerals are designated to components similar to those of the foregoing first embodiment and its modification, and repetitive description will not be repeated.

Figure 12:
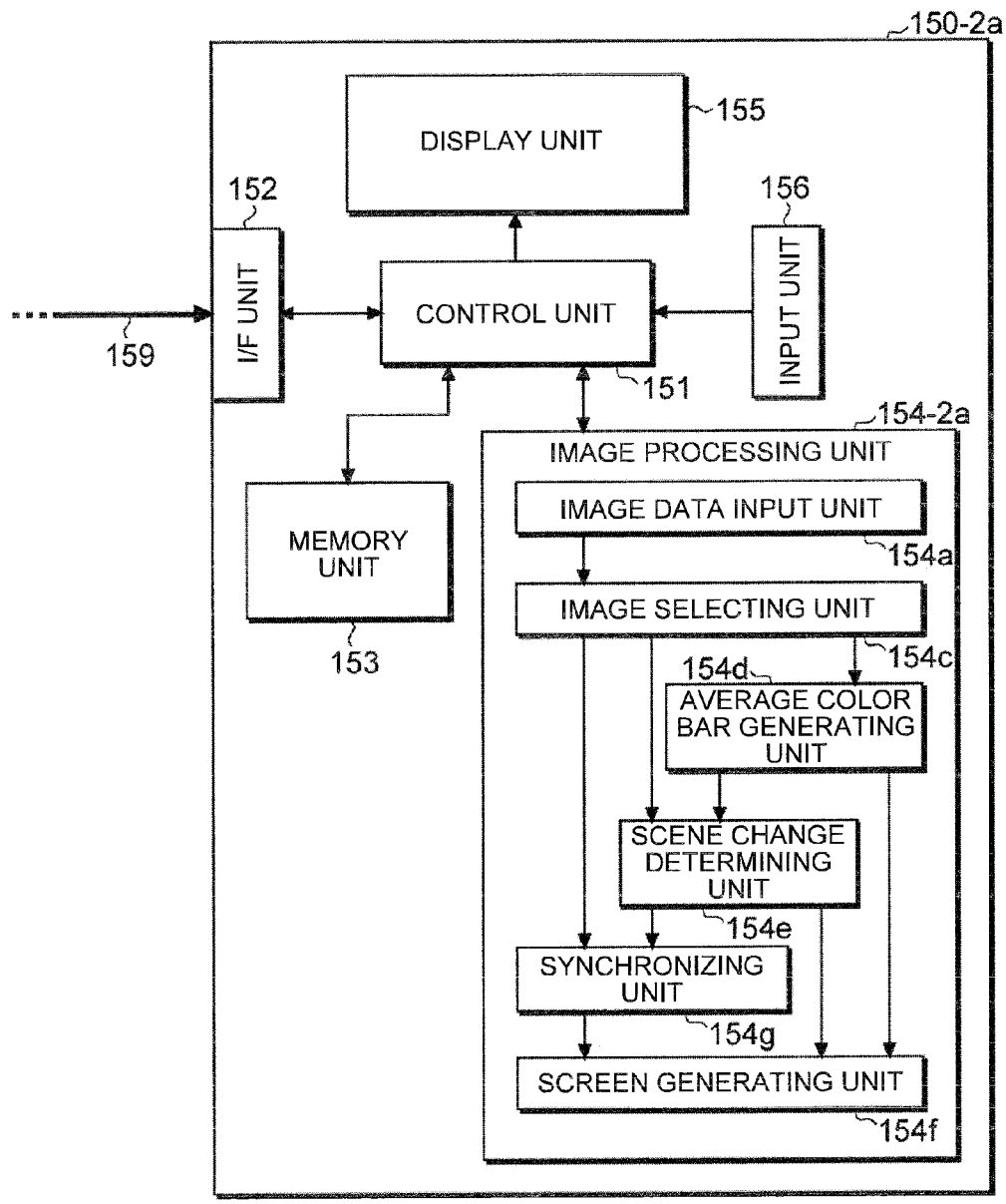
FIG. 12 is a block diagram showing an example of a schematic configuration of the display device according to the modification 1-2a of the first embodiment of the invention.

FIG. 12 is a block diagram showing a schematic configuration example of the display device 150-2a according to the modification 1-2a. As illustrated in FIG. 12, in the display device 150-2a, the image processing unit 154 shown in FIG. 4 is replaced with an image processing unit 154-2a. The image processing unit 154-2a has a configuration similar to that of the image processing unit 154 and, in addition, a synchronizing unit 154g for synchronizing image data captured by the first imaging unit 101A (that is, image data having the camera ID=1) and image data captured by the second imaging unit 101B (that is, image data having the camera ID=2).

In the modification 1-2a, the result of the scene change determination made by the scene change determining unit 154e is also supplied to the synchronizing unit 154g. For example, on the basis of the supplied scene change determination result, the synchronizing unit 154g specifies the camera ID of the imaging unit directed opposite to the travel direction in the lumen 902 of the capsule medical device 100.

The synchronizing unit 154g generates new image capture time by adding the travel time "t" of each preset scene to image capture time indicated by the time stamp of each image data to which the specified camera ID is added and associates the new image capture time with the image data. In such a manner, the image data captured by the first imaging unit 101A and that captured by the second imaging unit 101B is synchronized. That is, by adding the travel time (predetermined time) "t" to the image capture time indicated by the time stamp added to image data of one of camera IDs (the camera ID of the imaging unit directed opposite to the travel direction in the lumen 902 of the capsule medical device 100) in image data, the synchronizing unit 154g synchronizes the image data of the camera ID with image data of the other camera ID. The invention, however, is not limited to the case. By subtracting the travel time (predetermined time) "t" from the image capture time indicated by the time stamp added to the image data of the camera ID of the imaging unit directed in the travel direction in the lumen 902 of the capsule medical device 100, the image data of the camera ID and that of the other camera ID may be synchronized.

That is, the synchronizing unit 154g functions as synchronizing means that synchronizes the image data of one of the camera IDs with image data of the other camera ID generated by capturing an image of the same specified region p1 from a different direction. Therefore, in the overview screens 10A-2a and 10B-2a, a list of image data (its reduced images) by camera IDs is displayed on the basis of the synchronization by the synchronizing unit 154g.

Figure 13:
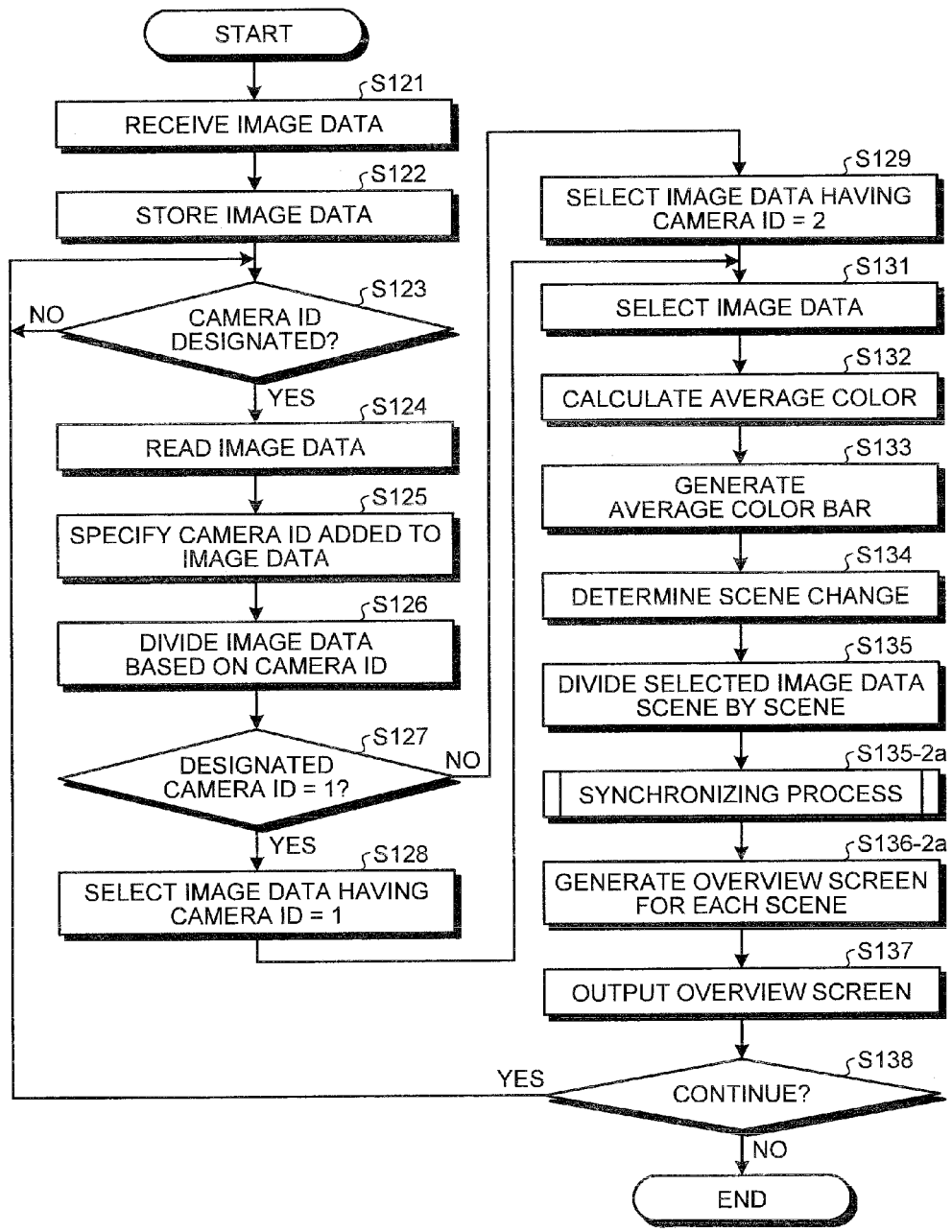
FIG. 13 is a flowchart showing an example of outline operation of the display device according to the modification 1-2a of the first embodiment of the invention.
Figure 14:
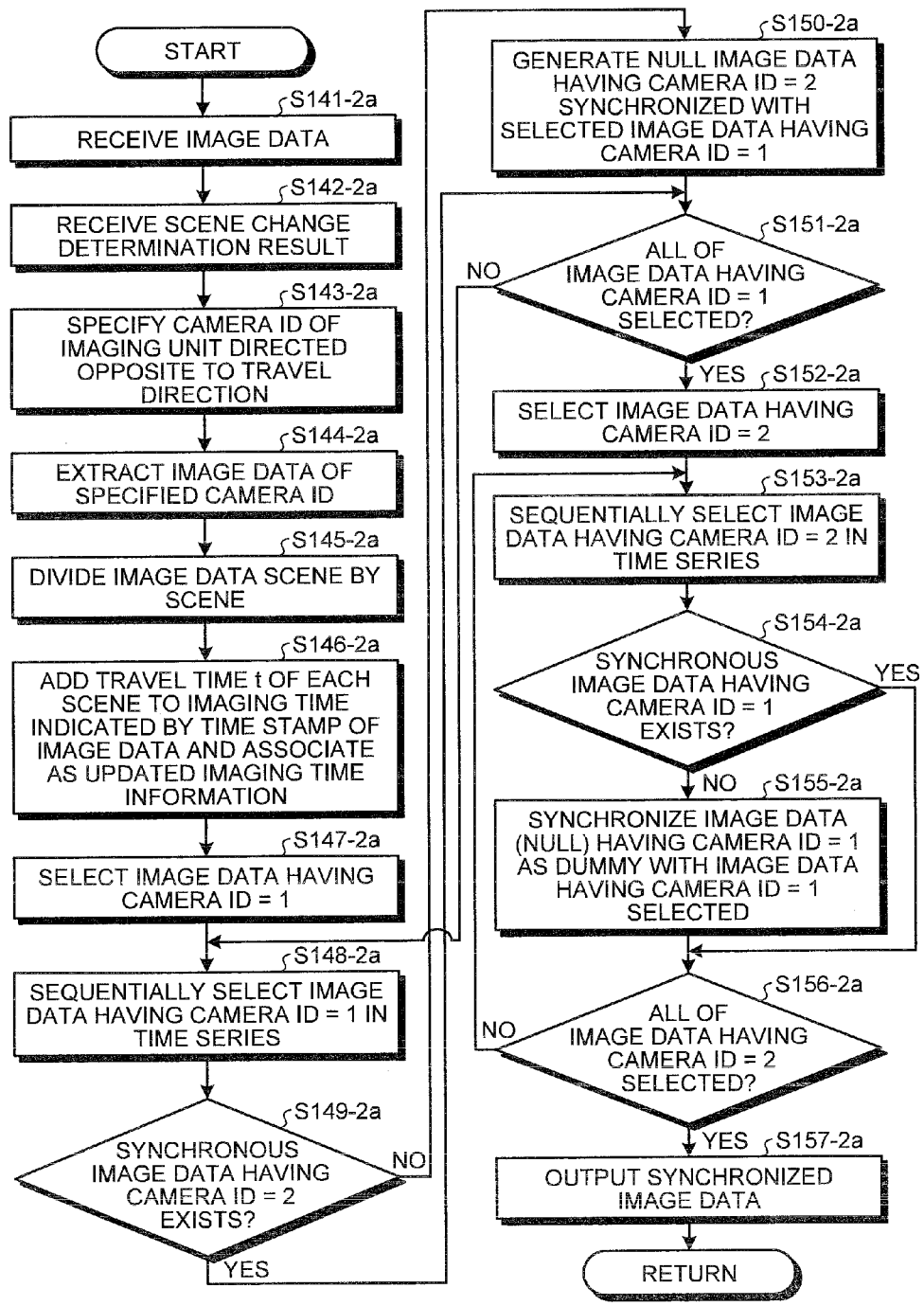
FIG. 14 is a flowchart showing a concrete example of synchronizing process in step S135-2a in FIG. 13.

The operation of the display device 150-2a according to the modification 1-2a will be described in detail with reference to the drawings. FIG. 13 is a flowchart showing a schematic operation example of the display device 150-2a according to the modification 1-2a. FIG. 14 is a flowchart showing a concrete example of the synchronizing process in step S135-2a in FIG. 13.

In the modification 1-2a, first, the display device 150-2a executes operations similar to those in steps S121 to S135 in FIG. 8 to divide the image data selected by camera IDs scene by scene (refer to steps S121 to S135 in FIG. 13). Subsequently, the synchronizing unit 154g of the display device 150-2a executes a process of synchronizing the image data of camera ID=1 and the image data of camera ID=2 on the basis of the selected image data and the scene change determination result (step S135-2a). The details of the synchronizing process will be described later with reference to FIG. 14.

Next, the screen generating unit 154f generates the overview screens 10A-2a and 10B-2a (refer to FIG. 15) by using the synchronized image data and the generated average color bars 15A and 15B (step S136-2a) and outputs them to the display unit 155 via the control unit 151 (step S137). The overview screens 10A-2a and 10B-2a as GUI screens are displayed on the display unit 155, and the GUI function using them is provided to the observer.

After that, the display device 150-2a determines whether the operation is continued, for example, whether an operation end instruction is supplied from the input unit 156 (step S138). In the case of continuing the operation (Yes at step S138), the display device 150-2a returns to step S123 and waits for the next designation of a camera ID. On the other hand, in the case where the operation is not continued (No at step S138), the operation is finished.

In the synchronizing process in step S135-2a in FIG. 13, the synchronizing unit 154g in the image processing unit 154-2a receives image data selected by the image selecting unit 154c (step S141-2a) and receives a scene change determination result output from the scene change determining unit 154e (step S142-2a).

Next, on the basis of the supplied scene change determination result, the synchronizing unit 154g specifies the camera ID of the imaging unit directed opposite to the travel direction of the capsule medical device 100 (step S143-2a). The imaging unit directed opposite to the travel direction of the capsule medical device 100 can be specified from motion vectors in image data sequentially obtained by imaging units. The invention, however, is not limited to the case but can be variously modified by, for example, specifying the camera ID on the basis of the difference between timings of obtaining image data in which a scene change occurs. That is, the imaging unit obtaining image data in which the same scene change occurs can be also specified as an imaging unit directed in the travel direction of the capsule medical device 100. In such a manner, the scene change determining unit 154e and the synchronizing unit 154g function as specifying means that specifies an imaging unit whose imaging direction matches the travel direction of the capsule medical device 100 from image process results of successive image data in a series of image data by camera IDs.

The synchronizing unit 154g extracts image data to which the camera ID specified in step S143-2a is added from image data input from the image selecting unit 154c (step S144-2a) and divides the image data scene by scene on the basis of the scene change determination result (step S145-2a).

The synchronizing unit 154g adds the travel time "t" which is pre-set for each scene to the imaging time indicated by the time stamp of the image data divided scene by scene and associates the resultant time as updated imaging time information to the image data (step S146-2a). Image data associated with the updated imaging time information is stored together with image data which is not to be updated (that is, image data to which the camera ID of the imaging unit directed in the travel direction of the capsule medical device 100 is added) into, for example, the memory unit 153 and the like.

The synchronizing unit 154g reads the selected image data stored from the memory unit 153 and the like and selects the image data of the camera ID=1 from the image data (step S147-2a). Subsequently, the synchronizing unit 154g sequentially selects the image data having the camera ID=1 selected in time series in accordance with the imaging time indicated by the time stamps (step S148-2a) and determines whether the selected image data having the camera ID=2 synchronized with the selected image data exists (step S149-2a). The presence or absence of the synchronous image data can be determined by, for example, detecting whether the imaging time (imaging time indicated by the time stamp or the updated imaging time information) of selected image data having the camera ID=1 and that of selected image data having the camera ID=2 are within a predetermined time.

In the case where it is determined in step S149-2a that the synchronous selected image data having the camera ID=2 exists (Yes at step S149-2a), the synchronizing unit 154g moves to step S151-2a. Image data having the camera ID=1 and that having the camera ID=2 is synchronized by associating updated imaging time information. The invention is not limited to the case. A configuration of synchronizing two pieces of image data such as a configuration of setting new flags or the like and associating synchronous two pieces of image data may be separately provided.

On the other hand, in the case where synchronous selected image data having the camera ID=2 does not exist (No at step S149-2a), the synchronizing unit 154g generates "null" image data having the camera ID=2 having the same time stamp as that of target image data having the camera ID=1 (step S150-2a). That is, the synchronizing unit 154g generates, as a dummy, null image data having the camera ID=2 at the same imaging time as that of the target image data having the camera ID=1. In the modification 1-2a, in the case where image data of the other camera ID to be synchronized with image data of one of the camera IDs is not selected as image data to be displayed, the synchronizing unit 154g generates null image data having the other camera ID, and synchronizes it with the image data of one camera ID.

Next, the synchronizing unit 154g determines whether all of selected image data having the camera ID=1 has been selected (step S151-2a). In the case where all of the image data has not been selected (No at step S151-2a), the synchronizing unit 154g returns to step S148-2a, and selects the next selected image data having the camera ID=1.

On the other hand, in the case where all of image data having the camera ID=1 selected in step S148-2a has been selected (Yes at step S151-2a), next, the synchronizing unit 154g selects image data having the camera ID=2 in the selected image data stored in the memory unit 153 or the like (step S152-2a) and sequentially selects the selected image data having the camera ID=2 in time series in accordance with imaging time indicated by the time stamps or updated imaging time information (step S153-2a). Subsequently, the synchronizing unit 154g determines whether the selected image data having the camera ID=1 synchronized with the selected image data exists (step S154-2a).

In the case where it is determined in step S154-2a that selected image data having the camera ID=1 synchronized exists (Yes at step S154-2a), the synchronizing unit 154g moves to step S156-2a. On the other hand, in the case where the selected image data having the camera ID=1 synchronized does not exist (No at step S154-2a), the synchronizing unit 154g generates null image data which has the camera ID=1 and is the same as the image data of camera ID=2 determines whether the selected image data having the same time stamp (step S155-2a). That is, the synchronizing unit 154g generates, as a dummy, null image data having camera ID=2 and the same imaging time as that of the target image data having camera ID=1.

Next, the synchronizing unit 154g determines whether all of image data having the camera ID=2 selected in step S148-2a has been selected (step S156-2a). In the case where all of the image data has not been selected (No at step S156-2a), the synchronizing unit 154g returns to step S153-2a, and selects the next selected image data having the camera ID=2. On the other hand, in the case where all of the image data having the camera ID=2 selected in step S153-2a has been selected (Yes at step S156-2a), the synchronizing unit 154g outputs the synchronized image data to the screen generating unit 154f (step S157-2a), and returns to the operations shown in FIG. 13.

Figure 15:
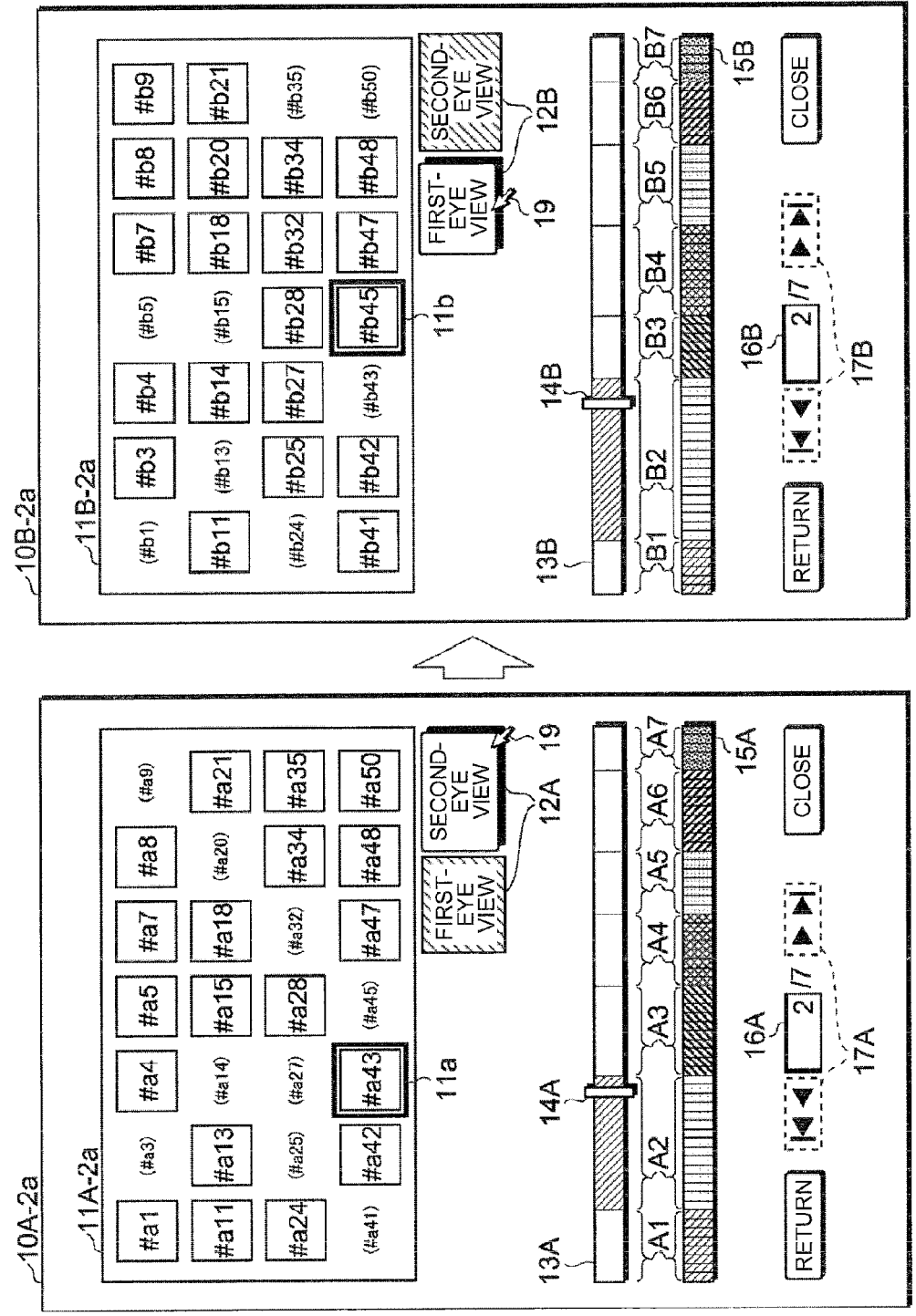
FIG. 15 is a diagram showing an example of an overview screen according to modification 1-2a of the first embodiment of the invention.

By the configuration and operation as described above, in the modification 1-2a, the overview screens 10A-2a and 10B-2a as shown in FIG. 15 are generated and displayed. FIG. 15 is a diagram showing an example of the overview screens 10A-2a and 10B-2a according to the modification 1-2a.

As shown in FIG. 15, in an overview image display region 11A-2a in the overview screen 10A-2a, reduced images generated from image data selected out of image data #a1 to #a50 having the camera ID=1 are displayed. On the other hand, in an overview image display region 11B-2a, reduced images generated from image data selected from image data #b1 to #b50 having the camera ID=2 are displayed. In each of the overview image display regions 11A-2a and 11B-2a, display parts having no synchronous image data are blank. For example, a region in the overview image display region 11B-2a, in which a reduced image of image data #b1 of the camera ID=2 synchronized with a reduced image of image data #a1 of the camera ID=1 in the overview image display region 11A-2a is to be displayed, is blank. In other words, portions in which image data synchronized does not exist are blank.

As described above, in the modification 1-2a, in addition to effects similar to those of the first embodiment, image data obtained by capturing images of the same position by different eyes can be displayed while being synchronized. Therefore, the observer can easily observe the region in the subject 900 from a plurality of angles.

Modification 1-2b

Figure 16:
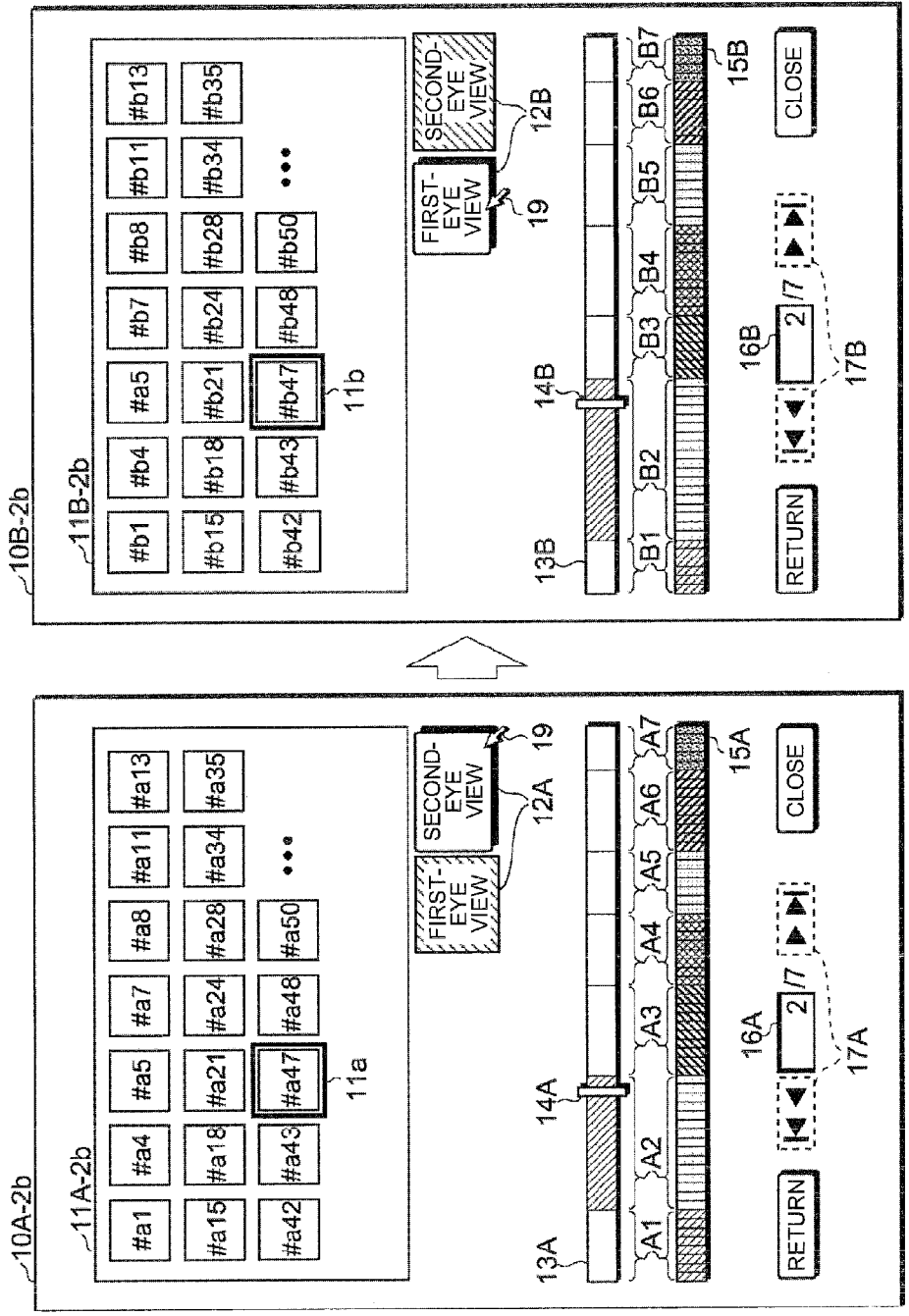
FIG. 16 is a diagram showing an example of an overview screen according to modification 1-2b of the first embodiment of the invention.

As reduced images displayed in the overview screen of image data having the camera ID=1 and reduced images displayed in the overview screen of camera ID=2, as shown in overview screens 10A-2b and 10B-2b according to the modification 1-2b of the first embodiment of FIG. 16, a list of reduced images displayed in an overview image display region 11A-2b and a list of reduced images displayed in an overview image display region 11B-2b can be made by reduced images of selected image data having the camera ID=1 and reduced images of image data having the camera ID=2 synchronized with the selected image data of the camera ID=1. That is, image data having the camera ID=2 synchronized with selected image data having the camera ID=1 can be automatically selected and displayed in a list. In the following, the case will be described in detail as modification 1-2b of the first embodiment with reference to the drawings.

A medical system according to modification 1-2b has a configuration similar to that of the medical system 1 according to the first embodiment. In the modification 1-2b, the display device 150 is replaced with a display device 150-2b shown in FIG. 17. In the following description, the same reference numerals are designated to components similar to those of the foregoing first embodiment and its modification, and repetitive description will not be repeated.

Figure 17:
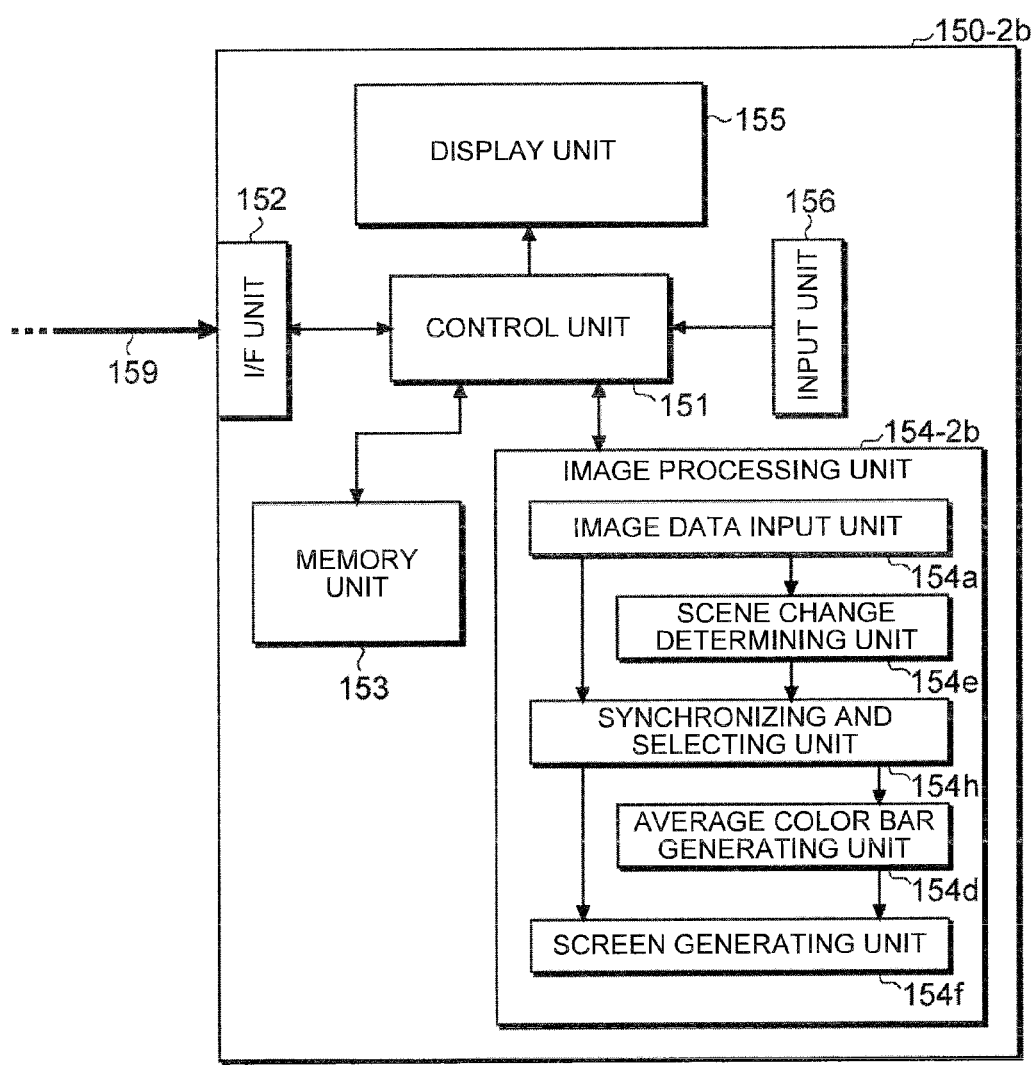
FIG. 17 is a block diagram showing an example of a schematic configuration of the display device according to the modification 1-2b of the first embodiment of the invention.

FIG. 17 is a block diagram showing a schematic configuration example of the display device 150-2b according to the modification 1-2b. As illustrated in FIG. 17, in the display device 150-2b, the image processing unit 154 shown in FIG. 4 is replaced with an image processing unit 154-2b. The image processing unit 154-2b has a configuration similar to that of the image processing unit 154 except that the image selecting unit 154c is replaced with a synchronizing and selecting unit 154h. Further, in the image processing unit 154-2b, image data output from the image data input unit 154a is supplied to each of the scene change determining unit 154e and the synchronizing and selecting unit 154h. A result of scene change determination made by the scene change determining unit 154e is input to the synchronizing and selecting unit 154h.

Figure 18:
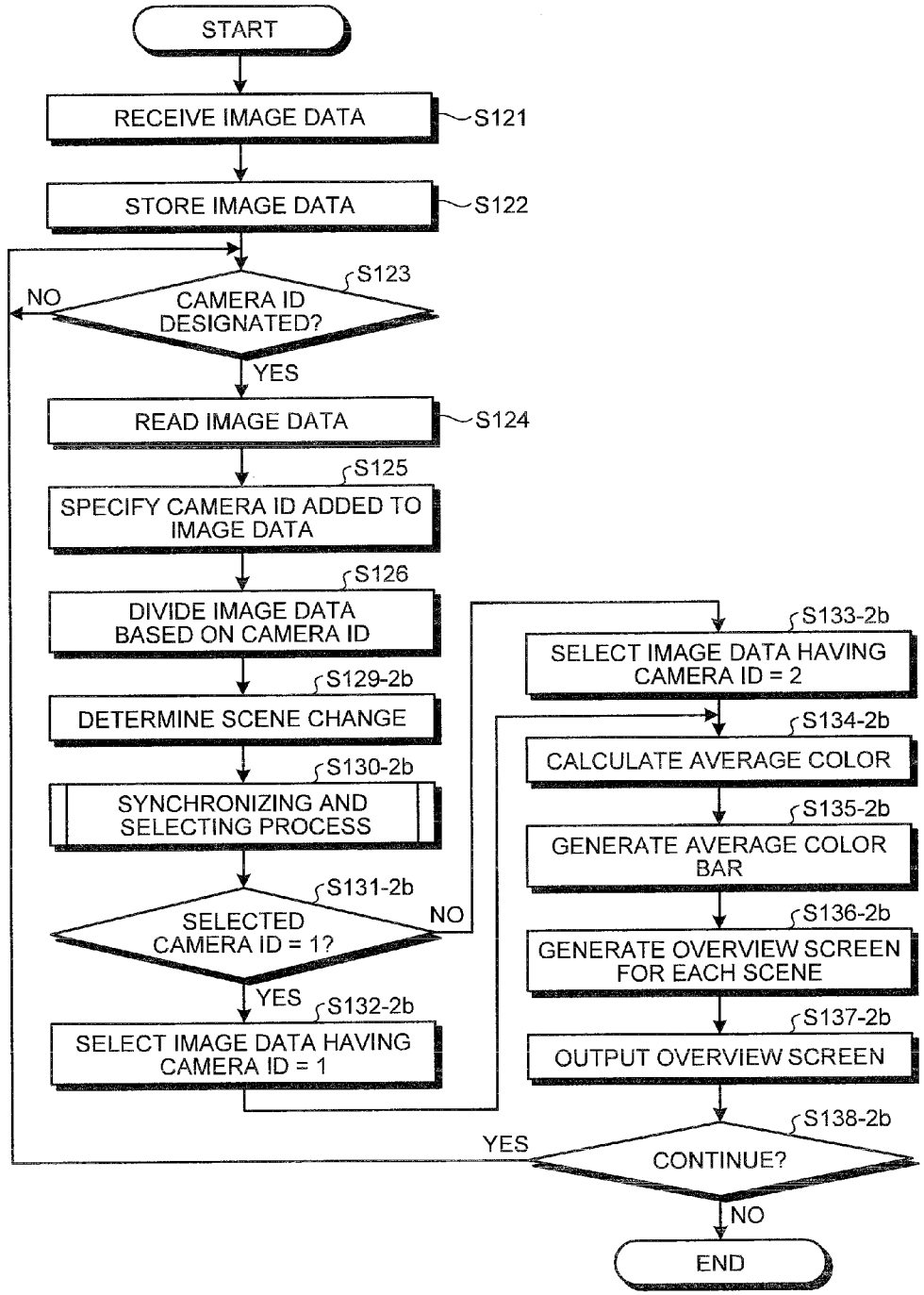
FIG. 18 is a flowchart showing an example of outline operation of the display device according to the modification 1-2b of the first embodiment of the invention.
Figure 19:
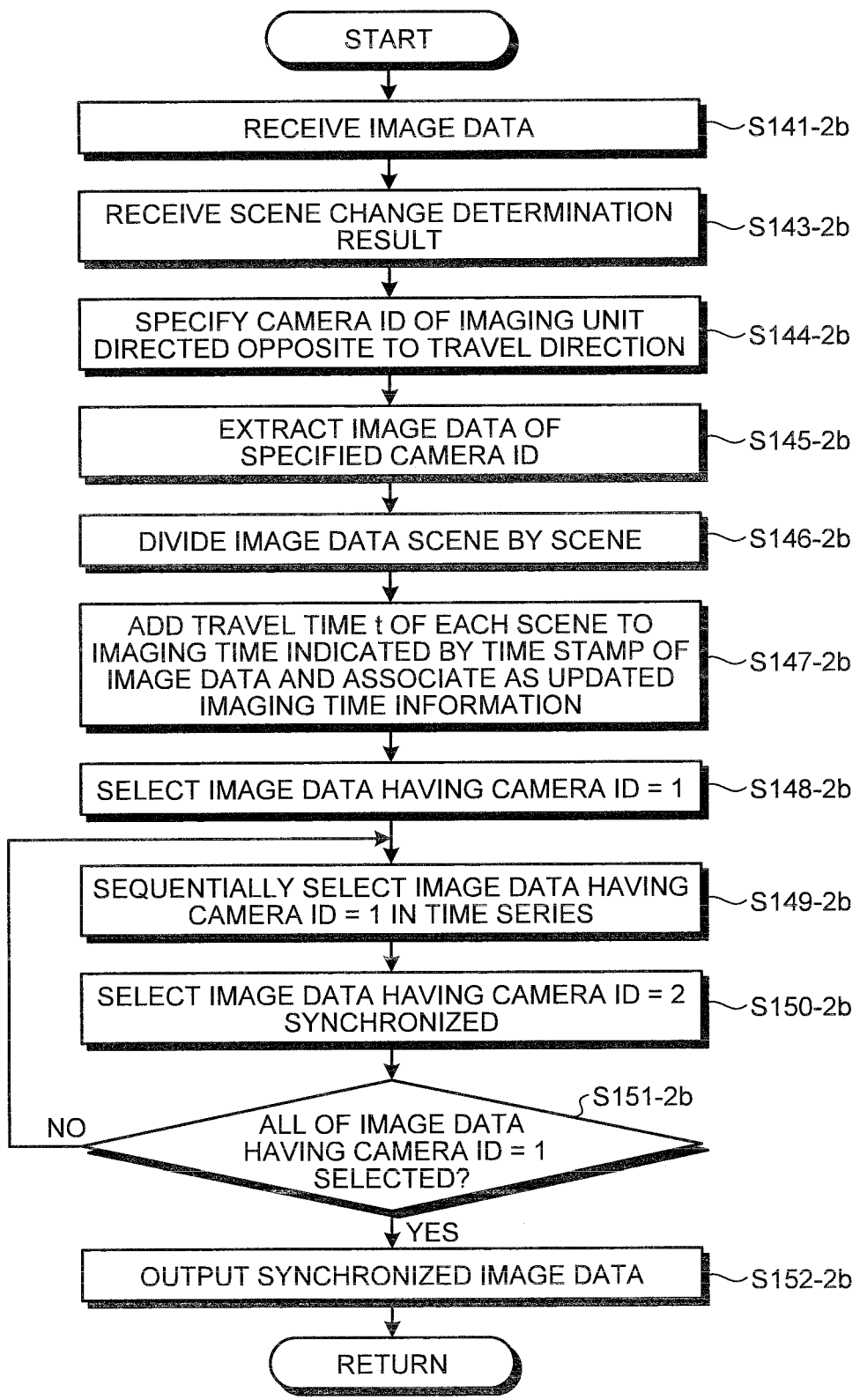
FIG. 19 is a flowchart showing a concrete example of image data selecting process in step S130-2b in FIG. 18.

The operation of the display device 150-2b and the synchronizing and selecting unit 154h according to the modification 1-2b will be described in detail with reference to the drawings. FIG. 18 is a flowchart showing a schematic operation example of the display device 150-2b according to the modification 1-2b. FIG. 19 is a flowchart showing a concrete example of image data selecting process in step S130-2b in FIG. 18 and showing a schematic operation example of the synchronizing and selecting unit 154h according to the modification 1-2b.

In the modification 1-2b, first, the display device 150-2b executes operations similar to those in steps S121 to S126 in FIG. 8 to divide the image to image having the camera ID=1 and image data having the camera ID=2 (refer to steps S121 to S126 in FIG. 18). Subsequently, the scene change determining unit 154e determines image data in which a scene change occurs on the basis of image process results on successive image data in image data input from the image data input unit 154a (step S129-2b). A scene change determination result is input to the synchronizing and selecting unit 154h.

The synchronizing and selecting unit 154h executes a synchronization selecting process of selecting image data having the camera ID=1 and selecting image data having the camera ID=2 synchronized with the selected image data having the camera ID=1 on the basis of a scene change determination result input from the scene change determining unit 154e (step S130-2b). The details of the synchronization selecting process will be described later with reference to FIG. 19.

Next, the synchronizing and selecting unit 154h determines whether camera ID=1 is designated in step S123 (for example, whether the camera ID requested to generate an overview screen instructed to be displayed from the input unit 156 by the observer is "1") (step S131-2b). In the case where camera ID=1 is designated (Yes at step S131-2b), image data selected to have the camera ID=1 is selected (step S132-2b). On the other hand, in the case where the designated camera ID is not "1" (No at step S131-2b), that is, the camera ID=2 is selected, the image data input unit 154a selects the selected image data having the camera ID=2 (step S133-2b). The image data selected in steps S132-2b and S133-2b is input to the average color bar generating unit 154d and the screen generating unit 154f, respectively.

The average color bar generating unit 154d to which the selected image data is input calculates an average color of each image data (or each of regions obtained by dividing the image data) (step S134-2b) and, on the basis of the calculation result, generates the average color bars 15A and 15B obtained by connecting images of average colors in time series of the image data (step S135-2b). The generated average color bars 15A and 15B are input to the screen generating unit 154f.

The screen generating unit 154f generates the overview screens 10A-2b and 10B-2b shown in FIG. 16 from the selected image data supplied and the images of the average color bars 15A and 15B (step S136-2b) and outputs them to the display unit 155 via the control unit 151 (step S137-2b). The overview screens 10A-2a and 10B-2a as GUI screens are displayed on the display unit 155, and the GUI function using them is provided to the observer.

After that, the display device 150 determines whether the operation is continued, for example, whether an operation end instruction is supplied from the input unit 156 (step S138-2b). In the case of continuing the operation (Yes at step S138-2b), the display device 150-2b returns to step S123 and waits for the next designation of a camera ID. On the other hand, in the case where the operation is not continued (No at step S138-2b), the operation is finished.

In the synchronization selecting process in step S130-2b in FIG. 18, the synchronizing and selecting unit 154h in the image processing unit 154-2b receives image data from the image data input unit 154a (step S141-2b) and receives a scene change determination result from the scene change determining unit 154e (step S143-2b).

Next, for example, on the basis of the supplied scene change determination result, the synchronizing and selecting unit 154h specifies the camera ID of the imaging unit directed opposite to the travel direction of the capsule medical device 100 (step S144-2b). The synchronizing and selecting unit 154h extracts image data having the camera ID specified in step S144-2b from image data input from the image data input unit 154a (step S145-2b) and divides the image data scene by scene on the basis of the scene change determination result (step S146-2b). Subsequently, the synchronizing and selecting unit 154h adds the travel time "t" which is pre-set for each scene to the imaging time indicated by the time stamp of the image data divided scene by scene and associates the resultant time as updated imaging time information with the image data (step S147-2b). Image data associated with the updated imaging time information is stored together with image data which is not to be updated (that is, image data to which the camera ID of the imaging unit directed in the travel direction of the capsule medical device 100 is added) into, for example, the memory unit 153 and the like.

The synchronizing and selecting unit 154h reads the image data stored in the memory unit 153 and the like and selects the image data of the camera ID=1 from the image data on the basis of the image process result (step S148-2b). Subsequently, the synchronizing and selecting unit 154h sequentially selects the image data having the camera ID=1 selected in time series in accordance with the imaging time indicated by the time stamps (step S149-2b) and specifies and selects image data having the camera ID=2 synchronized with the selected image data having the camera ID=1 from the image data or the like stored in the memory unit 153 or the like (step S150-2b). That is, the synchronizing and selecting unit 154h according to the modification 1-2b selects image data to be displayed on the basis of image process results of successive image data in a series of image data having one of the camera IDs (step S148-2b) and selects image data having the other camera ID generated by capturing an image of the same position as the image data having the selected camera ID from a different direction (step S150-2b).

Next, the synchronizing and selecting unit 154h determines whether all of image data having the camera ID=1 selected in step S149-2b has been selected (step S151-2b). In the case where all of the image data has not been selected (No at step S151-2b), the synchronizing and selecting unit 154h returns to step S149-2b and selects the next image data having the camera ID=1.

On the other hand, in the case where all of image data having the camera ID=1 selected in step S149-2b has been selected (Yes at step S151-2b), the synchronizing and selecting unit 154h outputs synchronized image data to the screen generating unit 154f (step S152-2b) and returns to the operation in FIG. 18.

As described above, in the modification 1-2b, in addition to effects similar to those of the first embodiment, image data obtained by capturing images of the same position by different eyes can be displayed while being synchronized. Therefore, the observer can easily observe the region in the subject 900 from a plurality of angles.

Figure 20:
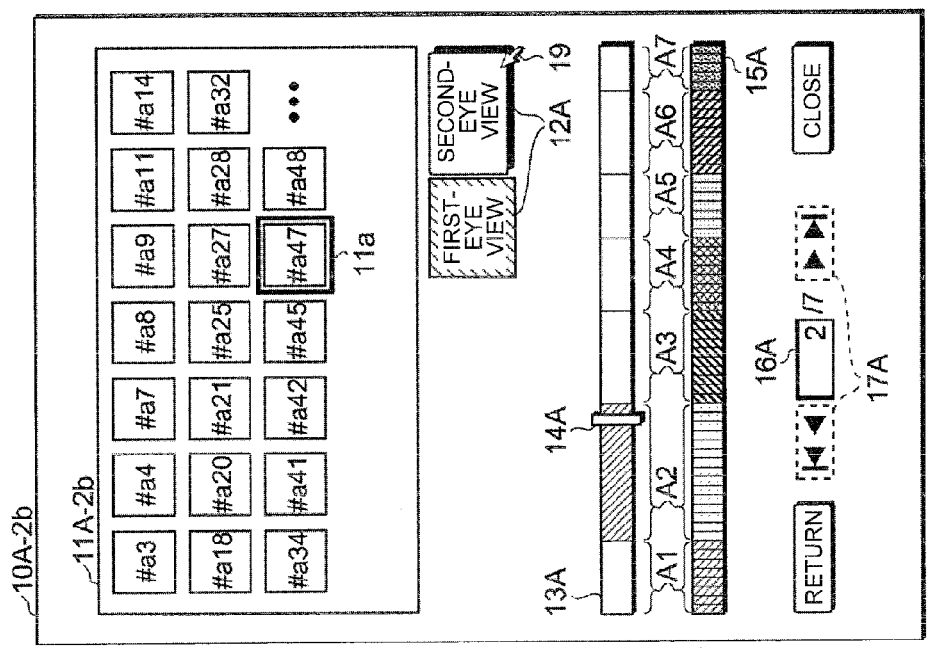
FIG. 20 is a diagram showing another example of an overview screen according to the modification 1-2b of the first embodiment of the invention.

In the modification 1-2b, for convenience of explanation, as image data as a reference at the time of selecting image data synchronized, selected image data having the camera ID=1 is used. However, the invention is not limited to the data. For example, selected image data having the camera ID=2 can be used as a reference. In this case, the overview screens 10A-2b and 10B-2b generated by the screen generating unit 154f (step S136-2b) are as shown in FIG. 20.

Modification 1-2c

Figure 21:
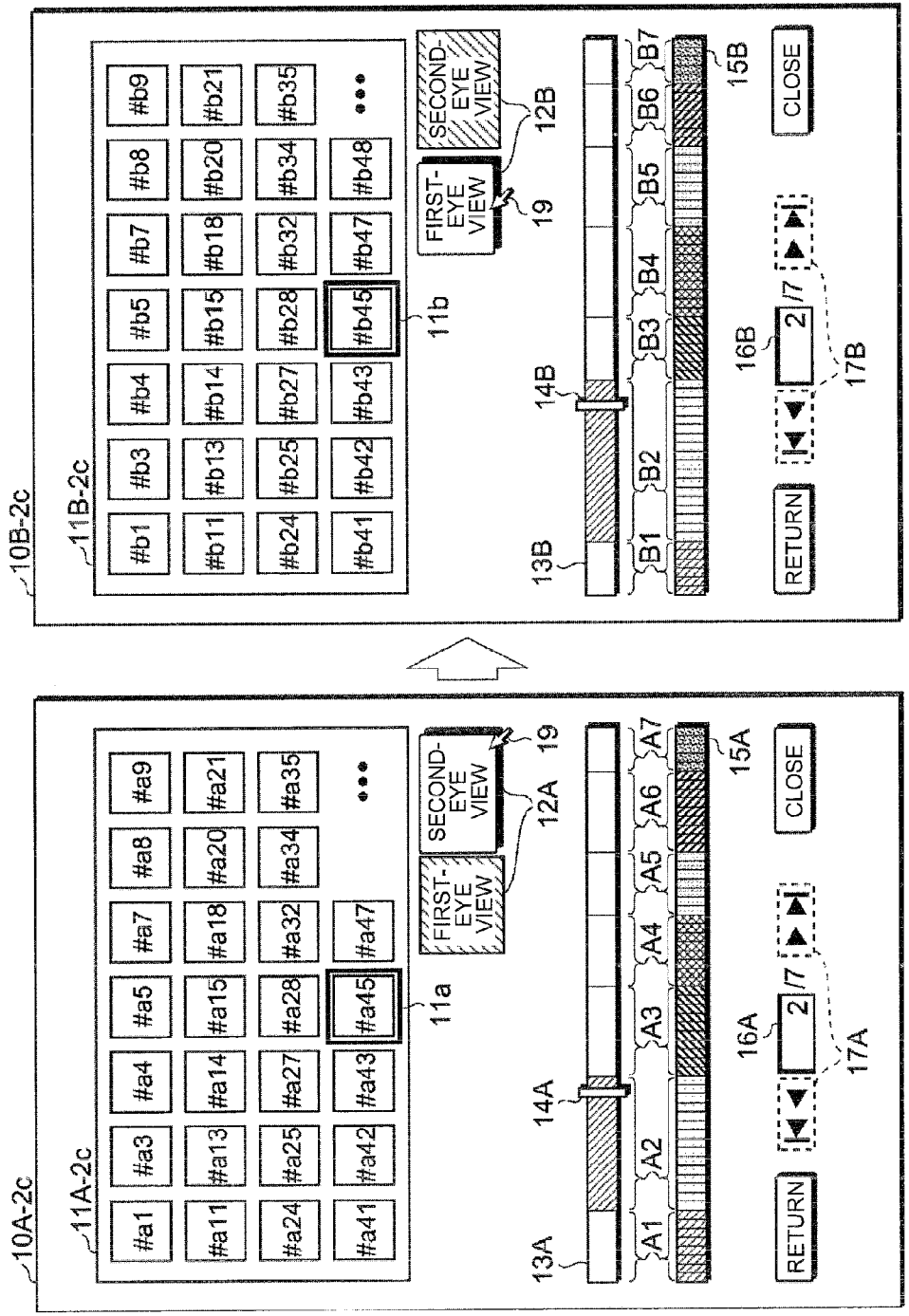
FIG. 21 is a diagram showing an example of an overview screen according to modification 1-2c of the first embodiment of the invention.

In the modification 1-2b, the case where one of image data (for example, selected image data having the camera ID=1) is used as a reference and the other image data (for example, image data having the camera ID=2) synchronized with the one of image data is selected without condition has been described. However, the invention is not limited to the case. For example, as shown in overview image display regions 11A-2c and 11B-2c in the overview screens 10A-2c and 10B-2c shown in FIG. 21, so-called logical sum (OR) is obtained between the selected image data having the camera ID=1 and the selected image data having the camera ID=2, and image data matching it may be selected. In the following, the case will be described in detail with reference to the drawings as the modification 1-2c of the first embodiment. In the following description, the same reference numerals are designated to components similar to those of the foregoing first embodiment and its modification, and repetitive description will not be repeated. FIG. 21 is a diagram showing an example of the overview screens 10A-2c and 10B-2c according to modification 1-2c.

Figure 22:
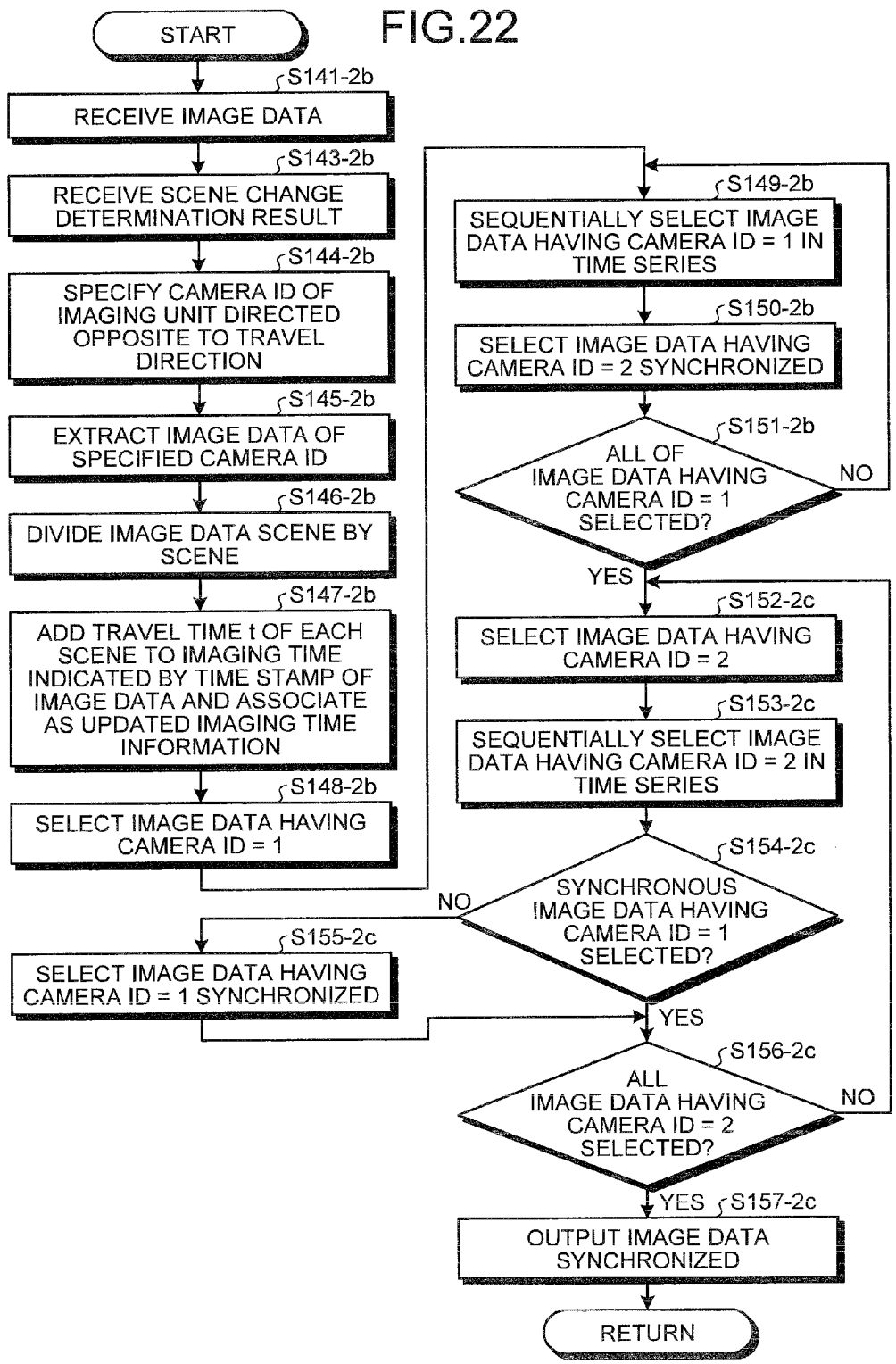
FIG. 22 is a flowchart showing a concrete example of synchronization selecting process according to the modification 1-2c of the first embodiment of the invention.

In the modification 1-2c, a configuration similar to that of the display device 150-2b shown in FIG. 17 and an operation similar to that of the display device 150-2b shown in FIG. 18 can be applied. The operation of the synchronizing and selecting unit 154h according to the modification 1-2c, that is, the flow of the synchronization selecting process in step S130-2b in FIG. 18 is as shown in FIG. 22. FIG. 22 is a flowchart showing a concrete example of the synchronization selecting process according to the modification 1-2c.

In the modification 1-2c, in the synchronization selecting process in step S130-2b in FIG. 18, the synchronizing and selecting unit 154h in the image processing unit 154-2b executes operations similar to those in steps S141-2b to S151-2b in FIG. 19 to select image data having the camera ID=2 synchronized with selected image data having the camera ID=1 from all of image data having the camera ID=2 (refer to steps S141-2b to S151-2b in FIG. 22).

Subsequently, the synchronizing and selecting unit 154h selects the image data having the camera ID=2 in image data stored in the memory unit 153 or the like on the basis of the image process result (step S152-2c). The synchronizing and selecting unit 154h sequentially selects the selected image data having the camera ID=2 in time series in accordance with the imaging time indicated by the time stamps or updated imaging time information (step S153-2c), determines whether image data having the camera ID=1 synchronized with the selected image data having the camera ID=2 has been selected in step S148-2b (step S154-2c) and, in the case where the image data has been selected (Yes at step S154-2c), moves to step S156-2c.

On the other hand, in the case where it is determined in step S154-2c that image data having the camera ID=1 synchronized has not been selected (No at step S154-2c), the synchronizing and selecting unit 154h specifies image data having the camera ID=1 synchronized with image data having the camera ID=2 as an object from image data or the like stored in the memory unit 153 or the like and adds it to selected image data (step S155-2c). That is, in the case where the synchronizing and selecting unit 154h according to the modification 1-2c selects image data to be displayed on the basis of image process results of successive image data in a series of image data by camera IDs (steps S148-2b and S152-2c) and image data having the other camera ID to be synchronized with image data having one of the camera IDs is not selected, the image data synchronized with the image data having one of the camera IDs in image data having the other camera ID which is not selected is selected as image data to be displayed (steps S150-2b and S155-2c).

Next, the synchronizing and selecting unit 154h determines whether all of image data having the camera ID=2 selected in step S152-2c has been selected (step S156-2c). In the case where all of the image data has not been selected (No at step S156-2c), the synchronizing and selecting unit 154h returns to step S152-2c and selects the next selected image data having the camera ID=2.

On the other hand, in the case where all of image data having the camera ID=2 selected in step S156-2b has been selected (Yes at step S156-2c), the synchronizing and selecting unit 154h outputs synchronized image data to the screen generating unit 154f (step S157-2c) and returns to the operation in FIG. 18.

As described above, in the modification 1-2c, in addition to effects similar to those of the first embodiment, image data obtained by capturing images of the same position by different eyes can be displayed while being synchronized. Therefore, the observer can easily observe the region in the subject 900 from a plurality of angles.

Modification 1-2d

Figure 23:
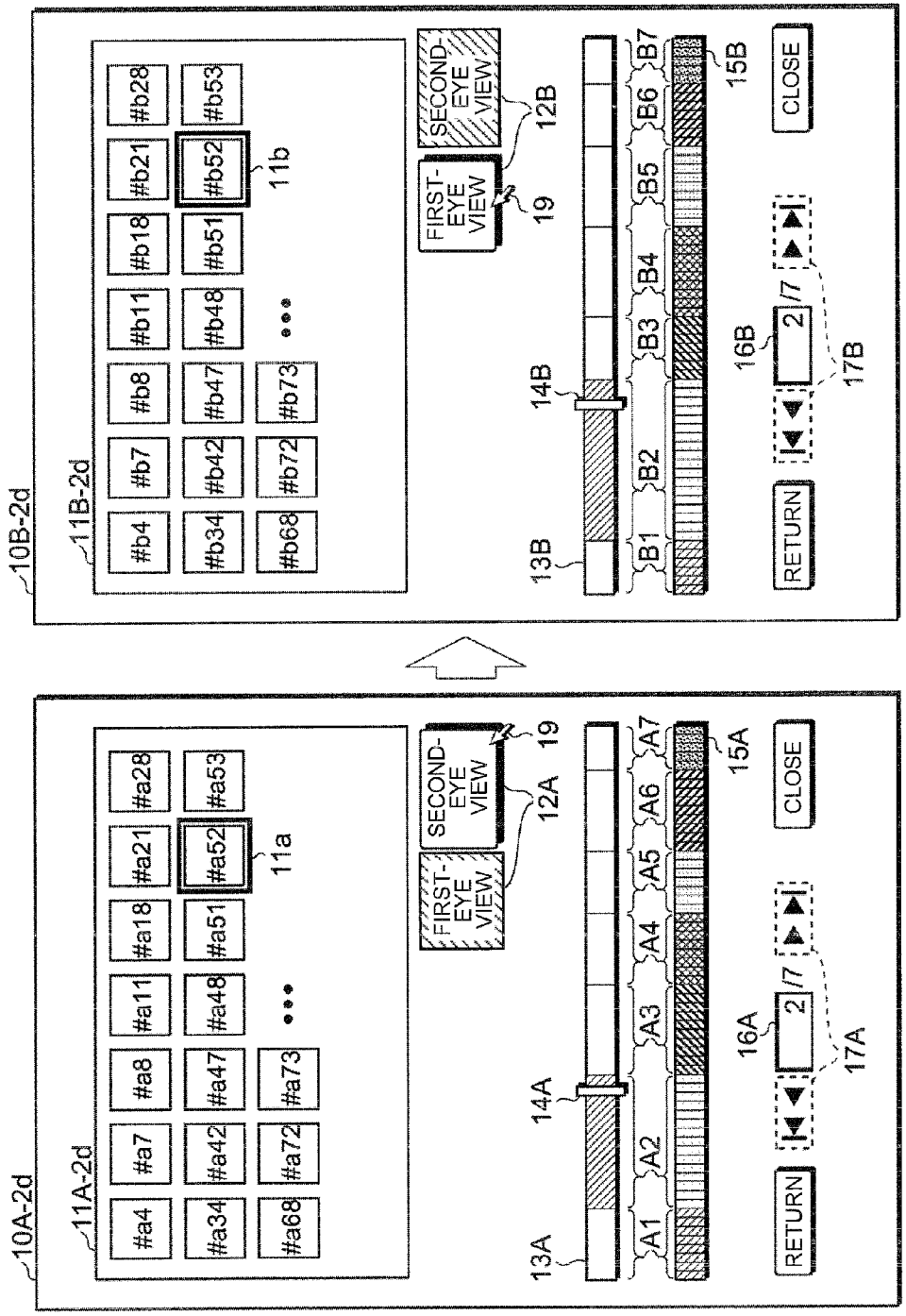
FIG. 23 is a diagram showing an example of an overview screen according to the modification 1-2 of the first embodiment of the invention.

Although image data is selected by calculating logical sum (OR) in the modification 1-2c, the invention is not limited to the case. For example, as shown in overview image display regions 11A-2d and 11B-2d in the overview screens 10A-2d and 10B-2d shown in FIG. 23, image data may be selected by calculating logical product (AND). In the following, the case will be described in detail with reference to the drawings as the modification 1-2d of the first embodiment. In the following description, the same reference numerals are designated to components similar to those of the foregoing first embodiment and its modification, and repetitive description will not be repeated. FIG. 23 is a diagram showing an example of the overview screens 10A-2d and 10B-2d according to modification 1-2d.

Figure 24:
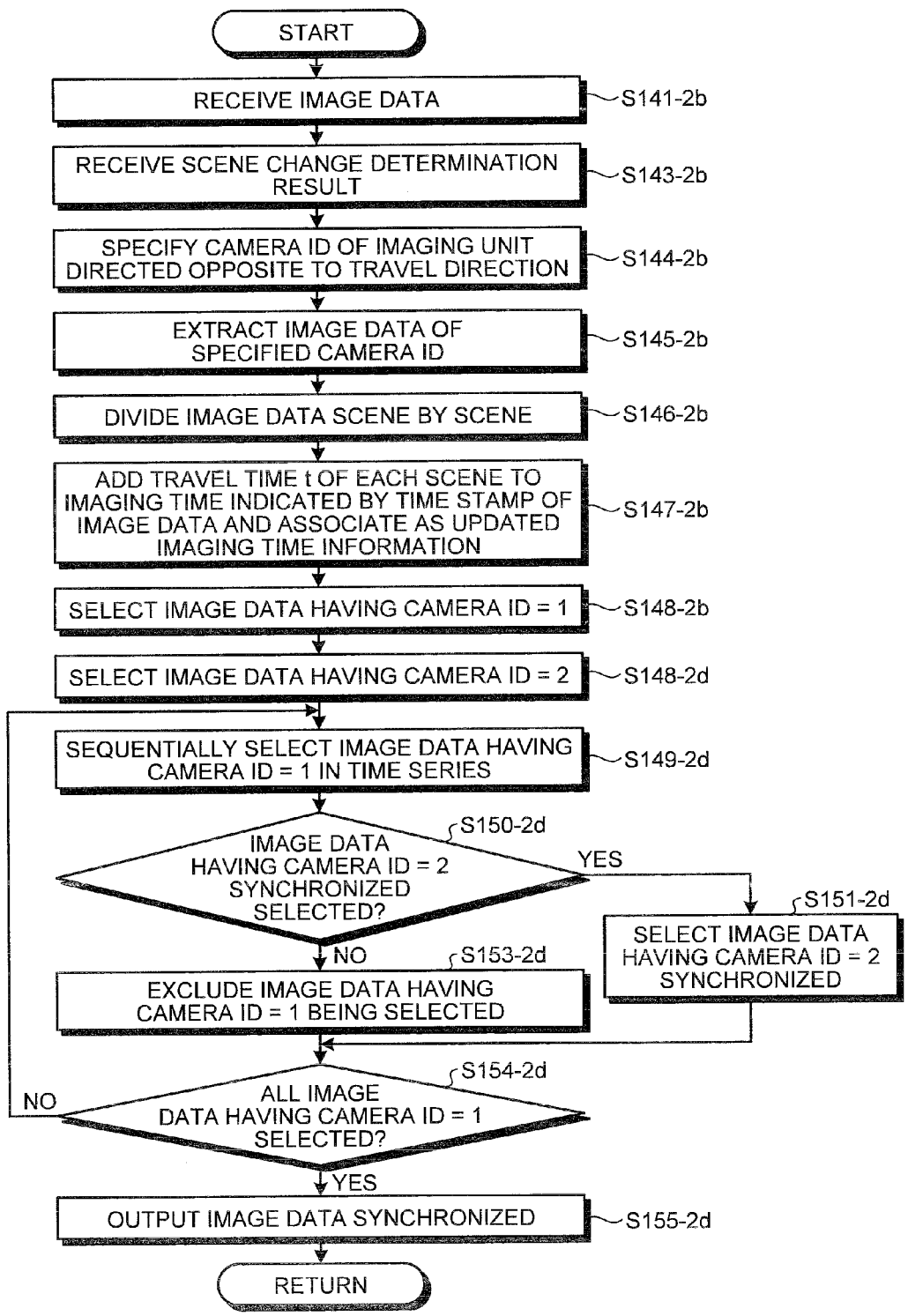
FIG. 24 is a flowchart showing a concrete example of the synchronization selecting process according to modification 1-2 of the first embodiment of the invention.

In the modification 1-2d, a configuration similar to that of the display device 150-2b shown in FIG. 17 and an operation similar to that of the display device 150-2b shown in FIG. 18 can be applied. The operation of the synchronizing and selecting unit 154h according to the modification 1-2d, that is, the flow of the synchronization selecting process in step S130-2b in FIG. 18 is as shown in FIG. 24. FIG. 24 is a flowchart showing a concrete example of the synchronization selecting process according to the modification 1-2d.

In the modification 1-2d, in the synchronization selecting process in step S130-2b in FIG. 18, the synchronizing and selecting unit 154h in the image processing unit 154-2b executes operations similar to those in steps S141-2b to S148-2b in FIG. 19 to select image data having the camera ID=1 (refer to steps S141-2b to S148-2b in FIG. 24).

Subsequently, the synchronizing and selecting unit 154h selects the image data having the camera ID=2 in image data stored in the memory unit 153 or the like on the basis of the image process result (step S148-2d).

The synchronizing and selecting unit 154h sequentially selects the image data selected in step S148-2b and having the camera ID=1 in time series in accordance with the imaging time indicated by the time stamps (step S149-2d). Subsequently, the synchronizing and selecting unit 154h determines whether image data having the camera ID=2 synchronized with the selected image data having the camera ID=1 is selected in step S148-2d (step S150-2d) and, in the case where the image data has been selected (Yes at step S150-2d), selects the image data having the camera ID=2 (step S151-2d). On the other hand, in the case where the synchronized image data having the camera ID=2 has not been selected (No at step S150-2d), the synchronizing and selecting unit 154h excludes the image data having the camera ID=1 being selected from selected image data (step S153-2d). That is, the synchronizing and selecting unit 154h according to the modification 1-2d selects image data to be displayed on the basis of image process results of successive image data in a series of image data by camera IDs (steps S148-2b and S148-2d) and, in the case where image data having the other camera ID to be synchronized with image data having one of the camera IDs is not selected, excludes the image data having the one of the camera IDs from image data to be displayed (step S153-2d).

Next, the synchronizing and selecting unit 154h determines whether all of image data having the camera ID=1 selected in step S149-2d has been selected (step S154-2d). In the case where all of the image data has not been selected (No at step S154-2d), the synchronizing and selecting unit 154h returns to step S149-2d and selects the next selected image data having the camera ID=1.

On the other hand, in the case where all of image data having the camera ID=1 selected in step S154-2d has been selected (Yes at step S154-2d), the synchronizing and selecting unit 154h outputs synchronized image data to the screen generating unit 154f (step S155-2d) and returns to the operation in FIG. 18.

As described above, in the modification 1-2d, in addition to effects similar to those of the first embodiment, image data obtained by capturing images of the same position by different eyes can be displayed while being synchronized. Therefore, the observer can easily observe the region in the subject 900 from a plurality of angles.

Modification 1-3

In the first embodiment and its modifications, it may be constructed that the observer can arbitrarily rotate each of reduced images in an overview image display region (for example, the overview image display region 11A). In the following, this case will be described as modification 1-3 of the first embodiment with reference to the drawings. In the following, for convenience of explanation, the modification 1-3 will be described using the first embodiment as the base. However, the invention is not limited to the case. Obviously, the modification 1-3 can be applied to the first embodiment and any of the modifications of the first embodiment. Further, in the following, an overview screen 10A-3 displaying a list of reduced images of image data having the camera ID=1 will be described as an example. Obviously, the invention can be also applied to an overview screen displaying a list of reduced images of image data having the camera ID=2.

FIG. 25 is a diagram showing an example of the overview screen 10A-3 according to the modification 1-3. FIG. 25(a) shows an example of the overview screen 10A-3 before a reduced image is rotated, and FIG. 25(b) shows an example of the overview screen 10A-3 after the reduced image is rotated.

As shown in FIG. 25(a), for example, when the observer operates the pointer 19 with the mouse or the like of the input unit 156 to single-click a reduced image #A1 in an overview image display region 11A-3, the target reduced image #A1 is selected, and the selection frame 11a is added to the reduced image #A1. For example, when the observer operates the pointer 19 with the mouse or the like of the input unit 156 to double-click the reduced image #A1, as shown in FIG. 25(b), the target reduced image #A1 is turned by predetermined angle (for example, 30° or 90°) in a predetermined direction (for example, in a clockwise direction).

By dragging a corner of a reduced image in a desired rotation direction with the pointer 19, the target reduced image may be turned by arbitrary turn angle in an arbitrary turn direction.

As described above, the overview screen 10A-3 and the input unit 156 function as turn instruction input means with which an instruction to turn image data (reduced images) displayed in a list is input, and the screen generating unit 154f functions as turn correcting means that corrects turn of the image data instructed to turn.

Since the imaging process of turning each reduced image can be easily realized by the screen generating unit 154f in the image processing unit 154 in FIG. 4, the detailed description will not be given here.

Modification 1-4

In the first embodiment and its modifications, it may be constructed that the observer can arbitrarily change the size of the overview image display region and/or the number of reduced images displayed in a list in the overview image display region. In the following, this case will be described as modification 1-4 of the first embodiment with reference to the drawings. In the following, for convenience of explanation, the modification 1-4 will be described using the first embodiment as the base. However, the invention is not limited to the case. Obviously, the modification 1-4 can be applied to the first embodiment and any of the modifications of the first embodiment. Further, in the following, an overview screen 10A-4 displaying a list of reduced images of image data having the camera ID=1 will be described as an example. Obviously, the invention can be also applied to an overview screen displaying a list of reduced images of image data having the camera ID=2.

FIG. 26 is a diagram showing an example of the overview screen 10A-4 according to the modification 1-4. FIG. 26(*a*) shows an example of the overview screen 10A-4 before the reduced image is rotated, and FIG. 26(*b*) shows an example of the overview screen 10A-4 after the reduced image is rotated.

As shown in FIG. 26(*a*), for example, when the observer operates the pointer 19 with the mouse or the like of the input unit 156 to drag an edge portion of an overview image display region 11A-4, the display range of the overview image display region 11A-4 changes according to movement of the pointer 19 as shown in FIG. 26(*b*). When the size of each reduced image is fixed, the number of reduced images displayed in a list changes according to the size of the overview image display region 11A-4. For example, in the case of displaying reduced images in the same scene so as to be divided into a plurality of pages, the total number of pages of each scene increases/decreases according to a change in the number of reduced images which can be displayed in the overview image display region 11A-4.

Since a change in the size of the overview image display region 11A-4, automatic adjustment of the number of reduced images displayed in the region, and automatic increase/decrease in the total number of pages can be easily realized by the screen generating unit 154f in the image processing unit 154 in FIG. 4, the detailed description will not be given here.

Modification 1-5

In the first embodiment and its modifications, reduced images of image data having the camera ID=1 and reduced images of image data having the camera ID=2 are displayed in different GUI screens (for example, in the first embodiment, the overview screens 10A and 10B). The invention is not limited to the case. For example, as shown in an overview screen 10-5 according to modification 1-5 of the first embodiment shown in FIG. 27, an overview image display region 11A displaying a list of reduced images of image data having the camera ID=1 and an overview image display region 11B displaying a list of reduced images of image data having the camera ID=2 may be displayed side by side in the single overview screen 10-5. In the following, for convenience of explanation, the modification 1-5 will be described using the first embodiment as the base. However, the invention is not limited to the case. Obviously, the modification 1-5 can be applied to the first embodiment and any of the modifications of the first embodiment.

Figure 27:
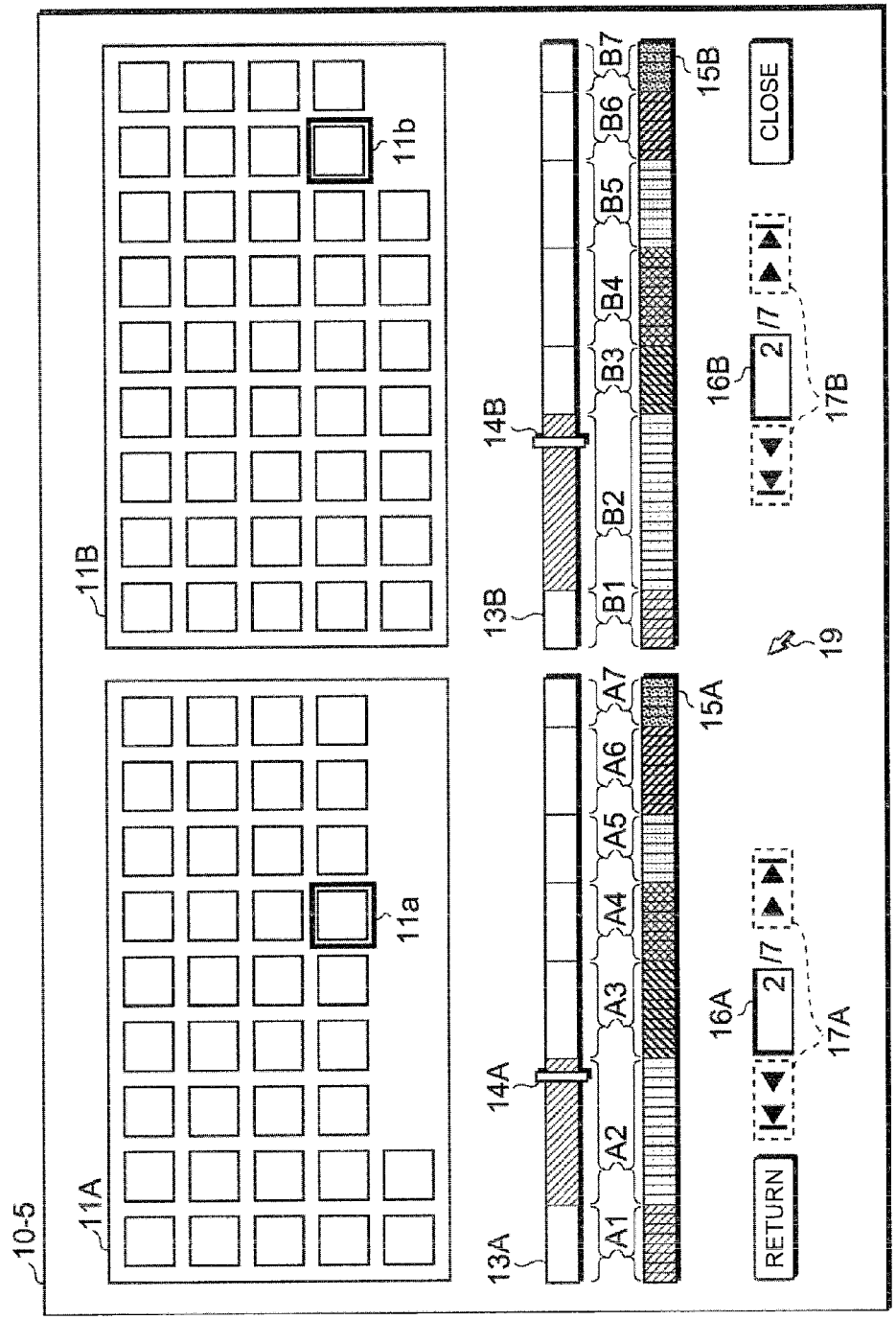
FIG. 27 is a diagram showing an example of an overview screen according to the modification 1-5 of the first embodiment of the invention.

In the example of the overview screen 10-5 shown in FIG. 27, the overview image display regions 11A and 11B are arranged in the lateral direction, and the time scale bars 13A and 13B, the sliders 14A and 14B, the average color bars 15A and 15B, the display scene boxes 16A and 16B, and the scene switching buttons 17A and 17B are disposed below the regions 11A and 11B, respectively.

Since generation of such an overview screen 10-5 can be easily reached from the foregoing first embodiment or its modification, detailed description will not be given here.

Modification 1-6

In the modification 1-5, the overview image display regions 11A and 11B are arranged side by side. The invention is not limited to the arrangement. For example, as shown in an overview screen 10-6 according to modification 1-6 of the first embodiment shown in FIG. 28, the overview image display region 11A displaying a list of reduced images of image data having the camera ID=1 and the overview image display region 11B displaying a list of reduced images of image data having the camera ID=2 may be displayed in tandem. In the following, for convenience of explanation, the modification 1-6 will be described using the first embodiment as the base. However, the invention is not limited to the case. Obviously, the modification 1-6 can be applied to the first embodiment and any of the modifications of the first embodiment.

Figure 28:
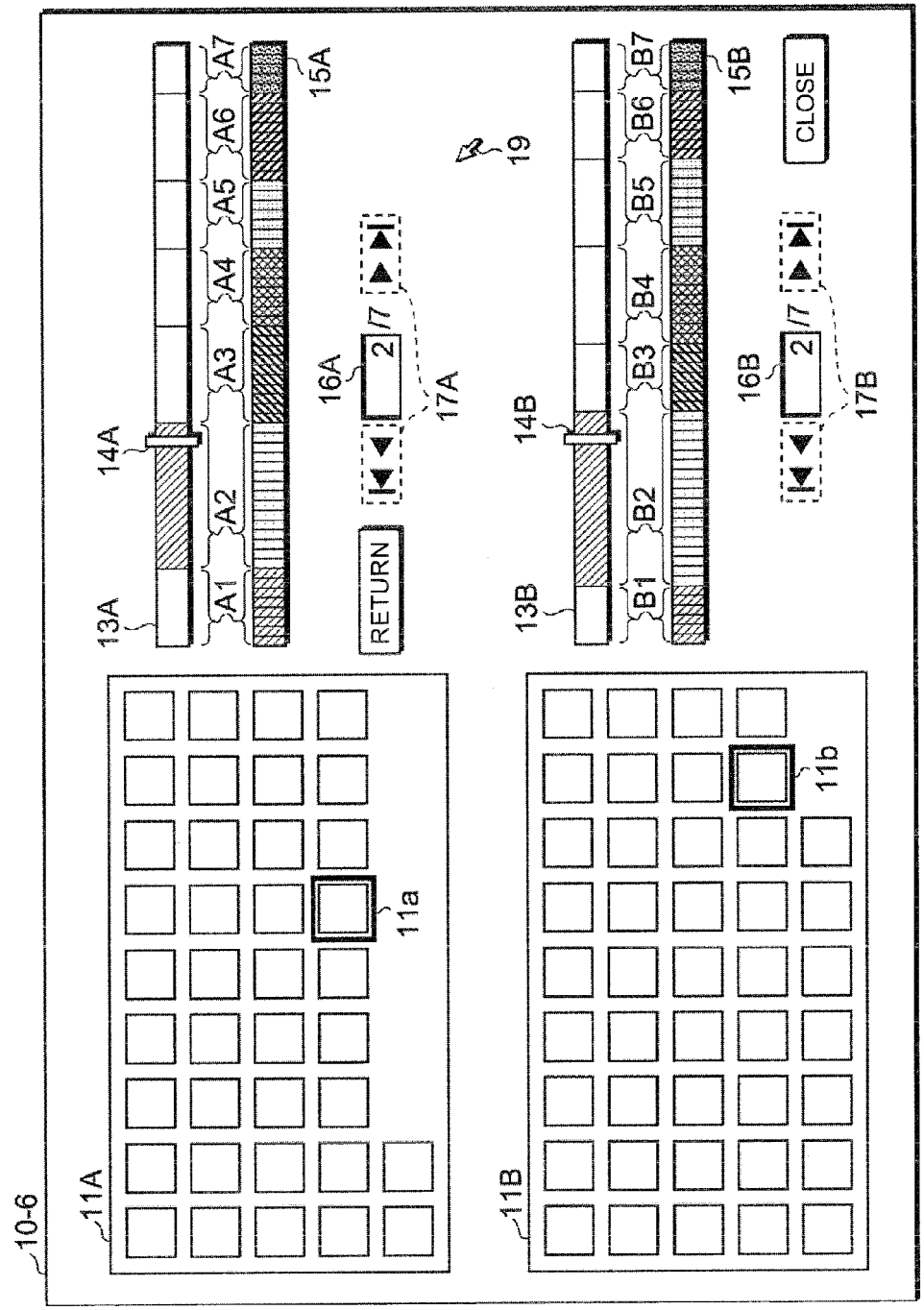
FIG. 28 is a diagram showing an example of an overview screen according to the modification 1-6 of the first embodiment of the invention.

In the example of the overview screen 10-6 shown in FIG. 28, the overview image display regions 11A and 11B are arranged in the vertical direction, and the time scale bars 13A and 13B, the sliders 14A and 14B, the average color bars 15A and 15B, the display scene boxes 16A and 16B, and the scene switching buttons 17A and 17B are disposed on a side (for example, the right side) of the regions 11A and 11B, respectively.

Since generation of such an overview screen 10-6 can be easily reached from the foregoing first embodiment or its modification, detailed description will not be given here.

Modification 1-7

In the modification 1-5, the time scale bars 13A and 13B, the sliders 14A and 14B, and the average color bars 15A and 15B corresponding to the overview image display regions 11A and 11B are disposed in regions below the regions 11A and 11B, respectively. That is, the time scale bar 13A and the slider 14A and the time scale bar 13B and the slider 14B are displayed side by side, and the average color bars 15A and 15B are displayed side by side. The invention is not limited to the arrangement. For example, as shown in an overview screen 10-7 according to modification 1-7 of the first embodiment shown in FIG. 29, the time scale bar 13A and the slider 14A, the time scale bar 13B and the slider 14B, and the average color bars 15A and 15B may be displayed in tandem. In the following, for convenience of explanation, the modification 1-7 will be described using the first embodiment as the base. However, the invention is not limited to the case. Obviously, the modification 1-7 can be applied to the first embodiment and any of the modifications of the first embodiment.

Figure 29:
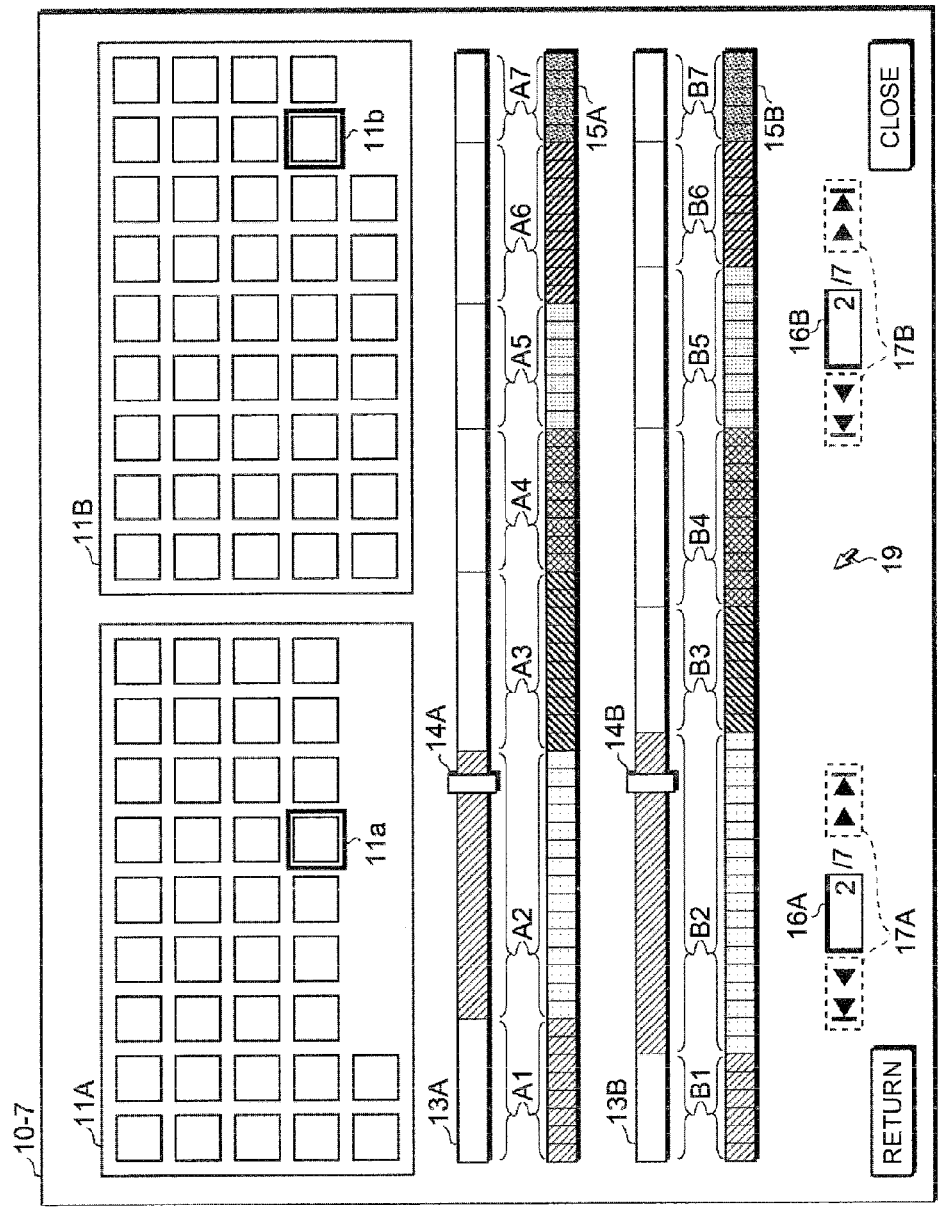
FIG. 29 is a diagram showing an example of an overview screen according to the modification 1-7 of the first embodiment of the invention.

In the example of the overview screen 10-7 shown in FIG. 29, the overview image display regions 11A and 11B are arranged in the lateral direction, and the time scale bar 13A and the slider 14A, the time scale bar 13B and the slider 14B, and the average color bars 15A and 15B are disposed in tandem.

Since generation of such an overview screen 10-7 can be easily reached from the foregoing first embodiment or its modification, detailed description will not be given here.

Modification 1-8

In the modifications 1-2a to 1-2d, the case of synchronizing the image data having the camera ID=1 and the image data having the camera ID=2 by using the travel time "t" which is preset on the basis of the travel speed in the lumen 902 of the capsule medical device 100 has been described as an example. The method of synchronizing the image data is not limited to the above. For example, it is also possible to synchronize image data of the same position and synchronize image data using the image data as a start point. In the following, the case will be described with reference to the drawings as modification 1-8 of the first embodiment. In the following, for convenience of explanation, the modification 1-8 will be described using the first embodiment as the base. However, the invention is not limited to the case. Obviously, the modification 1-8 can be applied to the first embodiment and any of the modifications of the first embodiment.

Figure 30:
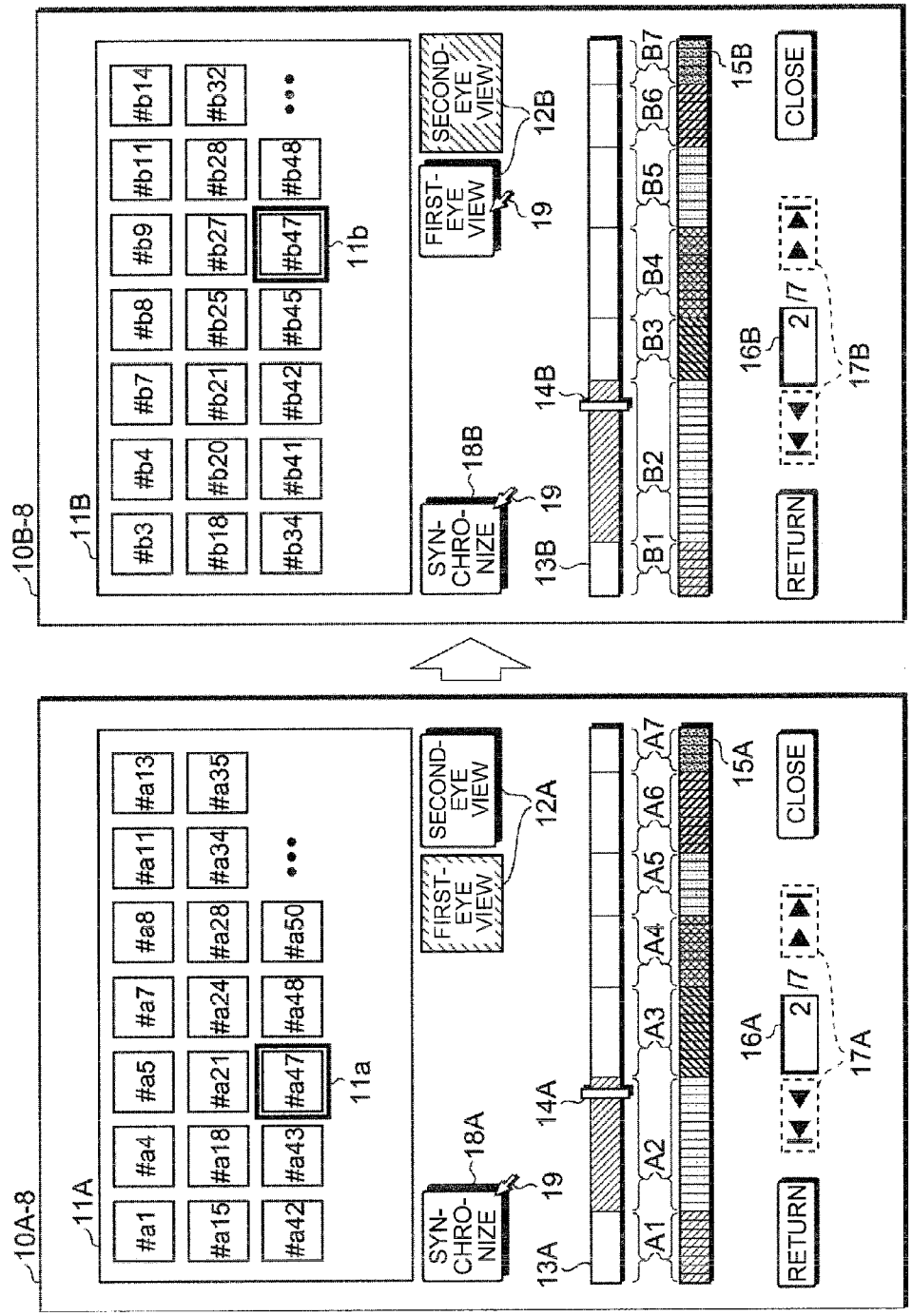
FIG. 30 is a diagram showing an example of an overview screen before synchronization according to the modification 1-8 of the first embodiment of the invention.
Figure 31:
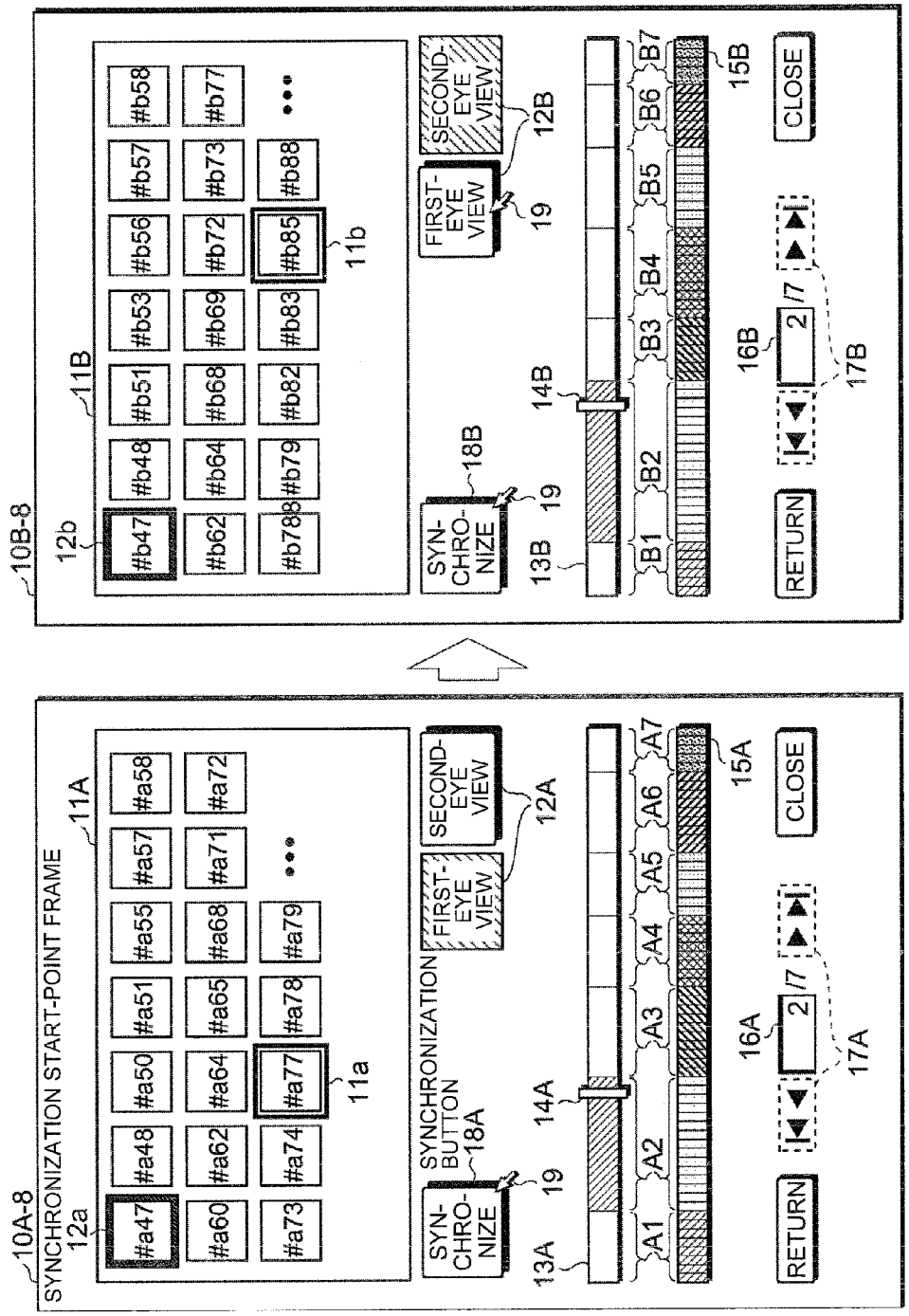
FIG. 31 is a diagram showing an example of an overview screen after synchronization according to the modification 1-8 of the first embodiment of the invention.

FIG. 30 is a diagram showing an example of overview screens 10A-8 and 10B-8 before synchronization according to the modification 1-8. FIG. 31 is a diagram showing an example of the overview screens 10A-8 and 10B-8 after synchronization according to the modification 1-8.

As shown in FIG. 30, the overview screens 10A-8 and 10B-8 are provided with synchronization buttons 18A and 18B, respectively, as GUI used by the observer to input an image data synchronization instruction. The observer operates the pointer 19 by using the mouse or the like of the input unit 156 and clicks the synchronization button 18A or 18B in a state where any of reduced images in the overview image display region 11A or 11B is selected. As shown in FIG. 31, using image data as generation sources of the reduced images in the selected state (in the example shown in FIGS. 30 and 31, image data #a47 or #b47) as the start points of synchronization, the image data having the camera ID=1 and the image data having the camera ID=2 is synchronized, and reduced images are displayed in the overview image display regions 11A or 11B in accordance with the order. The GUI function provided by the overview screens 10A-8 and 10B-8 and the input unit 156 is that of start-point image selecting means that allows the observer select image data as a start point of synchronization.

As shown in FIG. 31, synchronization start-point frames 12a and 12b for emphasis display may be added to reduced images of image data as a start point of synchronization (image data #a47 or #b47 in the example of FIGS. 30 and 31).

Since such a synchronizing process can be easily realized in the screen generating unit 154f in the image processing unit 154 in FIG. 4, the detailed description will not be repeated.

Second Embodiment

In the first embodiment and its modifications, the case where lists of reduced images of image data captured by different imaging units are displayed in different overview image display regions has been described as examples. The invention is not limited to the case. Reduced images of image data captured by different imaging units may be displayed in a single overview image display region. In the following, the case will be described in detail as a second embodiment with reference to the drawings.

A medical system according to the second embodiment may have a configuration similar to that of the medical system 1 according to the first embodiment. In the second embodiment, the display device 150 is replaced with a display device 250 shown in FIG. 32. In the following description, the same reference numerals are designated to components similar to those of the foregoing first embodiment and its modifications, and repetitive description will not be given.

Figure 32:
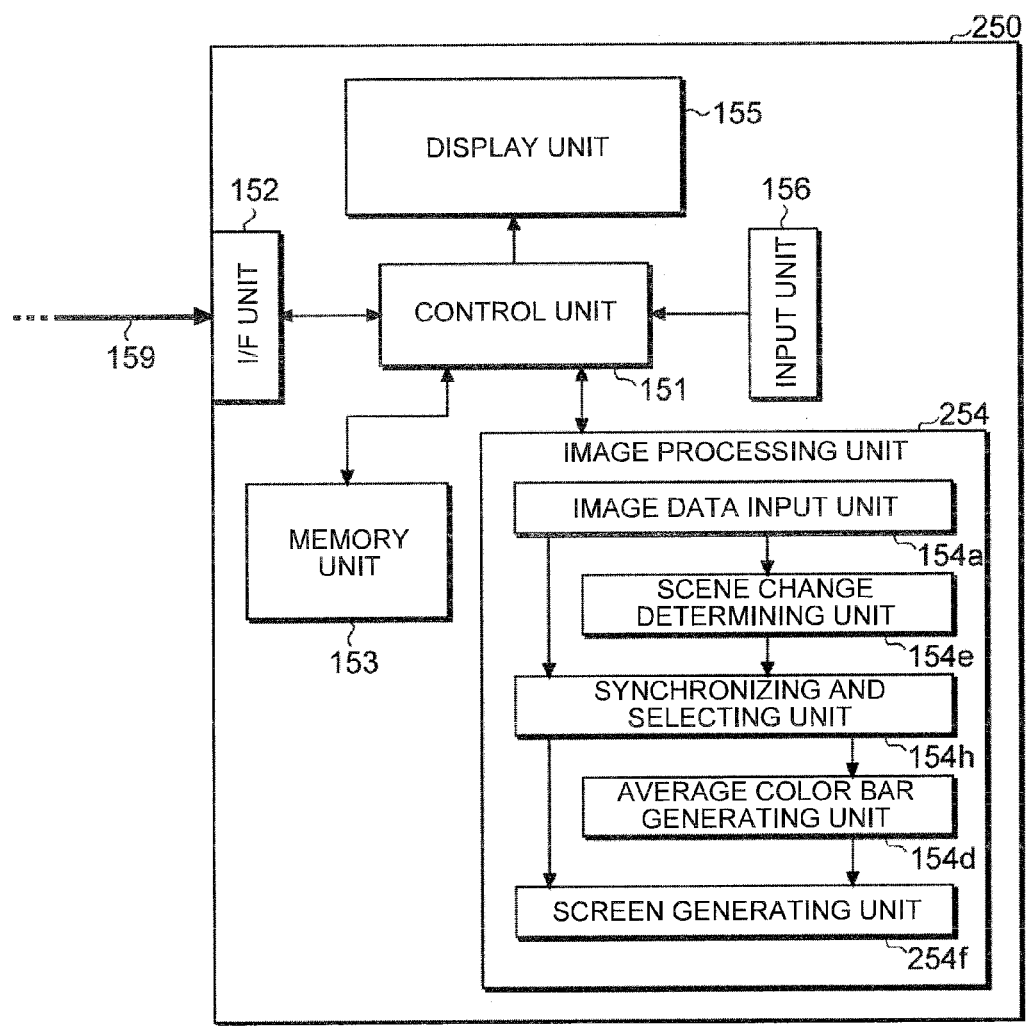
FIG. 32 is a block diagram showing an example of a schematic configuration of a display device according to a second embodiment of the invention.

FIG. 32 is a block diagram showing a schematic configuration example of the display device 250 according to the second embodiment. As illustrated in FIG. 32, in the display device 250, the image processing unit 154 shown in FIG. 4 is replaced with an image processing unit 254. The image processing unit 254 has a configuration similar to that of the image processing unit 150-2b (refer to FIG. 17) in the modification 1-2b except that the screen generating unit 154f is replaced with a screen generating unit 254f.

Figure 33:
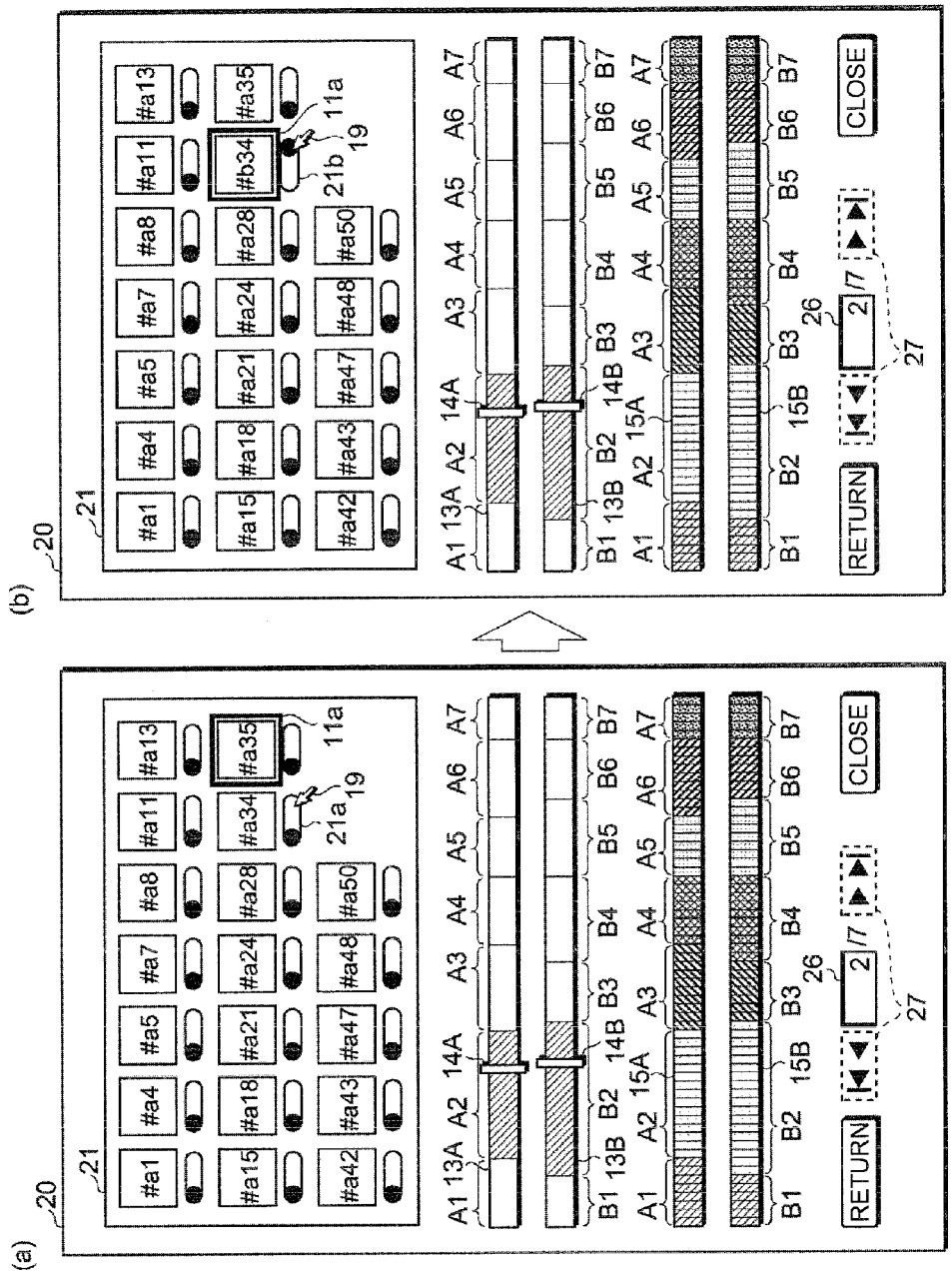
FIG. 33 is a diagram showing an example of an overview screen in the second embodiment of the invention.

The screen generating unit 254f generates an overview screen 20 as shown in FIG. 33 by using image data output and selected by the synchronizing and selecting unit 154h and the images of the average color bars 15A and 15B output from the average color bar generating unit 154d. FIG. 33 shows an example of the overview screen 20 according to the second embodiment. FIG. 33(a) shows the overview screen 20 before a reduced image is switched, and FIG. 33(b) shows the overview screen 20 after a reduced image is switched.

As shown in FIG. 33, the overview screen 20 according to the second embodiment includes an overview image display region 21 displaying a list of reduced images of selected image data, the time scale bar 13A, the slider 14A, and the average color bar 15A on image data having the camera ID=1, the time scale bar 13B, the slider 14B, and the average color bar 15B on image data having the camera ID=2, a display scene box 26 indicative of the order of a scene being displayed in the overview image display region 21 in all of scenes, and a scene switching button 27 for switching the scene to be displayed in the overview image display region 21.

In the overview image display region 21 in an initial state, for example, a list of reduced images (a part of #a1 to #a50) of the selected image data having the camera ID=1 is displayed. Near (for example, below) each reduced image, an image (hereinbelow, called capsule image) 21a/21b visually showing the imaging unit (101A or 101B) of the capsule medical device 100 which captured the reduced image is displayed. For convenience of explanation, it is assumed that the capsule image 21a indicates the imaging unit having the camera ID=1 (that is, the first imaging unit 101A), and the capsule image 21b indicates the imaging unit having the camera ID=2 (that is, the second imaging unit 101B). In display of the capsule images 21a and 21b, the shape, color, and the like may be changed by camera IDs.

When the observer operates the pointer 19 to click the capsule image 21a attached to a reduction image #a34 in the overview image display region 21 in FIG. 33(a), as shown in FIG. 33(b), a reduced image #b34 of image data having the camera ID=2 is displayed. That is, the reduced image corresponding to the clicked capsule image 21a or 21b is switched to the reduced image of the other camera ID.

Figure 34:
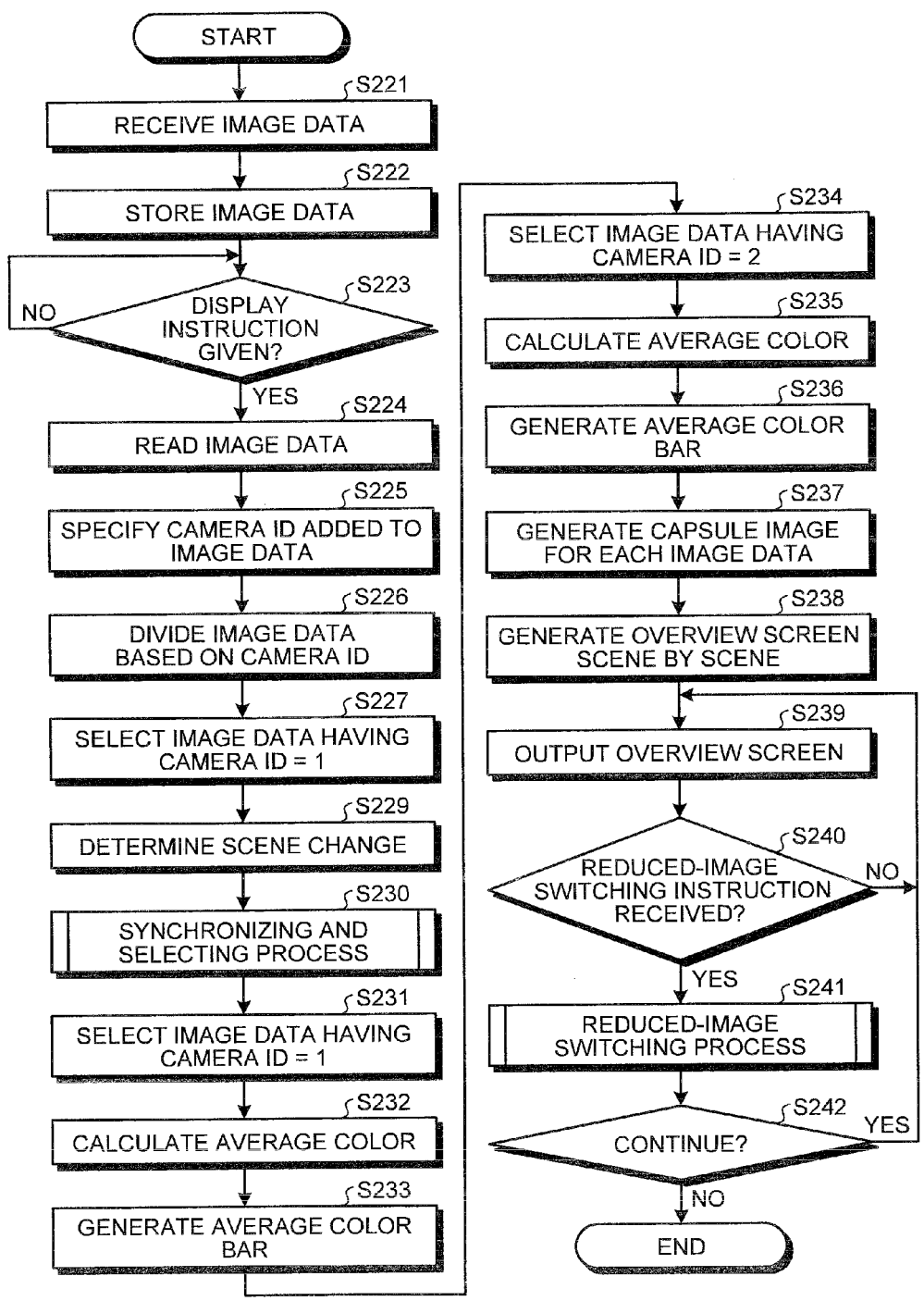
FIG. 34 is a flowchart showing an example of outline operation of the display device according to the second embodiment of the invention.
Figure 35:
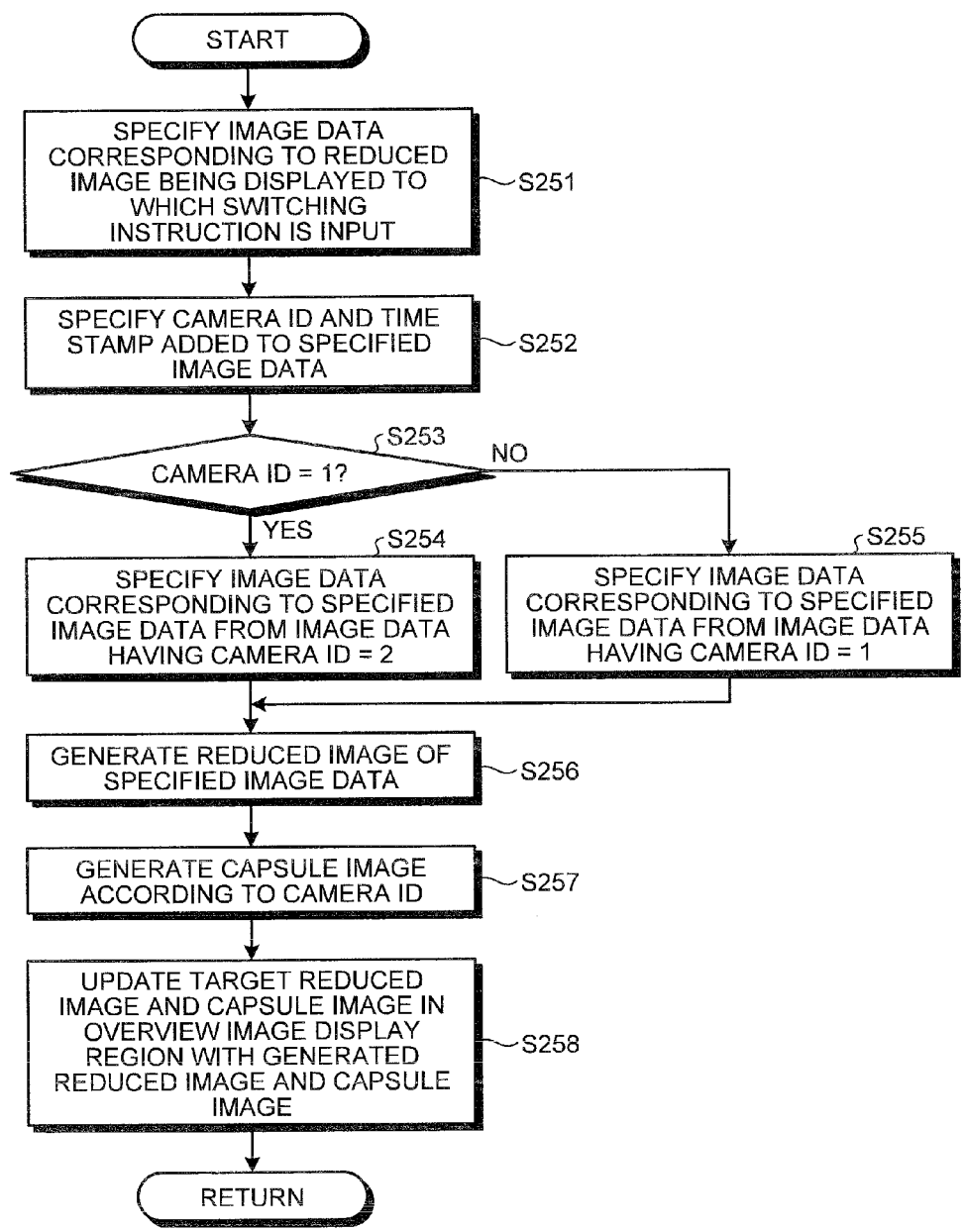
FIG. 35 is a flowchart showing a concrete example of reduced-image switching process in step S241 in FIG. 34.

The operation of the medical system according to the second embodiment will now be described in detail with reference to the drawings. Since the operation of the capsule medical device 100 and that of the receiving device 130 in the second embodiment are similar to those of the first embodiment (refer to FIGS. 6 and 7), the detailed description will not be repeated. FIG. 34 is a flowchart showing an example of schematic operation of the display device 250 according to the second embodiment. FIG. 35 is a flowchart showing a concrete example of reduced-image switching operation in step S241 in FIG. 34.

As shown in FIG. 34, the display device 250 according to the second embodiment receives image data from the interface unit 152 using the portable recording medium 140 or the communication cable 159 as a medium (step S221) and temporarily stores the image data in the memory unit 153 or the like via the control unit 151 (step S222).

Next, the display device 250 waits until a display instruction of the overview screen 20 is supplied from the input unit 156 or the like (No at step S223). In the case where a display instruction is received (Yes at step S223), the display device 250 reads image data stored in the memory unit 153 or the like (step S224). The read image data is supplied to the image data input unit 154a in the image processing unit 254.

The image data input unit 154a specifies each of the camera IDs added to the input image data (step S225) and divides the image data by imaging units (101A and 101B) on the basis of the camera IDs, that is, by camera IDs (step S226).

Next, the image data input unit 154a selects image data having the camera ID=1 (step S227). The selected image data having the camera ID=1 is input to the scene change determining unit 154e.

The scene change determining unit 154e determines image data in which a scene change occurs on the basis of image process results on successive image data in the image data having the camera ID=1 supplied from the image data input unit 154a (step S229). The scene change determination result is supplied to the synchronizing and selecting unit 154h.

On the basis of a scene change determination result supplied from the scene change determining unit 154e, the synchronizing and selecting unit 154h executes the synchronizing and selecting process for selecting image data while synchronizing the image data (step S230). The synchronizing and selecting process according to the second embodiment can be made similar to that shown in the modifications 1-2a to 1-2d of the first embodiment (refer to step S130-2b in FIG. 18, FIG. 19, 22, or 24). Image data selected in step S230 is input to the average color bar generating unit 154d and the screen generating unit 254f.

The average color bar generating unit 154d to which the selected image data is supplied selects image data having the camera ID=1 (step S231), calculates an average color of the selected image data (or each of regions obtained by dividing the image data) (step S232) and, on the basis of the calculation result, generates the average color bar 15A obtained by connecting images of average colors along time series of the image data (step S233). The generated average color bar 15A is supplied to the screen generating unit 254f.

Next, the average color bar generating unit 154d selects image data having the camera ID=2 (step S234), calculates an average color of the selected image data (or each of regions obtained by dividing the image data) (step S235) and, on the basis of the calculation result, generates the average color bar 15B obtained by connecting images of average colors along time series of the image data (step S236). The generated average color bar 15B is supplied to the screen generating unit 254f.

The screen generating unit 254f to which the images of the average color bars 15A and 15B and selected image data are supplied generates, first, for each of the image data supplied and selected, the capsule image 21a on the basis of the camera ID (step S237), generates the overview screen 20 for each scene as shown in FIG. 33(a) using the generated capsule image 21a, the selected image data having the camera ID=1, and the images of the average color bars 15A and 15B (step S238), and outputs the generated overview screen 20 to the display unit 155 (step S239). As a result, the overview screen 20 as a GUI screen is displayed on the display unit 155, and the GUI function using it is provided to the observer.

After that, the display device 250 determines whether an instruction of switching a reduced image displayed in the overview image display region 21 in the overview screen 20 is input by the observer using, for example, the mouse of the input unit 156 or the like (step S240). In the case where the instruction is input (Yes at step S240), the display device 250 executes a reduced-image switching process of switching the reduced image displayed in the overview image display region 21 (step S241). The details of the reduced-image switching process will be described later with reference to FIG. 35.

On the other hand, in the case where the reduced-image switching instruction is not input (No at step S240), the display device 250 determines whether the operation is continued, for example, whether an operation end instruction is received from the input unit 156 (step S242). In the case of continuing the operation (Yes at step S242), the display device 250 returns to step S239. On the other hand, in the case where the operation is not continued (No at step S242), the operation is finished.

In the reduced-image switching process in step S241 in FIG. 34, as shown in FIG. 35, first, the screen generating unit 254f in the display device 250 specifies image data from which the reduced image being displayed and instructed to be switched is generated (step S251) and, next, specifies the camera ID and the time stamp added to the specified image data (step S252).

Next, the screen generating unit 254f determines whether the specified camera ID is "1" (step S253). In the case where camera ID=1 (Yes at step S253), the screen generating unit 254f specifies image data having the camera ID=2 corresponding to the image data specified in step S251 from, for example, the memory unit 153 or the like (step S254). On the other hand, in the case where camera ID specified in step S252 is not "1", that is, is "2" (No at step S253), the screen generating unit 254f specifies image data having the camera ID=1 corresponding to the image data specified in step S251 from, for example, the memory unit 153 or the like (step S255).

The screen generating unit 254f generates a reduced image of the image data specified in step S254 or S255 (step S256) and generates a capsule image (for example, the capsule image 21a or 21b in FIG. 33) according to the camera ID of image data from which the reduced image is generated (step S257). That is, the overview screen 20, the input unit 156 that operates/inputs the overview screen 20, and the screen generating unit 254f function as switching means that individually switches the camera ID of image data to be displayed. The screen generating unit 254f switches image data, whose camera ID is switched by the switching means in the image data displayed in a list, to image data synchronized with the other camera ID, and displays a list of the image data.

Next, the screen generating unit 254f updates the target reduced image and the capsule image in the overview image display region 21 in the overview screen 20 being displayed in the display unit 155 by using the reduced image generated in step S256 and the capsule image 21a/21b generated in step S257 (step S258). For example, the screen generating unit 254f updates the reduced image #a34 and the capsule image 21a shown in FIG. 33(a) to the reduced image #b34 and the capsule image 21b shown in FIG. 33(b) (step S258) and returns to the operation shown in FIG. 34.

As described above, in the second embodiment, the image data displayed in a list can be individually switched as necessary. Consequently, even in the medical system using the multi-eye (for example, two-eye) capsule medical device 100, the number of pieces of image data and the size of the image data to be presented at a time to the observer does not have to be decreased. As a result, even in the case of using the multi-eye (for example, two-eye) capsule medical device 100, the amount of information which can be presented at a time to the observer can be prevented from being decreased.

Modification 2-1

Figure 36:
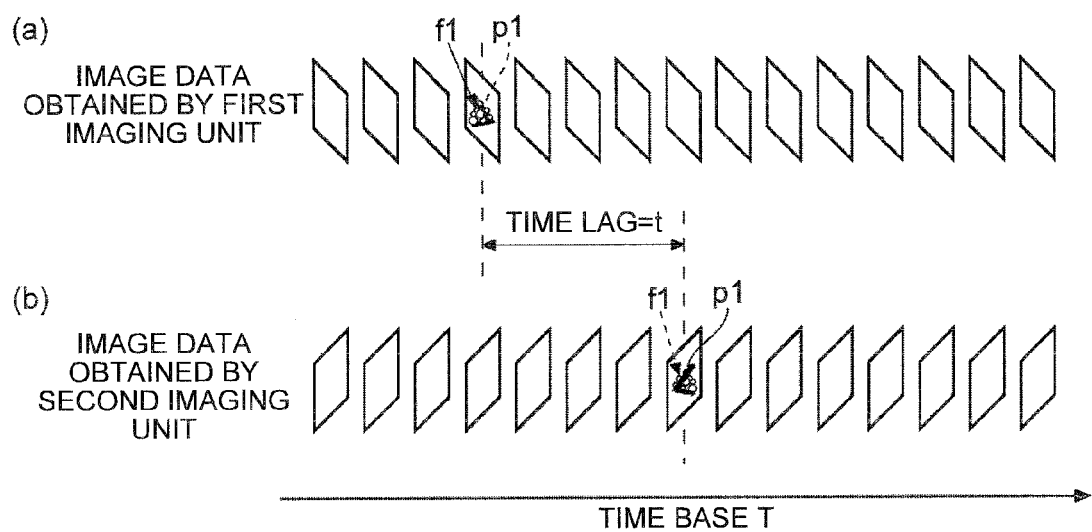
FIG. 36 is a diagram showing a state where image data of different clearness is obtained in the case of capturing images of a specific region by first and second imaging units in the second embodiment of the invention.

As shown in FIG. 36(a), there is a case such that a region (specific region p1) in image data becomes unclear due to bubbles or the like in the lumen 902 and, on the other hand, no bubbles appear in image data (refer to FIG. 36(*b*)) of the specific region p1 captured from the opposite side, and the image of the specific region p1 is clear. In such a case, the image data, which is inappropriate for observation due to unclearness or the like, is automatically replaced with image data having the other camera ID and synchronized with the image data. In the following, the case will be described in detail as modification 2-1 of the second embodiment with reference to drawings. FIG. 36 is a diagram for explaining a state where image data of different clearness is obtained in the case of imaging the same specific region p1 by the first and second imaging units 101A and 101B.

A medical system according to the modification 2-1 may have a configuration similar to that of the medical system 1 according to the first embodiment. In the modification 2-1, the display device 150 is replaced with a display device 250-1 shown in FIG. 37. In the following description, the same reference numerals are designated to components similar to those of the foregoing first and second embodiments and their modifications, and repetitive description will not be given.

Figure 37:
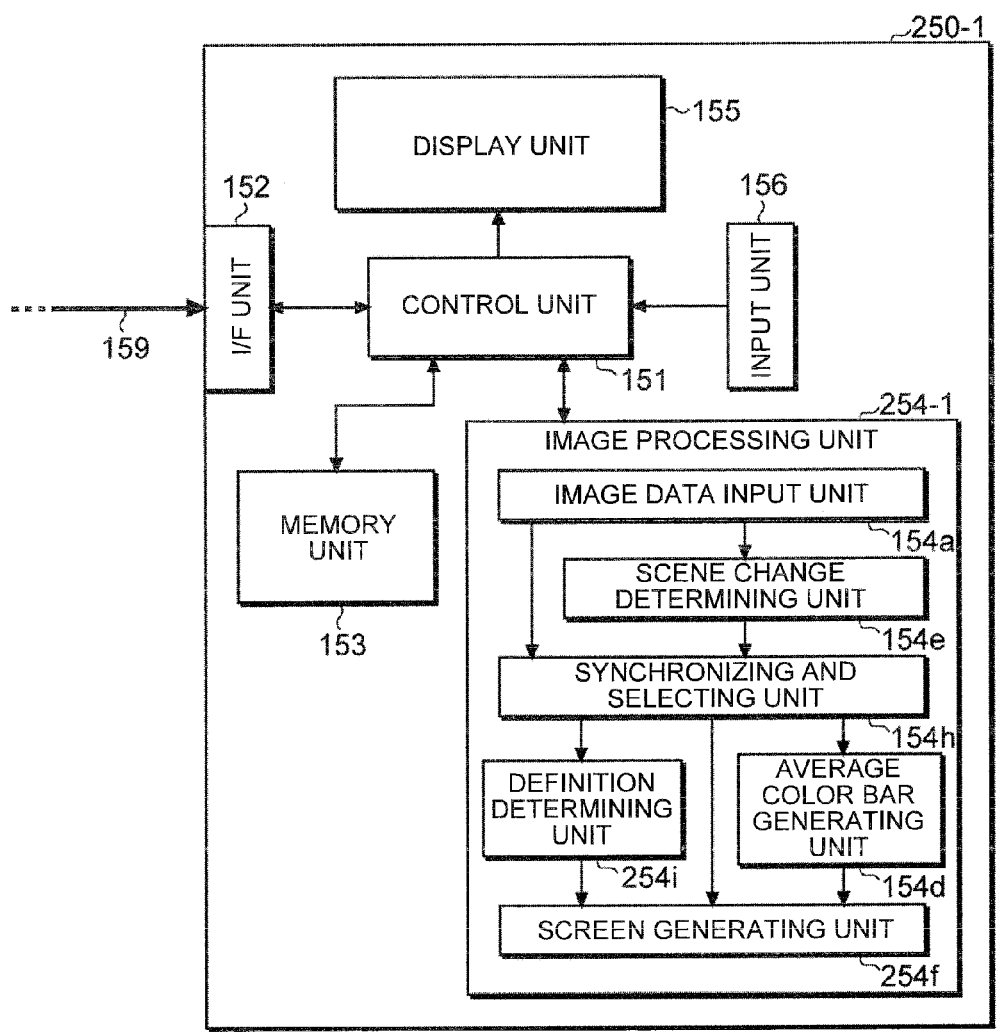
FIG. 37 is a block diagram showing an example of a schematic configuration of the display device according to modification 2-1 of the second embodiment of the invention.

FIG. 37 is a block diagram showing a schematic configuration example of the display device 250-1 according to the modification 2-1. As illustrated in FIG. 37, in the display device 250-1, the image processing unit 154 shown in FIG. 4 is replaced with an image processing unit 254-1. The image processing unit 254-1 has a configuration similar to that of the image processing unit 254 (refer to FIG. 32) in the second embodiment and has, in addition, a definition determining unit 254*i*.

The definition determining unit 254*i* functions as determining means that determines whether one of the camera IDs (it is now assumed that the camera ID=1) on selected image data output from the synchronizing and selecting unit 154*h* is not appropriate for observation, and supplies the determination result to the screen generating unit 254*f*.

The screen generating unit 254*f* generates an overview screen by using image data supplied and selected by the image selecting unit 154*h*, the definition determination result supplied from the definition determining unit 254*i*, and the images of the average color bars 15A and 15B supplied from the average color bar generating unit 154*d*. The overview screen in the modification 2-1 is similar to the overview screen 20 shown in FIG. 33(*b*). In the following description, reference numeral 20 is designated to the overview screen according to the modification 2-1.

Figure 38:
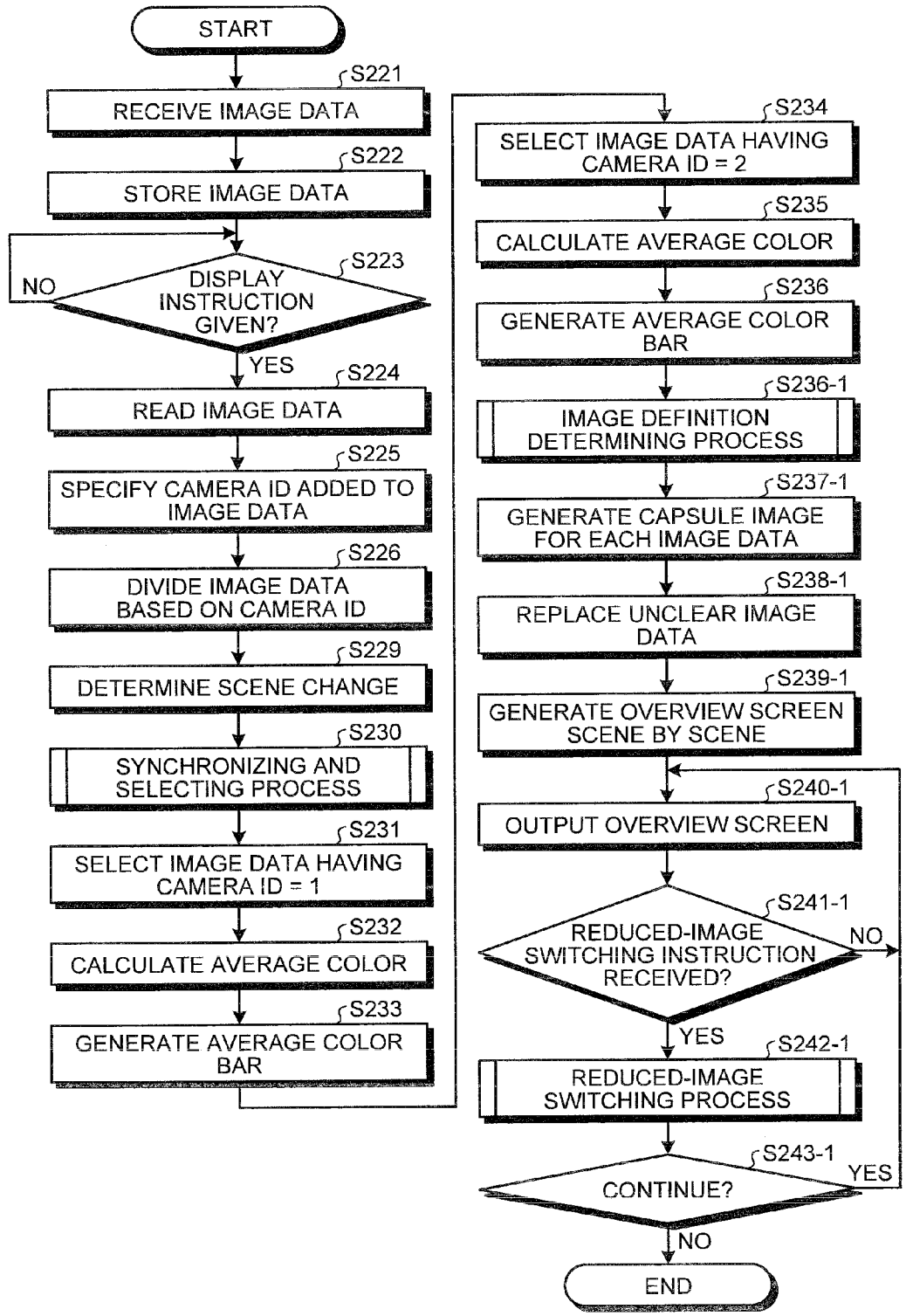
FIG. 38 is a flowchart showing an example of outline operation of the display device according to the modification 2-1 of the second embodiment of the invention.
Figure 39:
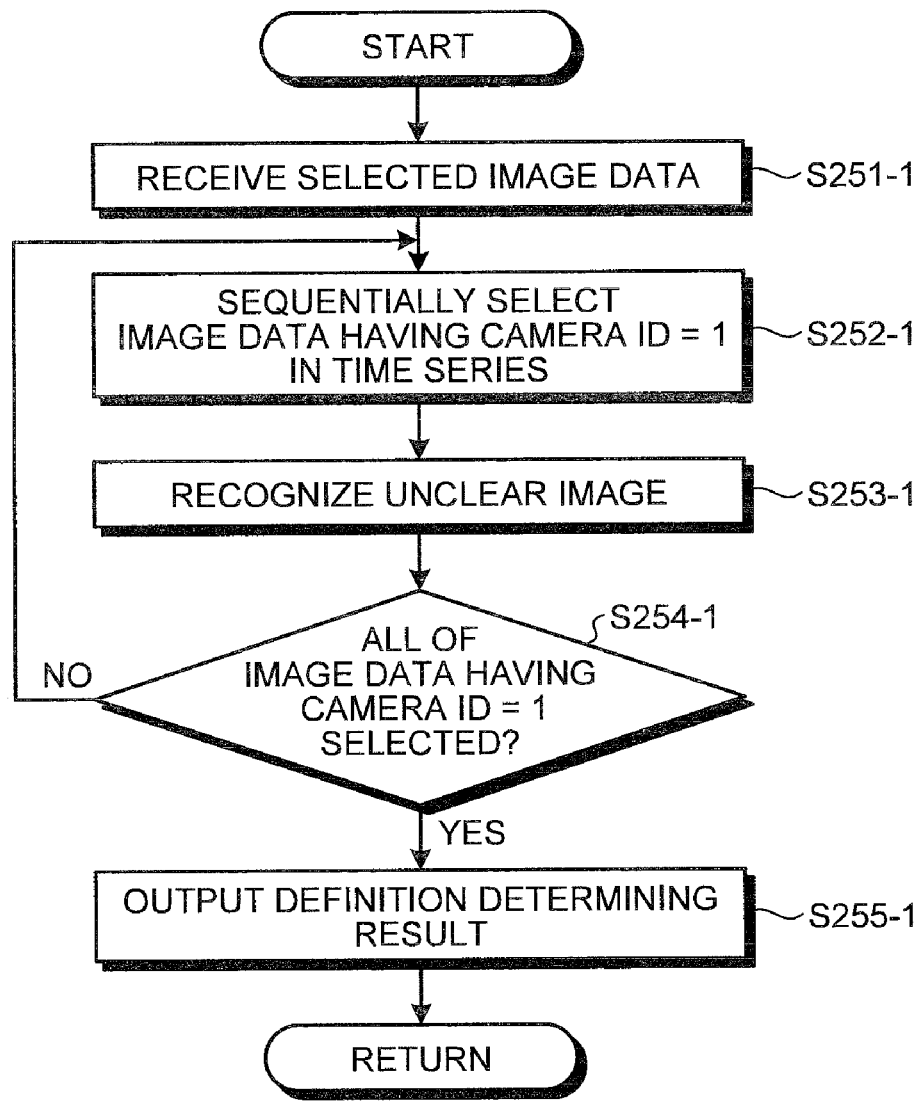
FIG. 39 is a flowchart showing a concrete example of image definition determining process in step S236-1 in FIG. 38.

Next, the operation of the medical system according to the modification 2-1 will now be described in detail with reference to the drawings. Since the operation of the capsule medical device 100 and the operation of the receiving device 130 in the modification 2-1 are similar to those of the first embodiment (refer to FIGS. 6 and 7), the detailed description will not be repeated. FIG. 38 is a flowchart showing an example of schematic operation of the display device 250-1 according to the modification 2-1. FIG. 39 is a flowchart showing a concrete example of image definition determining operation in step S236-1 in FIG. 38.

In the modification 2-1, the display device 250-1 executes operations similar to those in steps S221 to S236 in FIG. 34, thereby generating an image of the average color bar 15A on selected image data having the camera ID=1 and an image of the average color bar 15B on selected image data having the camera ID=2 (refer to steps S221 to S236 in FIG. 38). Subsequently, the definition determining unit 254*i* of the display device 250-1 executes the image definition determining process of determining definition of each of selected image data supplied from the synchronizing and selecting unit 154*h* (step S236-1). The details of the image definition determining process will be described later with reference to FIG. 39. A determination result of the image definition determining process is supplied to the screen generating unit 254*f*. Further, an image which is improper for observation can be selected manually by the observer. It enables selection of image data more convenient to the observer.

The screen generating unit 254*f* to which the definition determination result, the selected image data, and the images of the average color bars 15A and 15B are input generates the capsule image 21*a*/21*b* for each of supplied and selected image data on the basis of the camera ID of the image data (step S237-1) and, subsequently, replaces image data determined as improper for observation due to unclearness or the like from the selected image data having the camera ID=1 with selected image data having the camera ID=2 (step S238-1). The invention is not limited to the case. In place of image data determined as improper for observation, an image which is blank (null) or grayout may be displayed.

Next, the screen generating unit 254*f* generates the overview screen 20 of each scene as shown in FIG. 33(*a*) by using image data replaced and organized, the capsule image 21*a*/21*b* corresponding to the image data, and images of the average color bars 15A and 15B (step S239-1) and outputs the generated overview screen 20 to the display unit 155 (step S240-1). Consequently, the overview screen 20 as a GUI screen is displayed on the display unit 155, and the GUI function using the overview screen 20 is provided to the user.

After that, the display device 250-1 determines whether the instruction of switching a reduced image displaced in the overview display region 21 in the overview screen 20 by using, for example, the mouse or the like of the input unit 156 (step S241-1). In the case where the instruction is input (Yes at step S241-1), the display device 250-1 executes a reduced-image switching process of switching a reduced image displayed in the overview image display region 21 (step S242-1).

On the other hand, in the case where the reduced-image switching instruction has not been supplied (No at step S241-1), the display device 250-1 determines whether the operation is continued, for example, whether the operation end instruction is received from the input unit 156 (step S243-1). In the case of continuing the operation (Yes at step S243-1), the display device 250-1 returns to step S240-1. On the other hand, in the case where the operation is not continued (No at step S243-1), the operation is finished.

In the image definition determining process shown in step S236-1 in FIG. 38, the definition determining unit 254*i* of the display device 250-1 receives selected image data from the synchronizing and selecting unit 154*h* (step S251-1), sequentially selects image data having the camera ID=1 in the input image data in time series in accordance with the image pickup time indicated by the time stamp (step S252-1), and determines whether the selected image data is unclear (step S253-1). Whether an image is clear or not can be determined by, for example, whether a specific pattern such as a bubble is included in an image, the edge of each region is sharp or not, and the like.

After that, the definition determining unit 254*i* determines whether all of image data having the camera ID=1 selected in step S252-1 has been selected (step S254-1). When all of the image data has not been selected yet (No at step S254-1), the definition determining unit 254*i* returns to step S252-1 and selects the next selected image data having the camera ID=1.

On the other hand, all of the image data having the camera ID=1 selected in step S252-1 has been selected (Yes at step S254-1), the definition determining unit 254*i* outputs the definition determination result in step S253-1 to the screen generating unit 254*f* by image data (step S255-1) and, after that, returns to the operation shown in FIG. 38.

As described above, in the modification 2-1, in addition to effects similar to those of the second embodiment, image data which is improper for observation is automatically determined and can be replaced with image data of the other camera ID.

Modification 2-2

Figure 40:
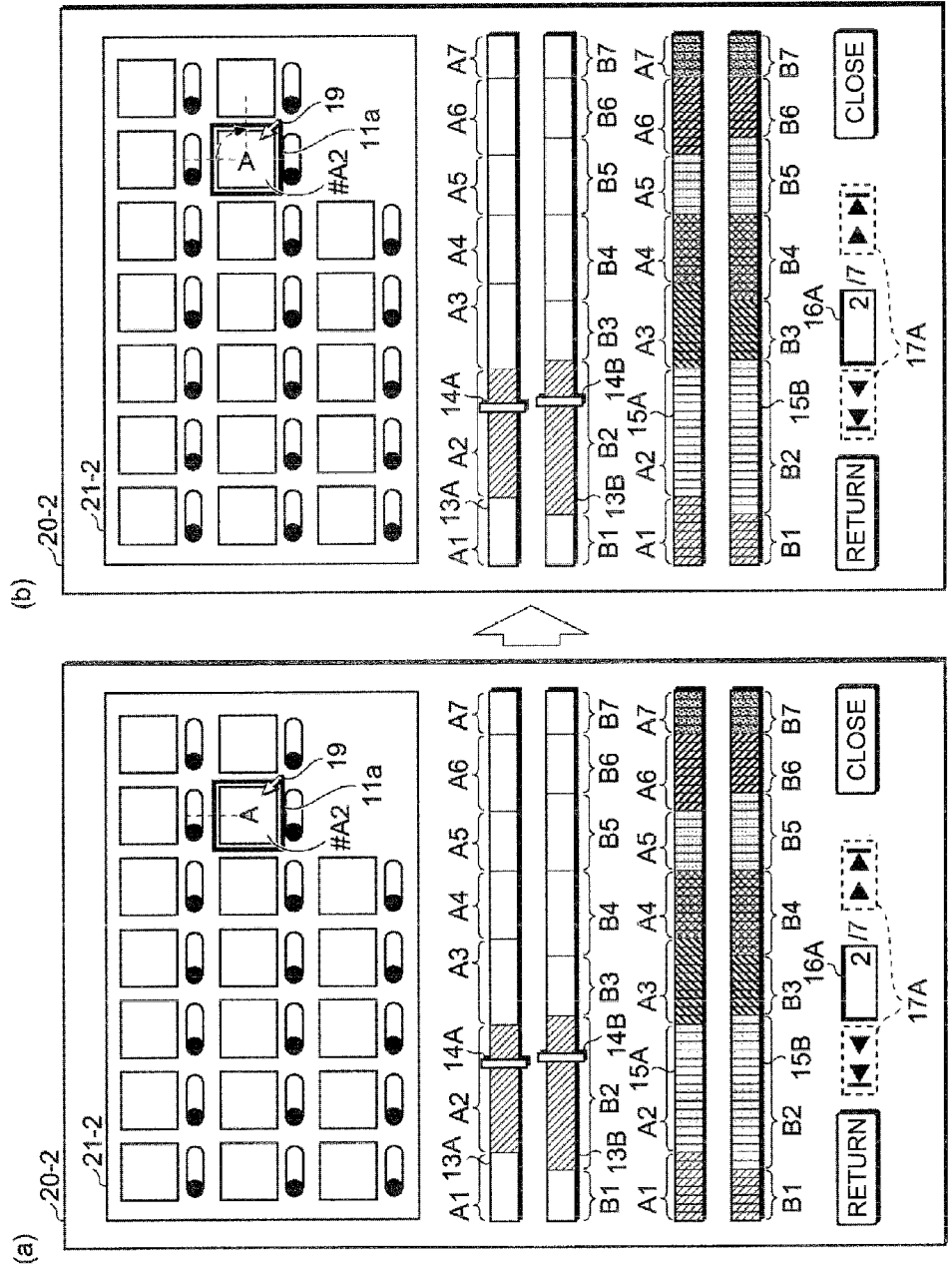
FIG. 40 is a diagram showing an example of an overview screen according to modification 2-2 of the second embodiment of the invention.

In the second embodiment and its modifications, as shown in an overview screen 20-2 according to modification 2-2 of the second embodiment shown in FIG. 40, it may be constructed that the observer can arbitrarily rotate each of reduced images in an overview image display region (for example, an overview image display region 21-2). Since the configuration and operation can be easily reached from the second embodiment and the modification 1-3 of the first embodiment, detailed description will not be given here. FIG. 40 is a diagram showing an example of the overview screen 20-2 according to the modification 2-2. FIG. 40(*a*) shows an example of the overview screen 20-2 before a reduced image #A2 is rotated, and FIG. 40(*b*) shows an example of the overview screen 20-2 after the reduced image #A2 is rotated.

Modification 2-3

In the second embodiment and its modifications, as shown in an overview screen 20-3 according to modification 2-3 of the second embodiment shown in FIG. 41, it may be constructed that the observer can arbitrarily change the size of an overview image display region 21-3 and/or the number of reduced images displayed in a list in the overview image display region 21-3. Since the configuration and operation can be easily reached from the second embodiment and the modification 1-4 of the first embodiment, detailed description will not be given here. FIG. 41 is a diagram showing an example of the overview screen 20-3 according to the modification 2-3. FIG. 41(*a*) shows an example of the overview screen 20-3 before the size of the overview image display region 21-3 and/or the number of reduced images displayed in a list in the overview image display region 21-3 is/are changed, and FIG. 41(*b*) shows an example of the overview screen 20-3 after the size of the overview image display region 21-3 and/or the number of reduced images displayed in a list in the overview image display region 21-3 is/are changed.

Third Embodiment

Another form of displaying reduced images of image data obtained by different imaging units in a single overview screen display region will be described in detail as a third embodiment of the present invention with reference to the drawings.

A medical system according to the third embodiment may have a configuration similar to that of the medical system 1 according to the first embodiment. In the third embodiment, the display device 150 is replaced with a display device 350 shown in FIG. 42. In the following description, the same reference numerals are designated to components similar to those of the foregoing first and second embodiments and their modifications, and repetitive description will not be given.

Figure 42:
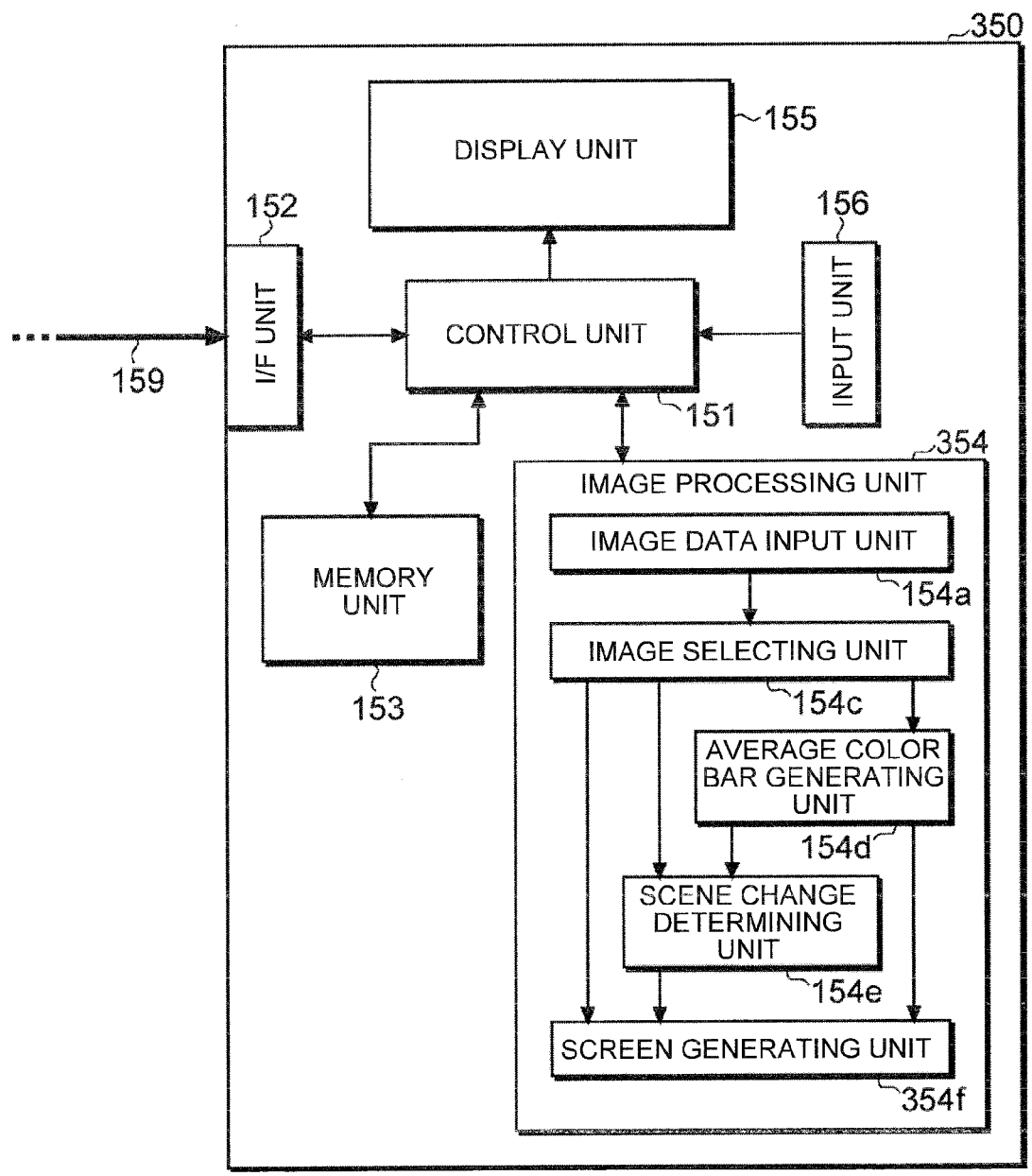
FIG. 42 is a block diagram showing an example of a schematic configuration of a display device according to a third embodiment of the invention.

FIG. 42 is a block diagram showing a schematic configuration example of the display device 350 according to the third embodiment. As illustrated in FIG. 42, in the display device 350, the image processing unit 154 shown in FIG. 4 is replaced with an image processing unit 354. The image processing unit 354 has a configuration similar to that of the image processing unit 154 (refer to FIG. 4) in the first embodiment except that the screen generating unit 154*f* is replaced with a screen generating unit 354*f*.

Figure 43:
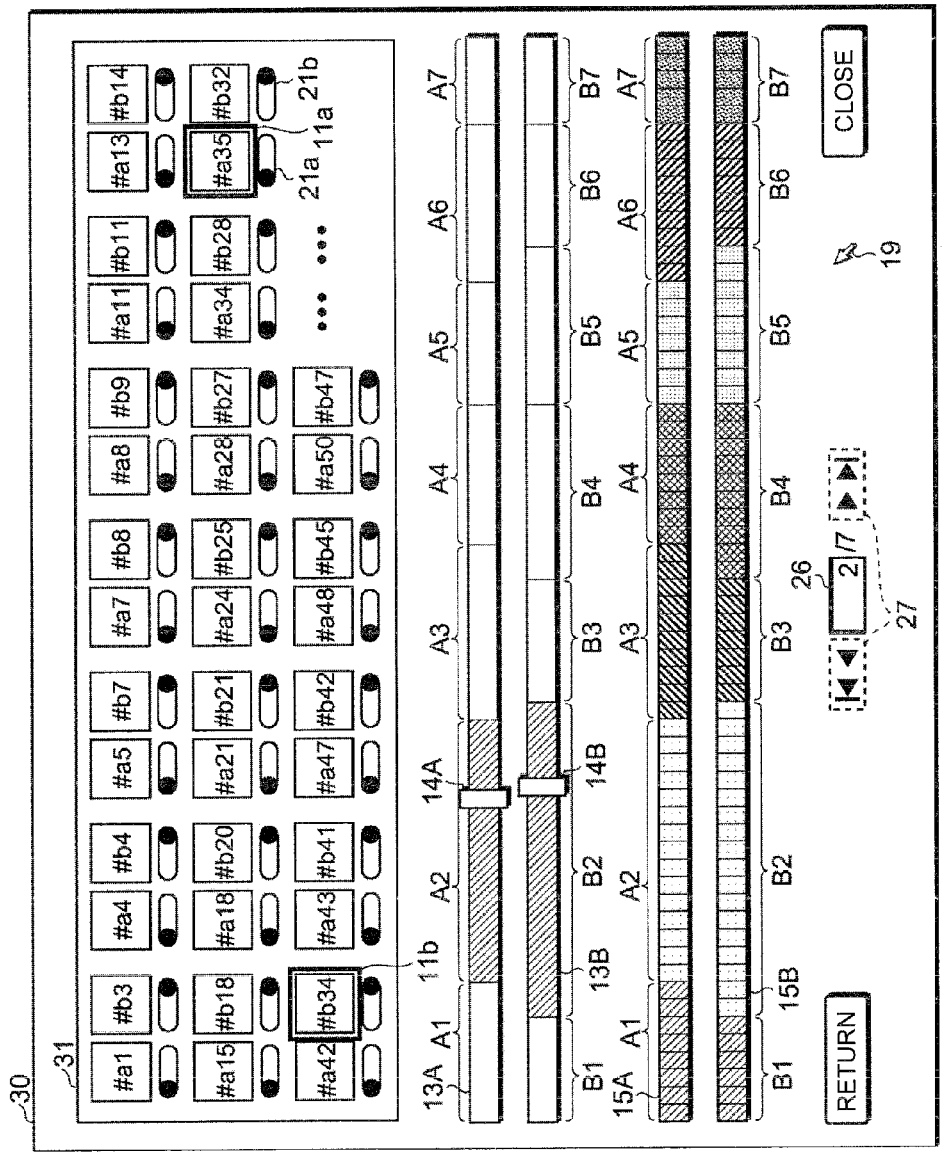
FIG. 43 is a diagram showing an example of an overview screen according to the third embodiment of the invention.

The screen generating unit 354*f* generates an overview screen 30 as shown in FIG. 43 by using image data output and selected by the image selecting unit 154*c* and the images of the average color bars 15A and 15B output from the average color bar generating unit 154*d*. FIG. 43 shows an example of the overview screen 30 according to the third embodiment.

As shown in FIG. 43, the overview screen 30 according to the third embodiment includes an overview image display region 31 displaying a list of pairs of reduced images each made of a reduced image of selected image data having the camera ID=1 and a reduced image of selected image data having the camera ID=2 which are arranged side by side, the time scale bar 13A, the slider 14A, and the average color bar 15A on image data having the camera ID=1, the time scale bar 13B, the slider 14B, and the average color bar 15B on image data having the camera ID=2, the display scene box 26 indicative of the order of a scene being displayed in the overview image display region 31 in all of scenes, and the scene switching button 27 for switching the scene to be displayed in the overview image display region 31.

In the overview image display region 31, pairs of reduced images each made of a reduced image of selected image data having the camera ID=1 and a reduced image of selected image data having the camera ID=2 which are arranged in a list along time series. Near (for example, below) each reduced image, an image (hereinbelow, called capsule image) 21*a*/21*b* visually showing, to the observer, the imaging unit (101A or 101B) of the capsule medical device 100 which captured the reduced image may be displayed.

Figure 44:
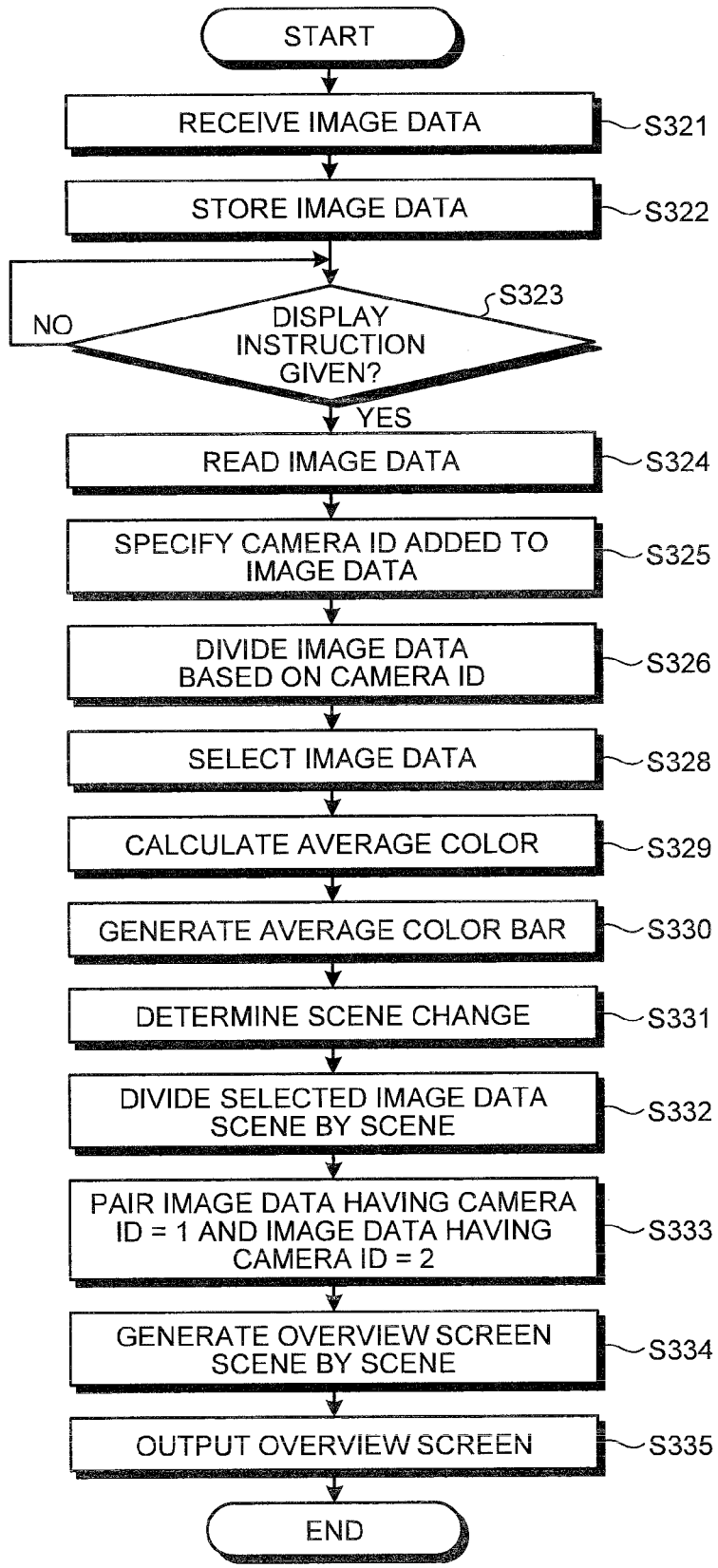
FIG. 44 is a flowchart showing an example of outline operation of the display device according to the third embodiment of the invention.

The operation of the medical system according to the third embodiment will now be described in detail with reference to the drawings. Since the operation of the capsule medical device 100 and that of the receiving device 130 in the third embodiment are similar to those of the first embodiment (refer to FIGS. 6 and 7), the detailed description will not be repeated. FIG. 44 is a flowchart showing an example of schematic operation of the display device 350 according to the third embodiment.

As shown in FIG. 44, the display device 350 according to the third embodiment receives image data from the interface unit 152 using the portable recording medium 140 or the communication cable 159 as a medium (step S321) and temporarily stores the image data in the memory unit 153 or the like via the control unit 151 (step S322).

Next, the display device 350 waits until a display instruction of the overview screen 30 is supplied from the input unit 156 or the like (No at step S323). In the case where a display instruction is received (Yes at step S323), the display device 350 reads image data stored in the memory unit 153 or the like (step S324). The read image data is supplied to the image data input unit 154*a* in the image processing unit 354.

The image data input unit 154*a* specifies each of the camera IDs added to the input image data (step S325) and divides the image data by imaging units (101A and 101B) on the basis of the camera IDs, that is, by camera IDs (step S326). The divided image data is supplied to the scene change determining unit 154*e*.

The image selecting unit 154*c* specifies and selects image data to be displayed on the basis of an image process result obtained by processing the input image data (step S328). The selected image data is supplied to the average color bar generating unit 154*d*, the scene change determining unit 154*e*, and the screen generating unit 354*f*.

The average color bar generating unit 154*d* to which the selected image data is supplied selects image data by camera IDs, calculates an average color of each of the image data (or each of regions obtained by dividing the image data) (step S329) and, on the basis of the calculation result, generates the average color bars 15A and 15B obtained by connecting images of average colors along time series (step S330). The generated average color bars 15A and 15B are supplied to the screen generating unit 354f. The generated average color bars 15A and 15B may be supplied to the scene change determining unit 154e.

The scene change determining unit 154e determines image data whose scene is changed on the basis of image data on the basis of an image process result of successive image data in image data input from the image selecting unit 154c (step S331). The scene change determination result is supplied to the screen generating unit 354f.

The screen generating unit 354f divides the selected image data by camera IDs scene by scene from the input selected image data and the scene change determination result (step S332) and pairs image data having the camera ID=1 and image data having the camera ID=2 scene by scene (step S333). Subsequently, the screen generating unit 354f generates the overview screen 30 shown in FIG. 43 from the image data divided scene by scene and paired and the images of the average color bars 15A and 15B (step S334), outputs it to the display unit 155 via the control unit 151 (step S335), and finishes the operation.

As described above, in the third embodiment, image data obtained by different eyes can be disposed side by side and displayed in a list. Therefore, the observer can easily observe a region in the subject 900 from a plurality of angles.

Modification 3-1a

Although image data having different camera IDs is paired, synchronous image data may be paired as described in the modification 1-2a of the first embodiment. In the following, the case will be described in detail as modification 3-1a of the third embodiment with reference to the drawings.

A medical system according to the modification 3-1a may have a configuration similar to that of the medical system 1 according to the first embodiment. In the modification 3-1a, the display device 150 is replaced with a display device 350-1a shown in FIG. 45. In the following description, the same reference numerals are designated to components similar to those of the foregoing first, second, and third embodiments and their modifications, and repetitive description will not be given.

Figure 45:
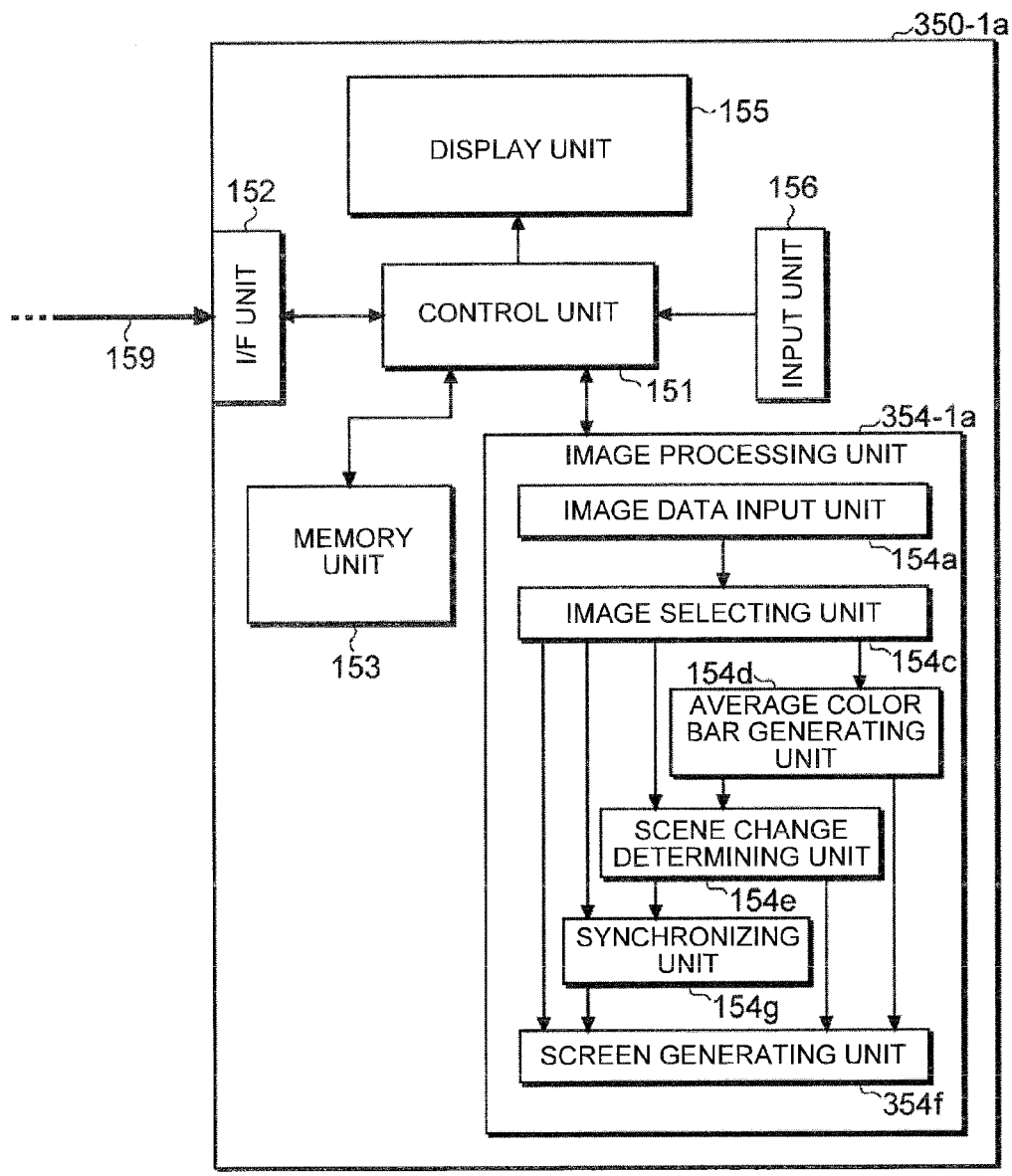
FIG. 45 is a block diagram showing an example of a schematic configuration of a display device according to modification 3-1a of the third embodiment of the invention.

FIG. 45 is a block diagram showing a schematic configuration example of the display device 350-1a according to the modification 3-1a. As illustrated in FIG. 45, in the display device 350-1a, the image processing unit 154 shown in FIG. 4 is replaced with an image processing unit 354-1a. The image processing unit 354-1a has a configuration similar to that of the image processing unit 354 (refer to FIG. 42) in the third embodiment except that the synchronizing unit 154g is provided. The synchronizing unit 154g is similar to the synchronizing unit 154g according to the modification 1-2a of the first embodiment (refer to FIG. 12).

Figure 46:
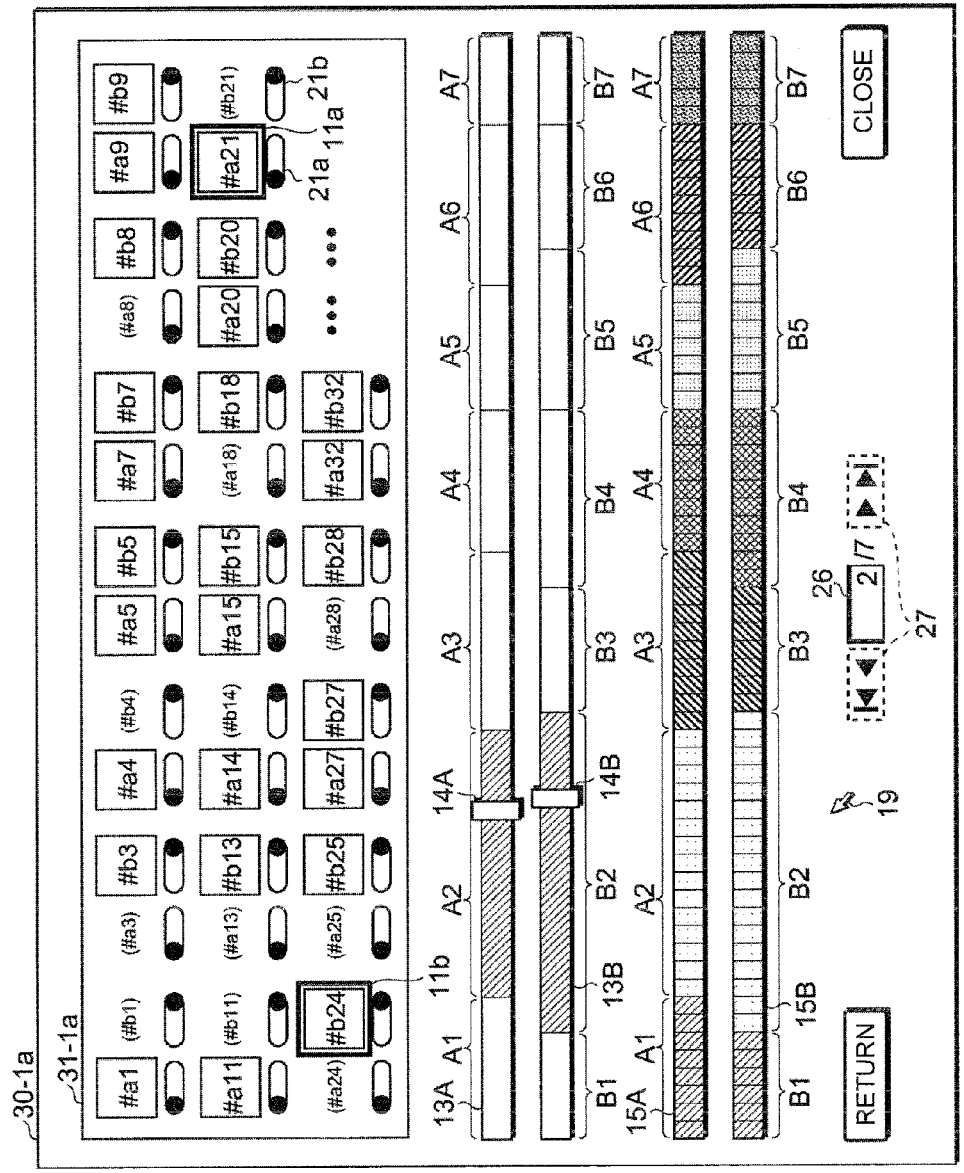
FIG. 46 is a diagram showing an example of an overview screen according to the modification 3-1a of the third embodiment of the invention.

In the modification 3-1a, the screen generating unit 354f generates an overview screen 30-1a as shown in FIG. 46 by using the selected image data supplied from the image selecting unit 154c, a scene change determination result supplied from the scene change determining unit 154e, and images of the average color bars 15A and 15B supplied from the average color bar generating unit 154d. FIG. 46 shows an example of the overview screen 30-1a according to the modification 3-1a.

As shown in FIG. 46, in the overview image display region 31-1a in the overview screen 30-1a, a reduced image generated from image data selected from image data #a1 to #a50 having the camera ID=1 and a reduced image generated from image data selected from image data #b1 to #b47 having the camera ID=2 are paired and displayed. In the overview image display region 31-1a, a display portion in which there is no synchronous image data is blank. In other words, portions having no synchronous image data are blank.

Figure 47:
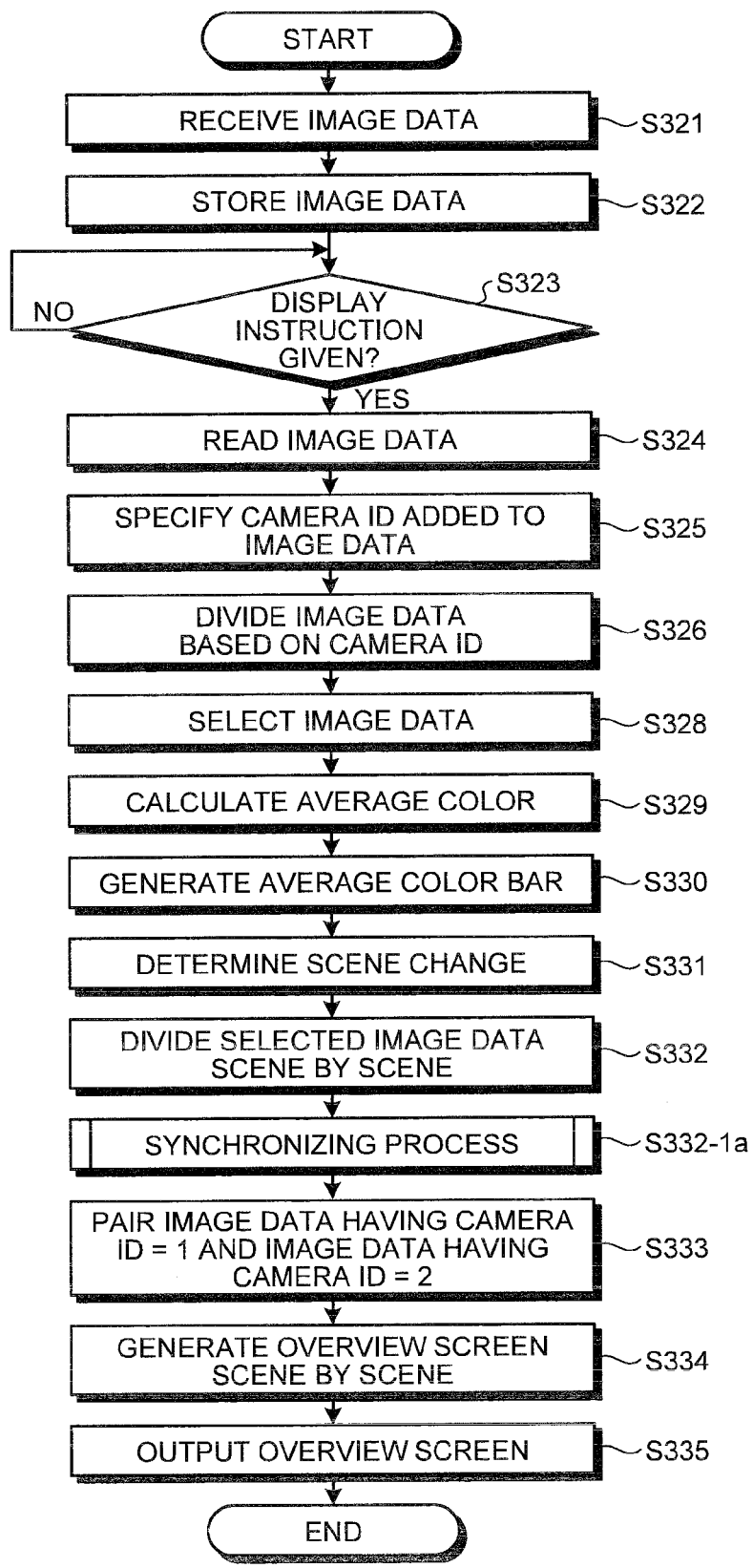
FIG. 47 is a flowchart showing a schematic operation of the display device according to the modification 3-1a of the third embodiment of the invention.

Next, the operation of the medical system according to the modification 3-1a will be described in detail with reference to the drawings. Since the operation of the capsule medical device 100 and the operation of the receiving device 130 in the modification 3-1a are similar to those (FIGS. 6 and 7) in the first embodiment, detailed description will not be given. FIG. 47 is a flowchart showing outline operation of the display device 350-1a according to the modification 3-1a.

The display device 350-1a according to the modification 3-1a executes operations similar to those in steps S321 to S332 in FIG. 44, thereby dividing the selected image data scene by scene (refer to steps S321 to S332 in FIG. 47). Subsequently, on the basis of the selected image data and the scene change determination result, the synchronizing unit 154g in the display device 350-1a executes a process of synchronizing the image data having the camera ID=1 and the image data having the camera ID=2 (step S332-1a). Since the details of the synchronizing process are similar to those of the synchronizing process (refer to FIG. 14) in the modification 1-2a of the first embodiment, the detailed description will not be repeated.

The screen generating unit 354f pairs the image data having the camera ID=1 and the image data having the camera ID=2 in the synchronized image data scene by scene (step S333). Subsequently, the screen generating unit 354f generates an overview screen 30-1a as shown in FIG. 46 by using the image data divided scene by scene and paired and the images of the average color bars 15A and 15B (step S334), and output to the display unit 155 via the control unit 151 (step S335), and finishes the operation.

As described above, in the modification 3-1a, image data obtained by capturing images of the same position by different eyes can be arranged side by side and displayed in a list. Therefore, the observer can easily observe a region in the subject 900 from a plurality of angles.

Modification 3-1b

Although image data having different camera IDs is paired, synchronous image data may be paired as described in the modification 1-2b of the first embodiment. In the following, the case will be described in detail as modification 3-1b of the third embodiment with reference to the drawings.

A medical system according to the modification 3-1b may have a configuration similar to that of the medical system 1 according to the first embodiment. In the modification 3-1b, the display device 150 is replaced with a display device 350-1b shown in FIG. 48. In the following description, the same reference numerals are designated to components similar to those of the foregoing first, second, and third embodiments and their modifications, and repetitive description will not be given.

Figure 48:
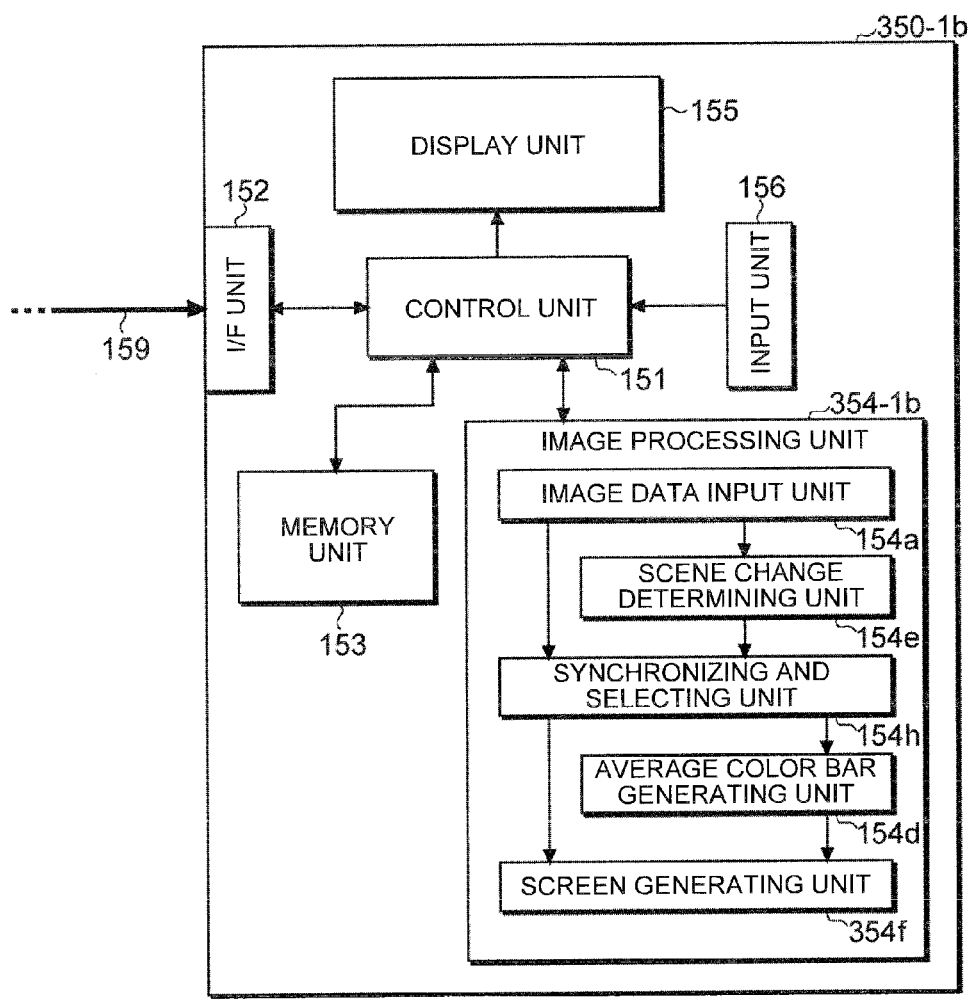
FIG. 48 is a block diagram showing an example of a schematic configuration of a display device according to modification 3-1b of the third embodiment of the invention.

FIG. 48 is a block diagram showing a schematic configuration example of the display device 350-1b according to the modification 3-1b. As illustrated in FIG. 48, in the display device 350-1b, the image processing unit 154 shown in FIG. 4 is replaced with an image processing unit 354-1b. The image processing unit 354-1b has a configuration similar to that of the image processing unit 354 (refer to FIG. 42) in the third embodiment except that the image selecting unit 154c is replaced with the synchronizing and selecting unit 154h. Further, in the image processing unit 354-1b, image data output from the image data input unit 154a is supplied to the scene change determining unit 154*e* and the synchronizing and selecting unit 154*h*, and a scene change determination result by the scene change determining unit 154*e* is supplied to the synchronizing and selecting unit 154*h*. Since the synchronizing and selecting unit 154*h* is similar to the synchronizing and selecting unit 154*h* in the modification 1-2b of the first embodiment, detailed description will not be repeated.

Figure 49:
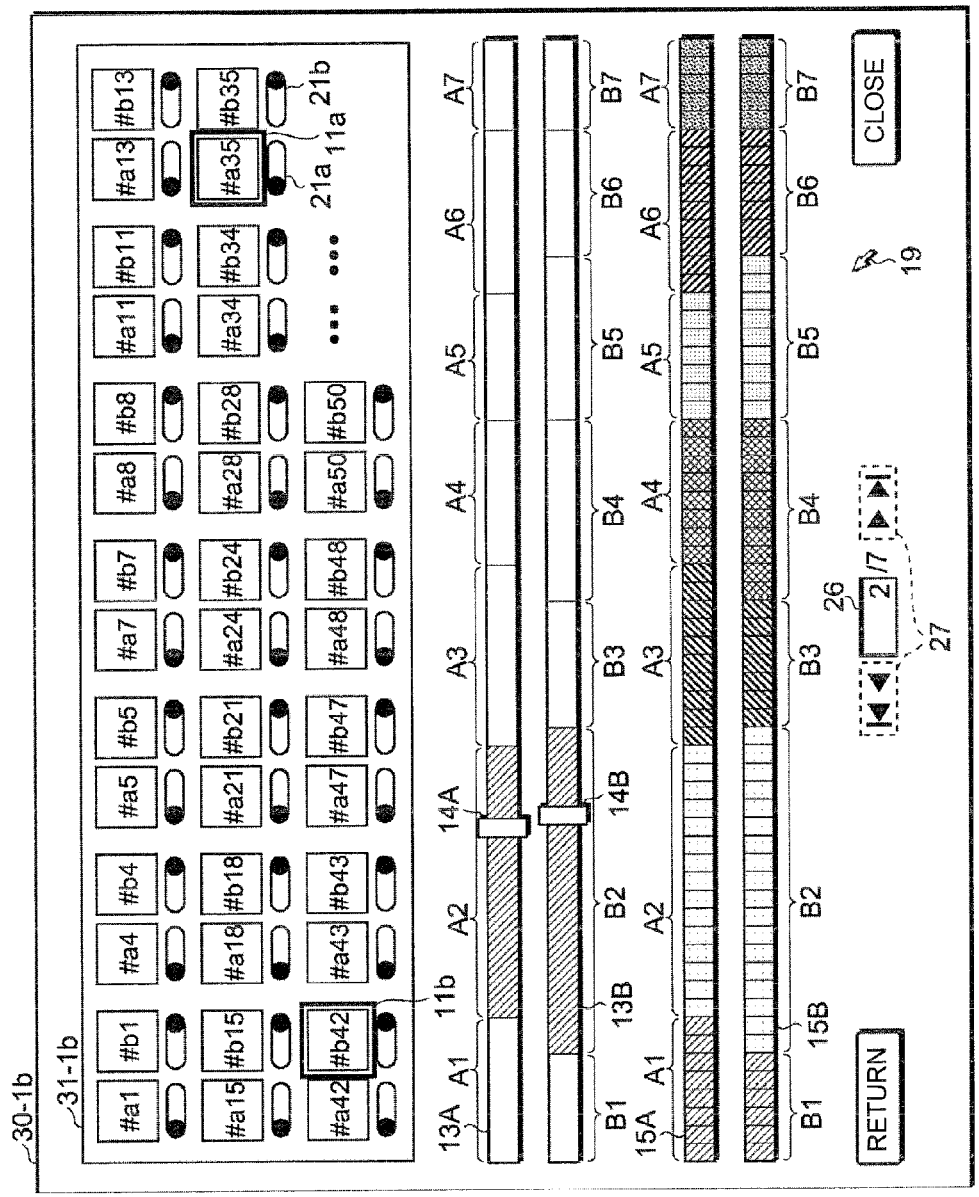
FIG. 49 is a diagram showing an example of an overview screen according to the modification 3-1b of the third embodiment of the invention.

In the modification 3-1b, the screen generating unit 354*f* generates an overview screen 30-1*b* as shown in FIG. 49 by using the selected and synchronized image data supplied from the synchronizing and selecting unit 154*h*, a scene change determination result supplied from the scene change determining unit 154*e* via the synchronizing and selecting unit 154*h*, and images of the average color bars 15A and 15B supplied from the average color bar generating unit 154*d*. FIG. 49 shows an example of the overview screen 30-1*b* according to the modification 3-1b.

As shown in FIG. 49, in the overview image display region 31-1*b* in the overview screen 30-1*b*, a reduced image generated from image data selected from image data #a1 to #a50 having the camera ID=1 and a reduced image generated from image data having the camera ID=2 and synchronized with the selected image data having the camera ID=1 are paired and displayed.

Figure 50:
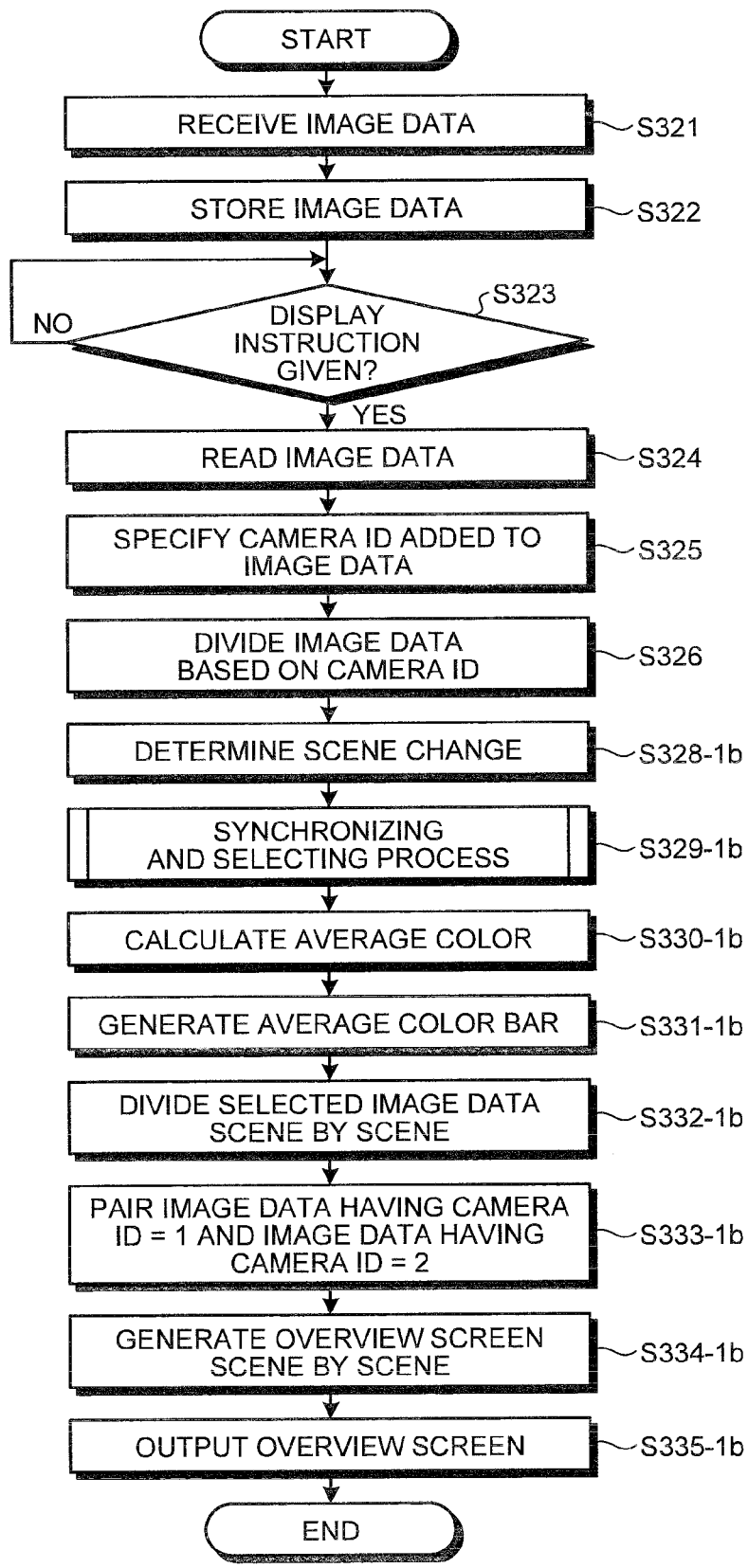
FIG. 50 is a flowchart showing an example of a schematic operation of the display device according to the modification 3-1b of the third embodiment of the invention.

Next, the operation of the medical system according to the modification 3-1b will be described in detail with reference to the drawings. Since the operation of the capsule medical device 100 and the operation of the receiving device 130 in the modification 3-1b are similar to those (FIGS. 6 and 7) in the first embodiment, detailed description will be omitted. FIG. 50 is a flowchart showing an outline operation example of the display device 350-1*b* according to the modification 3-1b.

The display device 350-1*b* according to the modification 3-1b executes operations similar to those in steps S321 to S326 in FIG. 44, thereby dividing the image data to image data having the camera ID=1 and image data having the camera ID=2 (refer to steps S321 to S326 in FIG. 50). Subsequently, on the basis of results on image process on successive image data in the image data supplied from the image data input unit 154*a*, the scene change determining unit 154*e* determines image data in which a scene change occurs (step S328-1*b*). The scene change determination result is supplied to the synchronizing and selecting unit 154*h*.

The synchronizing and selecting unit 154*h* executes synchronizing and selecting process of selecting image data having the camera ID=1 and selecting image data having the camera ID=2 and synchronized with the selected image data having the camera ID=1 on the basis of the result of the scene change determination supplied from the scene change determining unit 154*e* (step S329-1*b*). Since the details of the synchronizing and selecting process are similar to those of the synchronizing and selecting process (refer to FIG. 19) in the modification 1-2b of the first embodiment, the detailed description will be omitted. The selected image data is supplied to the average color bar generating unit 154*d* and the screen generating unit 354*f*.

The average color bar generating unit 154*d* to which the selected image data is supplied selects image data by camera IDs, calculates an average color of each image data (or each of regions obtained by dividing the image data) (step S330-1*b*) and, on the basis of the calculation result, generates the average color bars 15A and 15B obtained by connecting the images of the average colors along time series of the image data (step S331-1*b*). The generated average color bars 15A and 15B are supplied to the screen generating unit 354*f*.

The screen generating unit 354*f* divides the supplied selected image data and the selected image data by camera IDs from the scene change determination result which is supplied via the synchronizing and selecting unit 154*h* (step S332-1*b*), and pairs the image data having the camera ID=1 and the image data having the camera ID=2 scene by scene (step S333-1*b*). Subsequently, the screen generating unit 354*f* generates an overview screen 30-1*b* as shown in FIG. 49 by using the image data divided scene by scene and paired and the images of the average color bars 15A and 15B (step S334-1*b*), and output it to the display unit 155 via the control unit 151 (step S335-1*b*), and finishes the operation.

As described above, in the modification 3-1b, image data obtained by capturing images of the same position by different eyes can be arranged side by side and displayed in a list. Therefore, the observer can easily observe a region in the subject 900 from a plurality of angles.

Figure 51:
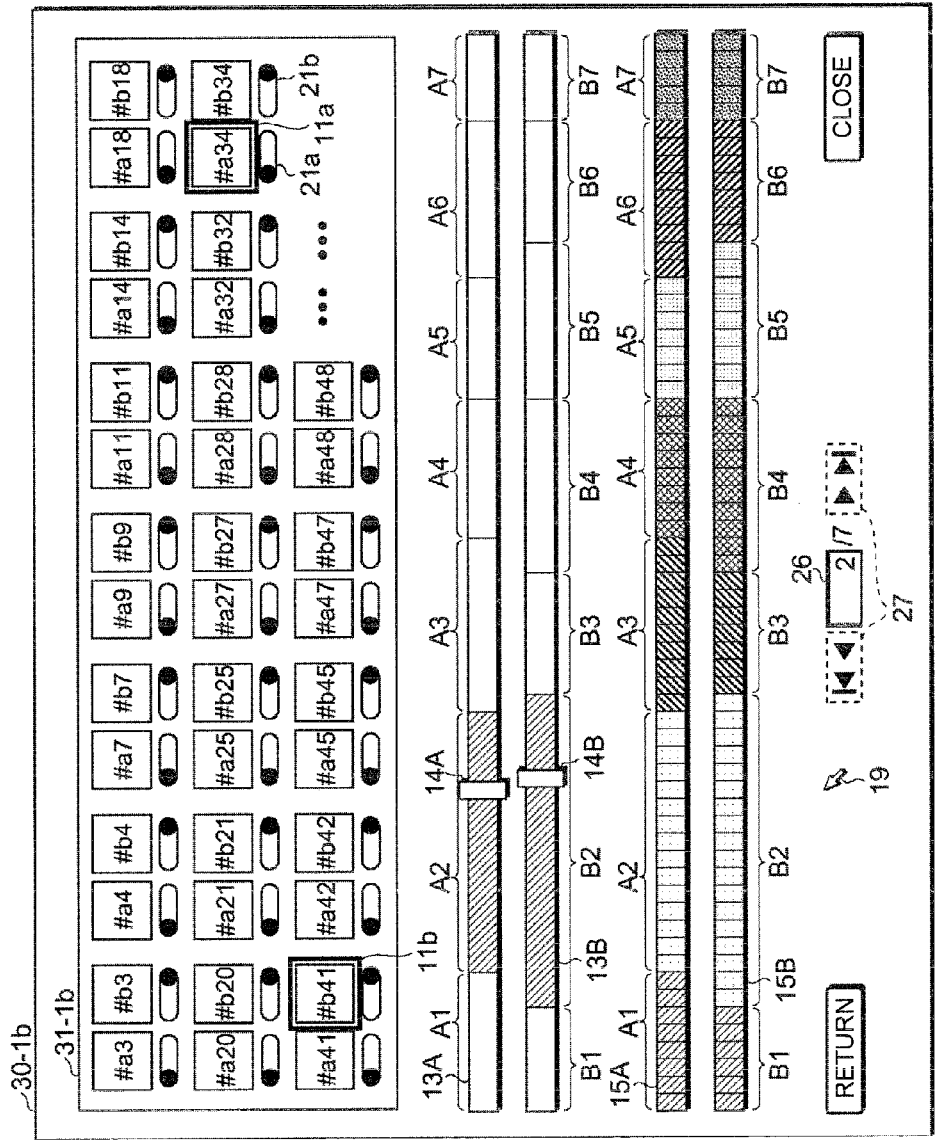
FIG. 51 is a diagram showing another example of an overview screen according to the modification 3-1b of the third embodiment of the invention.

In the modification 3-1b, for convenience of explanation, image data as a criterion to select image data to be synchronized is selected image data having the camera ID=1. However, the invention is not limited to the case. For example, selected image data having the camera ID=2 can be used as a criterion. In this case, the overview screen 30-1*b* generated by the screen generating unit 354*f* (step S334-1*b*) is as shown in FIG. 51.

Modification 3-1c

Although image data having different camera IDs is paired, synchronous image data may be paired as described in the modification 1-2c of the first embodiment. In the following, the case will be described in detail as modification 3-1c of the third embodiment with reference to the drawings.

In the modification 3-1c, a configuration similar to that of the display device 350-1*b* shown in FIG. 48 and an operation similar to that of the display device 350-1*b* shown in FIG. 50 can be applied. As the operations of the synchronizing and selecting unit 154*h* in the modification 3-1c, that is, the flow of the synchronizing and selecting process in step S329-1*b* in FIG. 50, operations similar to those (refer to FIG. 22) in the modification 1-2c of the first embodiment can be applied.

Figure 52:
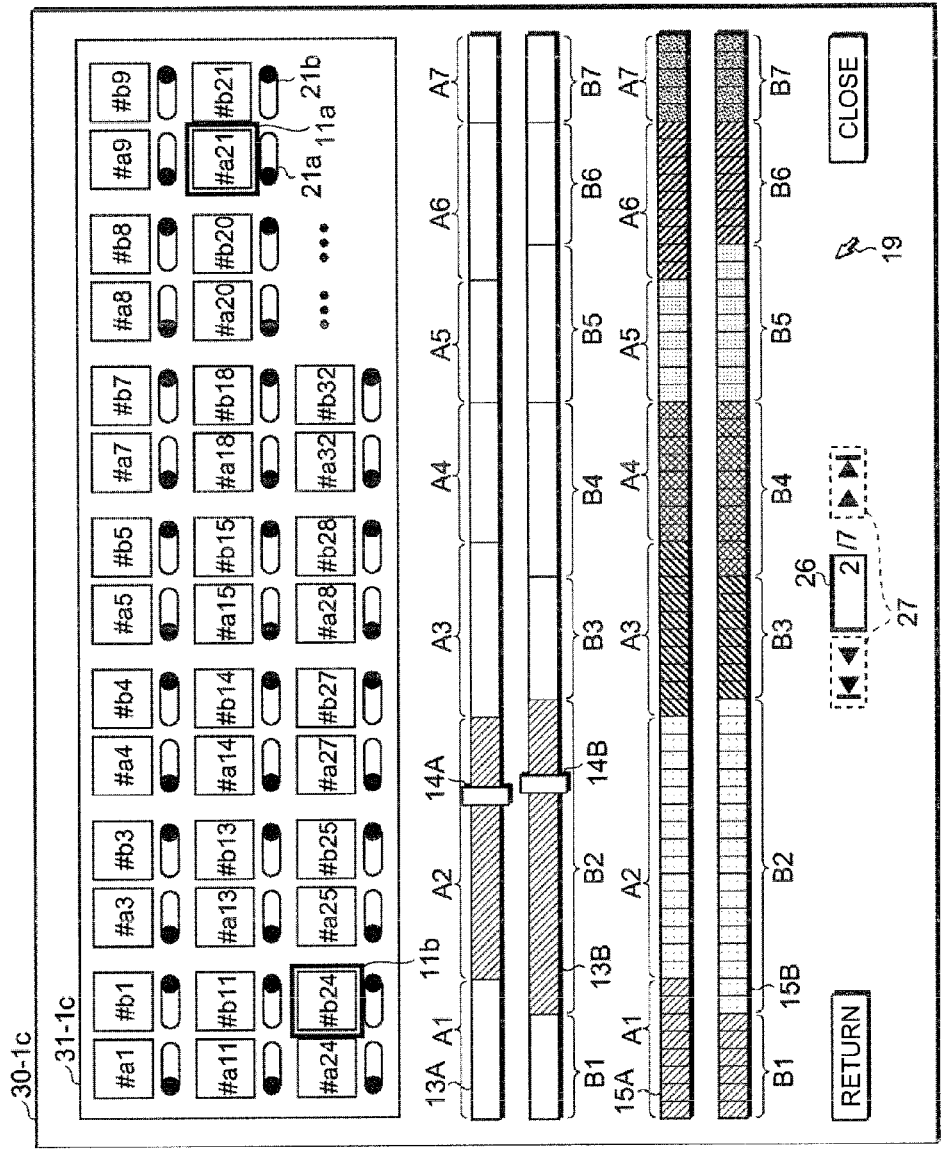
FIG. 52 is a diagram showing an example of an overview screen according to modification 3-1c of the third embodiment of the invention.

With the configuration and operation as described above, in the modification 3-1c, an overview screen 30-1*c* as shown in FIG. 52 is generated and displayed. FIG. 52 shows an example of the overview screen 30-1*c* according to the modification 3-1c.

As shown in FIG. 52, in the overview image display region 31-1*c* in the overview screen 30-1*c*, so-called logical sum (OR) is obtained between selected image data having the camera ID=1 and selected image data having the camera ID=2 and reduced images of the matching image data are paired and displayed.

As described above, in the modification 3-1c, the image data of the same position, obtained by different eyes is arranged side by side and a list of the image data can be displayed. Thus, the observer can easily observe a region in the subject 900 from a plurality of angles.

Modification 3-1d

Although image data having different camera IDs is paired, synchronous image data may be paired as described in the modification 1-2d of the first embodiment. In the following, the case will be described in detail as modification 3-1d of the third embodiment with reference to the drawings.

In the modification 3-1d, a configuration similar to that of the display device 350-1*b* shown in FIG. 48 and an operation similar to that of the display device 350-1*b* shown in FIG. 50 can be applied. As the operations of the synchronizing and selecting unit 154*h* in the modification 3-1d, that is, the flow of the synchronizing and selecting process in step S329-1*b* in FIG. 50, operations similar to those (refer to FIG. 22) in the modification 1-2d of the first embodiment can be applied.

Figure 53:
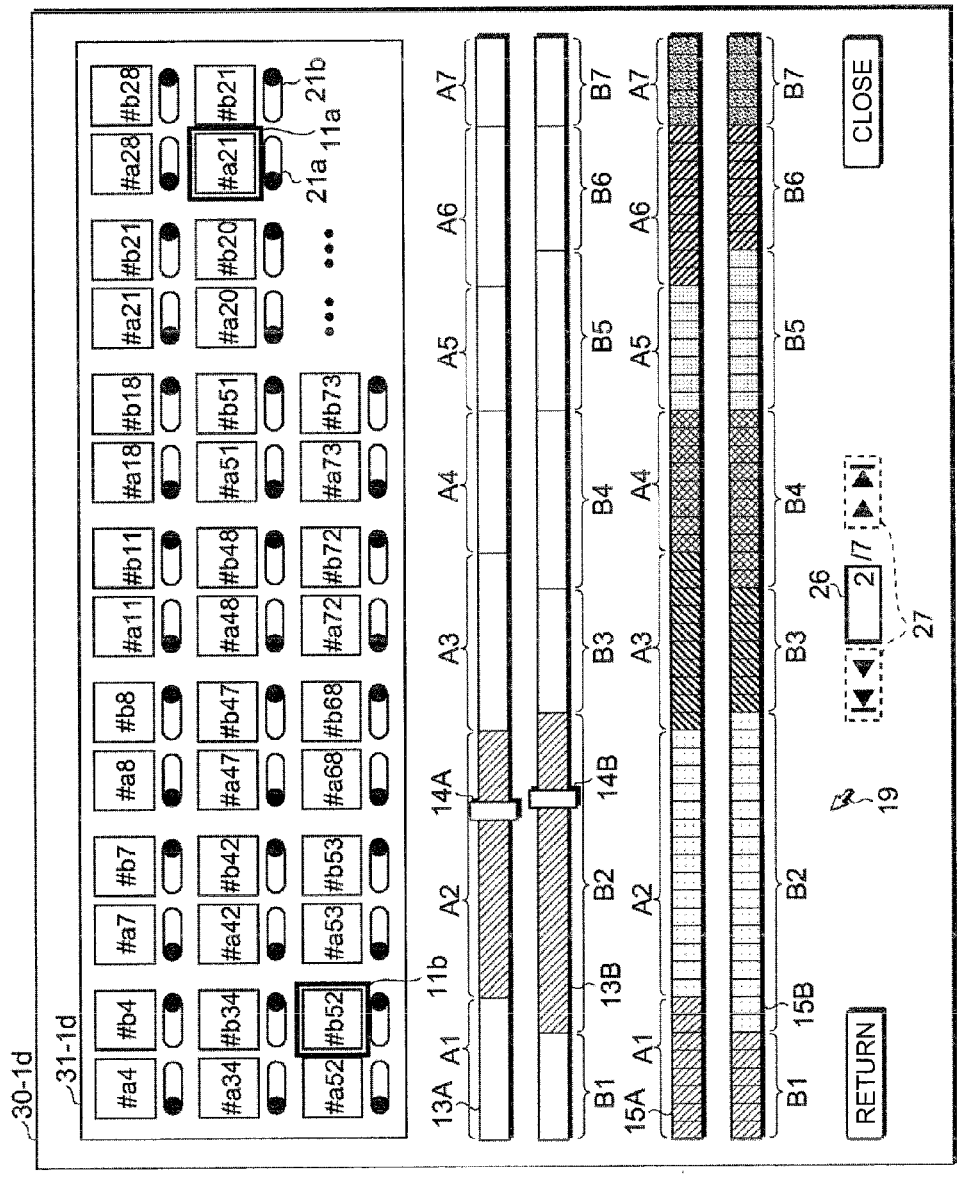
FIG. 53 is a diagram showing an example of an overview screen according to modification 3-1d of the third embodiment of the invention.

With the configuration and operation as described above, in the modification 3-1d, an overview screen 30-1d as shown in FIG. 53 is generated and displayed. FIG. 53 shows an example of the overview screen 30-1d according to the modification 3-1d.

As shown in FIG. 53, in the overview image display region 31-1d in the overview screen 30-1d, so-called logical product (AND) is obtained between selected image data having the camera ID=1 and selected image data having the camera ID=2 and reduced images of the matching image data are paired and displayed.

As described above, in the modification 3-1d, the image data of the same position, obtained by different eyes is arranged side by side and a list of the image data can be displayed. Thus, the observer can easily observe a region in the subject 900 from a plurality of angles.

Modification 3-2

Figure 54:
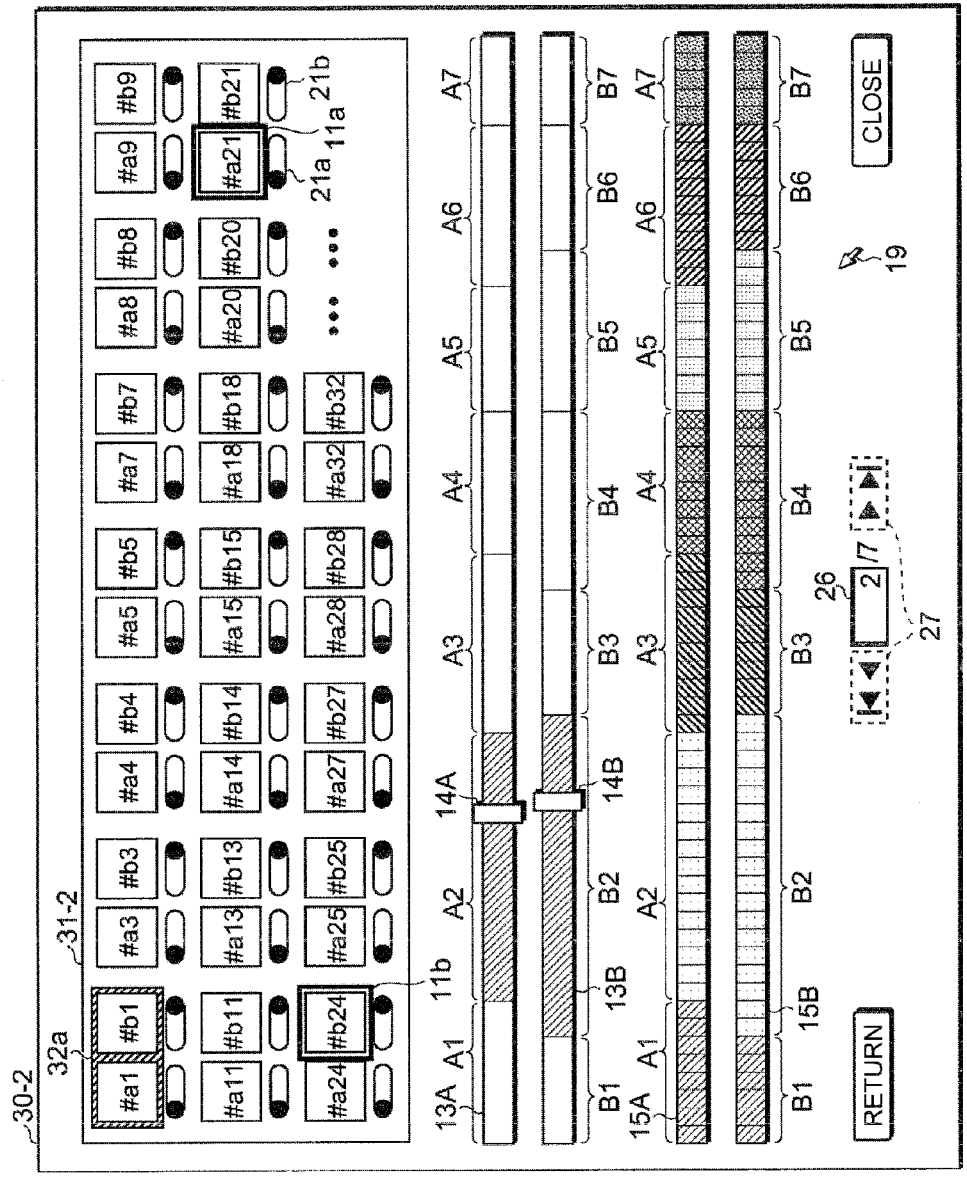
FIG. 54 is a diagram showing an example of an overview screen before synchronization according to modification 3-2 of the third embodiment of the invention.

Image data having different camera IDs may be paired by, for example, a method described in the modification 1-8 of the first embodiment. In this case, as shown in an overview image display region 31-2 in an overview screen 30-2 according to modification 3-2 of the embodiment shown in FIG. 54, a synchronization start frame 32a for emphatically displaying a pair of reduced images of image data as a start point (in the example of FIG. 54, image data #a1 and #b1) may be added to the pair. FIG. 54 is a diagram showing an example of the overview screen 30-2 before synchronization of the modification 3-2.

Since such emphatic display process can be easily realized by the screen generating unit 354f in the image processing unit 354 in FIG. 42, the detailed description will not be given.

Modification 3-3

Figure 55:
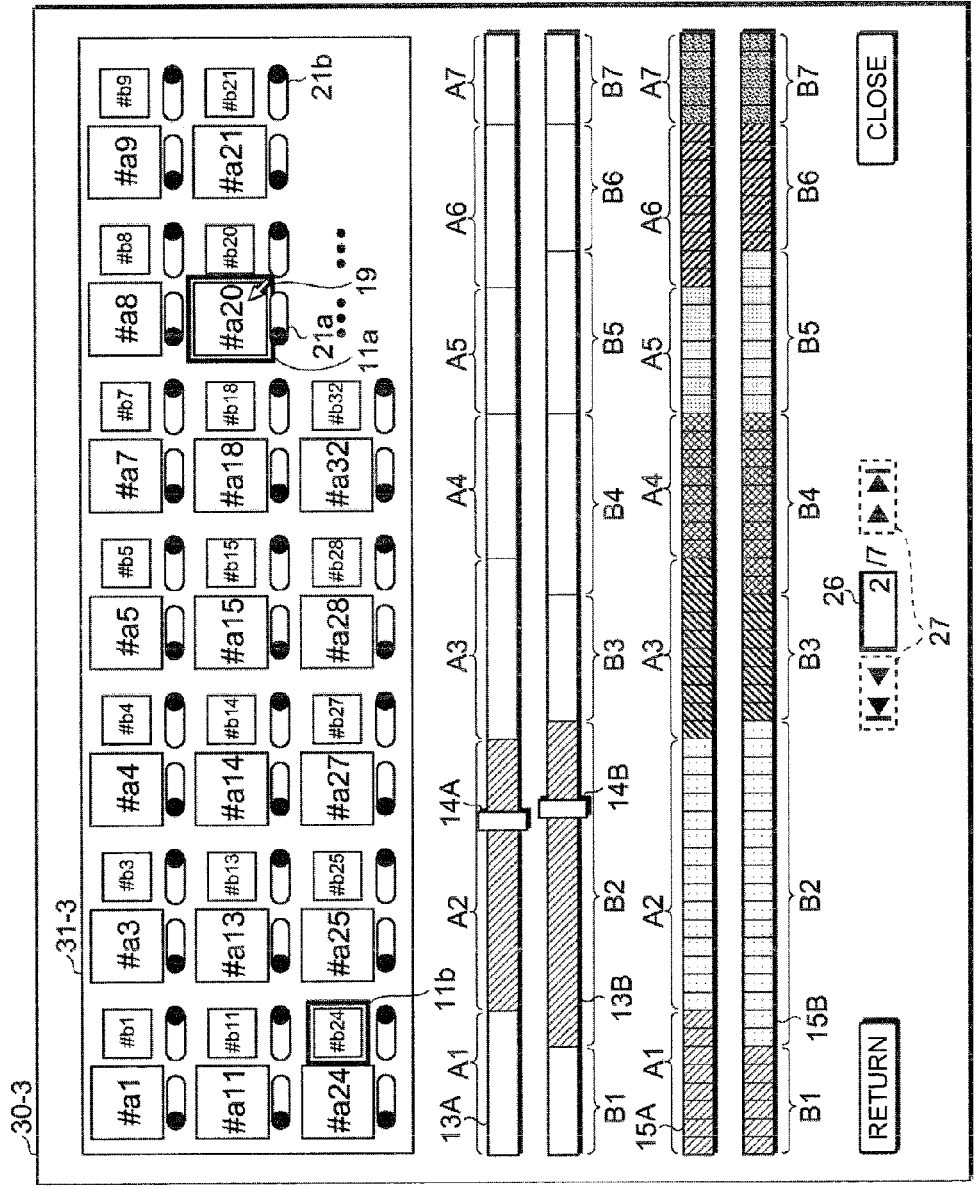
FIG. 55 is a diagram showing an example of an overview screen before synchronization according to modification 3-3 of the third embodiment of the invention.

In reduced images of image data having different camera IDs, a reduced image of image data having a noted camera ID (in the description, camera ID=1) may be displayed larger than that of image data having the other camera ID (in the description, camera ID=2) as shown in an overview screen 30-3 according to modification 3-3 of the embodiment shown in FIG. 55. FIG. 55 is a diagram showing an example of the overview screen 30-3 before synchronization of the modification 3-3.

The observer clicks any of noted reduced images in reduced images displayed in the overview image display region 31-3 of the overview screen 30-3 by using the mouse or the like of the input unit 156. For example, the observer clicks any of the reduced images (#a1, . . . ) generated from the image data having the camera ID=1. In the overview image display region 31-3, as shown in FIG. 55, a reduced image generated from the image data (#a1, . . . ) having the camera ID=1 is displayed larger than a reduced image generated from the image data (#b1, . . . ) having the camera ID=2.

Since such an enlarging process can be easily realized by the screen generating unit 354f in the image processing unit 354 in FIG. 42, the detailed description will not be given.

Modification 3-4

Figure 56:
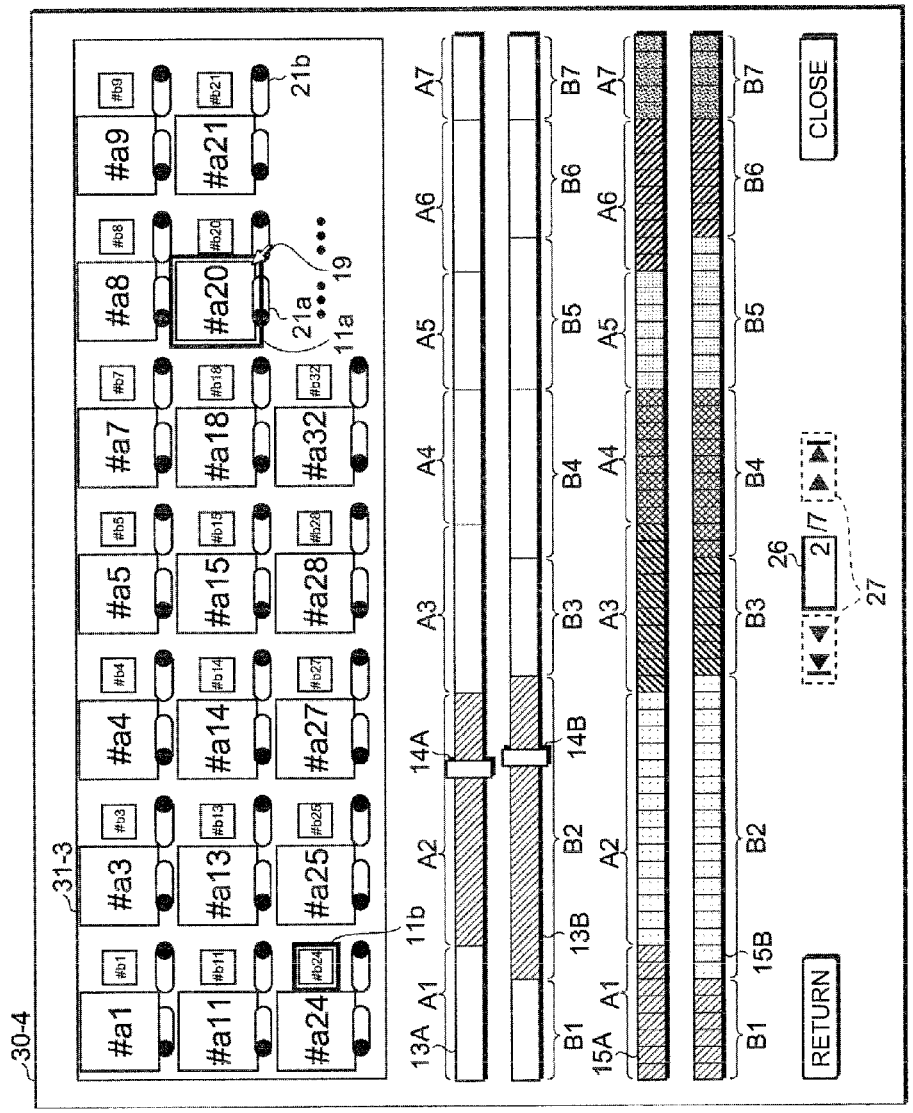
FIG. 56 is a diagram showing an example of an overview screen before synchronization according to modification 3-4 of the third embodiment of the invention.

Preferably, the size at the time of enlarging a reduced image of image data having a noted camera ID (in the description, camera ID=1) can be arbitrary set by the observer using the mouse or the like of the input unit 156 as shown in an overview image display region 31-3 in an overview screen 30-4 according to modification 3-4 of the embodiment shown in FIG. 56. FIG. 56 is a diagram showing an example of the overview screen 30-4 before synchronization of the modification 3-4.

Since such an enlarging process can be easily realized by the screen generating unit 354f in the image processing unit 354 in FIG. 42, the detailed description will not be given.

Although image data having different camera IDs are paired by the image generating unit 354f in the third embodiment and its modifications, the form of displaying a group of image data pieces obtained as a result of the process is not limited to the overview screen.

Concretely, different display regions may be provided for the imaging units on the display screen of the display unit 155, and only a group of image data pieces pared by the image generating unit 354f may be sequentially displayed in the display regions corresponding to the imaging units. The display screen is called a sequential display screen.

The control unit 151 of the display device 350 may have the function of controlling the overview screen and the sequential display screen to be switched. With the function, it becomes possible to make the observer confirm only the image data group subjected to the pairing process by the image generating unit 354f. As a result, the observer can observe the inside of the subject easily and efficiently.

Fourth Embodiment

Reduced images of image data can be also displayed in time series in a single overview image display region irrespective of imaging units. In the following, the case will be described in detail as a fourth embodiment of the invention with reference to the drawings.

A medical system according to the fourth embodiment may have a configuration similar to that of the medical system 1 according to the first embodiment. In the fourth embodiment, the display device 150 is replaced with a display device 450 shown in FIG. 57. In the following description, the same reference numerals are designated to components similar to those of the foregoing first, second, and third embodiments and their modifications, and repetitive description will not be given.

Figure 57:
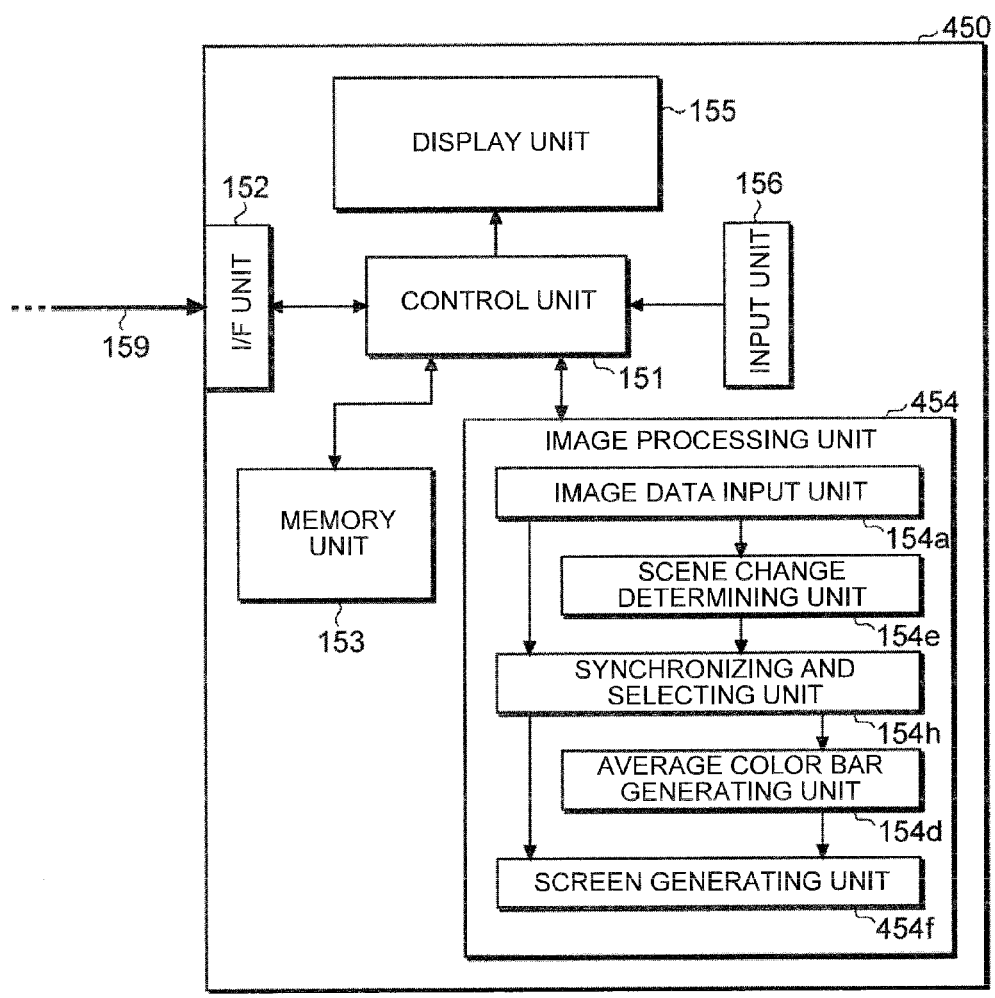
FIG. 57 is a block diagram showing an example of a schematic configuration of a display device according to a fourth embodiment of the invention.

FIG. 57 is a block diagram showing a schematic configuration example of the display device 450 according to the fourth embodiment. As illustrated in FIG. 57, in the display device 450, the image processing unit 154 shown in FIG. 4 is replaced with an image processing unit 454. The image processing unit 454 has a configuration similar to that of the image processing unit 150-2b (refer to FIG. 17) in the modification 1-2b except that the screen generating unit 154f is replaced with a screen generating unit 454f.

Figure 58:
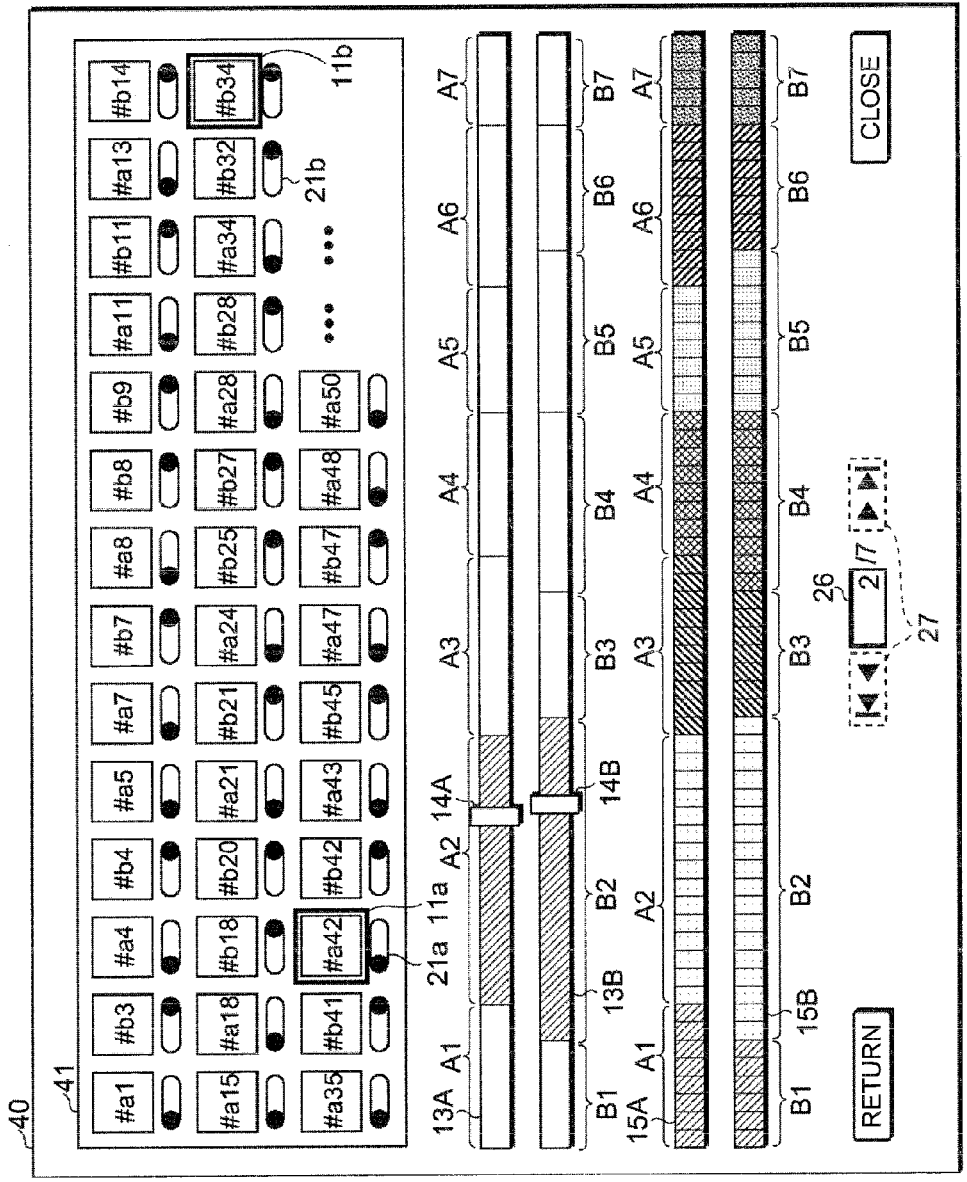
FIG. 58 is a diagram showing an example of an overview screen according to the fourth embodiment of the invention.

The screen generating unit 454f generates an overview screen 40 as shown in FIG. 58 by using image data output and selected by the synchronizing and selecting unit 154h and the images of the average color bars 15A and 15B output from the average color bar generating unit 154d. FIG. 58 shows an example of the overview screen 40 according to the fourth embodiment.

As shown in FIG. 58, the overview screen 40 according to the fourth embodiment includes an overview image display region 41 displaying a list of reduced images of selected image data, the time scale bar 13A, the slider 14A, and the average color bar 15A on image data having the camera ID=1, the time scale bar 13B, the slider 14B, and the average color bar 15B on image data having the camera ID=2, the display scene box 26 indicative of the order of a scene being displayed in the overview image display region 41 in all of scenes, and the scene switching button 27 for switching the scene to be displayed in the overview image display region 41.

In the overview image display region 41, reduced images of selected image data having the camera ID=1 and reduced images of selected image data having the camera ID=2 are arranged in a list along time series. Near (for example, below) each reduced image, an image (hereinbelow, called capsule image) 21*a*/21*b* visually showing, to the observer, the imaging unit (101A or 101B) of the capsule medical device 100 which captured the reduced image may be displayed.

Figure 59:
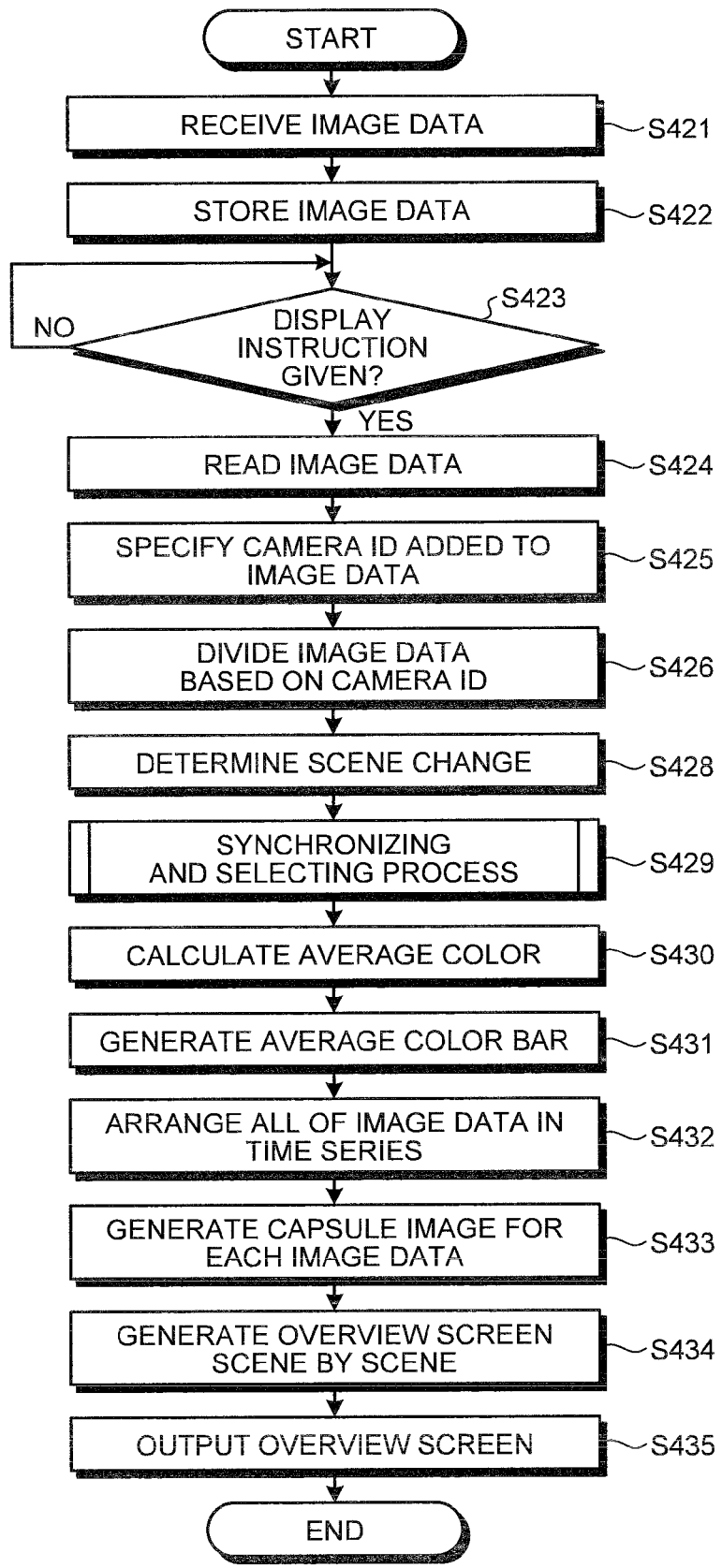
FIG. 59 is a flowchart showing an example of outline operation of the display device according to the fourth embodiment of the invention.

The operation of the medical system according to the fourth embodiment will now be described in detail with reference to the drawings. Since the operation of the capsule medical device 100 and that of the receiving device 130 in the fourth embodiment are similar to those of the first embodiment (refer to FIGS. 6 and 7), the detailed description will not be repeated. FIG. 59 is a flowchart showing an example of schematic operation of the display device 450 according to the fourth embodiment.

As shown in FIG. 59, the display device 450 according to the fourth embodiment receives image data from the interface unit 152 using the portable recording medium 140 or the communication cable 159 as a medium (step S421) and temporarily stores the image data in the memory unit 153 or the like via the control unit 151 (step S422).

Next, the display device 450 waits until a display instruction of the overview screen 40 is supplied from the input unit 156 or the like (No at step S423). In the case where a display instruction is received (Yes at step S423), the display device 450 reads image data stored in the memory unit 153 or the like (step S424). The read image data is supplied to the image data input unit 154*a* in the image processing unit 454.

The image data input unit 154*a* specifies each of the camera IDs added to the input image data (step S425) and divides the image data by imaging units (101A and 101B) on the basis of the camera IDs, that is, by camera IDs (step S426). The divided image data is supplied to the scene change determining unit 154*e*.

The scene change determining unit 154*e* determines image data in which a scene change occurs on the basis of a result of image process on successive image data by camera IDs (step S428). The scene change determination result is supplied to the synchronizing and selecting unit 154*h*.

On the basis of the scene change determination result supplied from the scene change determining unit 154*e*, the synchronizing and selecting unit 154*h* executes a synchronizing and selecting process of selecting image data while synchronizing it (step S429). As the synchronizing and selecting process according to the embodiment, a process similar to the synchronizing and selecting process in the modifications 1-2a to 1-2d of the first embodiment (refer to step S130-2*b* in FIG. 18 and FIG. 19, 22, or 24) can be used. Image data selected in step S429 is supplied to the average color bar generating unit 154*d* and the screen generating unit 454*f*.

The average color bar generating unit 154*d* to which the selected image data is supplied selects the image data by camera IDs and calculates an average color of the image data (or by regions obtained by dividing the image data) (step S430). On the basis of the calculation result, the average color bar generating unit 154*d* generates the average color bars 15A and 15B by connecting images of the calculated average colors in time series (step S431). The generated average color bars 15A and 15B are supplied to the screen generating unit 454*f*.

The screen generating unit 454*f* to which the images of the average color bars 15A and 15B and the selected image data is input arranges the selected image data in time series without discriminating the image data having the camera ID=1 and the image data having the camera ID=2 from each other (step S432), generates the capsule image 21*a* on the basis of the camera ID for each of the image data supplied and selected (step S433), generates the overview screen 40 scene by scene as shown in FIG. 58 by using the images of the average color bars 15A and 15B (step S434), outputs the overview screen 40 generated to the display unit 155 (step S435) and, after that, finishes the operation. As a result, the overview screen 40 as the GUI screen is displayed in the display unit 155, and the GUI function using it is provided to the observer.

As described above, in the fourth embodiment, image data obtained by performing the imaging operation with different eyes can be arranged side by side and displayed in a list. Therefore, the observer can easily observe a region in the subject 900 from a plurality of angles.

The foregoing embodiments are just examples for carrying out the present invention, and the present invention is not limited to the embodiments and various modifications according to specifications and the like are within the scope of the present invention. It is obviously understood from the above description that other various embodiments are possible within the scope of the present invention. For example, the average color bars 15A and 15B may be generated from all of image data obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing system comprising:
 a body-insertable apparatus that includes
  two imaging units that capture inside of a subject to generate image data,
  an identification information adding unit that adds identification information for identifying an imaging unit that generates image data to the image data, and
  an output unit that outputs the image data to which the identification information is added to the outside; and
 an external device that includes
  an input unit that receives the image data,
  a selecting unit that selects image data to be displayed on the basis of a degree of similarity between successive image data, the degree of similarity being calculated from feature points of the image data in a series of image data pieces to which one identification information is added, and selects image data to be displayed on the basis of a degree of similarity between successive image data, the degree of similarity being calculated from feature points of the image data in a series of image data pieces to which the other identification information is added, to synchronize image data to which the one identification information is added with image data to which the other identification information is added, the image data to which the other identification information is added being obtained by capturing a same specific region of the inside of the subject as that corresponding to the image data to which the one identification information is added,
  a synchronizing unit that synchronizes the image data of the one identification information selected by the selecting unit with image data of the other identification information, wherein an imaging time at which the same specific region of the inside of the subject is captured to obtain the image data of the other identification information is in a predetermined time range from an imaging time at which the same specific region is captured to obtain the image data of the one identification information,
a list displaying unit that displays a list of the selected image data synchronized by the synchronizing unit, by the identification information, and
a switching unit that switches image data to be displayed by the list displaying unit from image data of the identification information being displayed to image data of the other identification information synchronized by the synchronizing unit,
wherein in the case where the image data of the other identification information synchronized with the image data of the one identification information by the synchronizing unit is not selected from the series of image data pieces of the other identification information, the selecting unit further selects, as image data to be displayed, image data synchronized with image data of the one identification information in the series of image data pieces of the other identification information which was not selected.

2. The image processing system according to claim 1, wherein the body-insertable apparatus includes an imaging time adding unit that adds imaging time to each image data to which identification information is added, and
the synchronizing unit synchronizes image data of the one identification information and image data of the other identification information by adding/subtracting predetermined time to/from imaging time added to the image data of the one identification information out of the image data.

3. The image processing system according to claim 1, wherein the list displaying unit displays, in different screens, a first list display region for displaying a list of the image data of the one identification information and a second list display region for displaying a list of the image data of the other identification information.

4. The image processing system according to claim 1, wherein in the case where the image data of the other identification information synchronized with the image data of the one identification information is not selected as image data to be displayed, the synchronizing unit generates null image data of the other identification information to be synchronized with the image data of the one identification information.

5. The image processing system according to claim 1, wherein the external device includes a start image selecting unit that selects image data as a start point of the synchronization, and
the synchronizing unit synchronizes image data of the one identification information and image data of the other identification information using, as a start point, image data selected by the start image selecting unit.

6. The image processing system according to claim 1, wherein the external device includes
a turn instruction input unit that inputs an instruction to turn image data displayed in a list; and
a turn correcting unit that corrects the image data to which the turn instruction is input, and
the list displaying unit displays the image data subjected to the turn correction, included in the list.

7. The image processing system according to claim 1, wherein the list displaying unit displays a screen including a list display region for displaying a list of image data by the identification information, and image data which cannot be displayed at a time in the list display region is displayed in a list display region in the next page.

8. The image processing system according to claim 1, wherein the list displaying unit displays a list of reduced images of the image data.

9. An external device comprising:
an input unit that receives image data from a body-insertable apparatus, the body-insertable apparatus including two imaging units that capture an image of inside of a subject to generate image data, and an identification information adding unit that adds identification information for identifying an imaging unit that generates the image data to the image data;
a selecting unit that selects image data to be displayed on the basis of a degree of similarity between successive image data, the degree of similarity being calculated from feature points of the image data in a series of image data pieces to which one identification information is added, and selects image data to be displayed on the basis of a degree of similarity between successive image data, the degree of similarity being calculated from feature points of the image data in a series of image data pieces to which the other identification information is added, to synchronize image data to which the one identification information is added with image data to which the other identification information is added, the image data to which the other identification information is added being obtained by capturing a same specific region of the inside of the subject as that corresponding to the image data to which the one identification information is added;
a synchronizing unit that synchronizes the image data of the one identification information selected by the selecting unit with image data of the other identification information, wherein an imaging time at which the same specific region of the inside of the subject is captured to obtain the image data of the other identification information is in a predetermined time range from an imaging time at which the same specific region is captured to obtain the image data of the one identification information;
a list displaying unit that displays a list of the image data synchronized by the synchronizing unit, by the identification information; and
a switching unit that switches image data to be displayed by the list displaying unit from image data of the identification information being displayed to image data of the other identification information synchronized by the synchronizing unit,
wherein in the case where the image data of the other identification information synchronized with the image data of the one identification information by the synchronizing unit is not selected from the series of image data pieces of the other identification information, the selecting unit further selects, as image data to be displayed, image data synchronized with image data of the one identification information in the series of image data pieces of the other identification information which was not selected.

10. An image processing method comprising:
receiving image data from a body-insertable apparatus that includes a plurality of imaging means for capturing an image of inside of a subject to generate image data and an identification information adding means for adding identification information for identifying an imaging means that generates the image data to the image data;

selecting image data to be displayed on the basis of a degree of similarity between successive image data, the degree of similarity being calculated from feature points of the image data in a series of image data pieces to which one identification information is added, and selecting image data to be displayed on the basis of a degree of similarity between successive image data, the degree of similarity being calculated from feature points of the image data in a series of image data pieces to which the other identification information is added, to synchronize image data to which the one identification information is added with image data to which the other identification information is added, the image data to which the other identification information is added being obtained by capturing a same specific region of the inside of the subject as that corresponding to the image data to which the one identification information is added;

synchronizing the image data of the one identification information selected by the selecting unit with image data of the other identification information, wherein an imaging time at which the same specific region of the inside of the subject is captured to obtain the image data of the other identification information is in a predetermined time range from an imaging time at which the same specific region is captured to obtain the image data of the one identification information;

displaying a list of the synchronized image data by the identification information; and switching image data to be displayed in the list from image data of the one identification information being displayed to image data of the other identification information, wherein the selecting further includes selecting as image data to be displayed, in the case where the image data of the other identification information synchronized with the image data of the one identification information at the synchronizing is not selected from the series of image data pieces of the other identification information, image data synchronized with image data of the one identification information in the series of image data pieces of the other identification information which was not selected.

11. An image processing system comprising:
a body-insertable apparatus that includes
two imaging units that capture inside of a subject to generate image data,
an identification information adding unit that adds identification information for identifying an imaging unit that generates image data to the image data, and
an output unit that outputs the image data to which the identification information is added to the outside; and
an external device that includes
an input unit that receives the image data,
a selecting unit that selects image data to be displayed on the basis of a degree of similarity between successive image data, the degree of similarity being calculated from feature points of the image data in a series of image data pieces to which one identification information is added, and selects image data to be displayed on the basis of a degree of similarity between successive image data, the degree of similarity being calculated from feature points of the image data in a series of image data pieces to which the other identification information is added, to synchronize image data to which the one identification information is added with image data to which the other identification information is added, the image data to which the other identification information is added being obtained by capturing a same specific region of the inside of the subject as that corresponding to the image data to which the one identification information is added, a synchronizing unit that synchronizes the image data of the one identification information selected by the selecting unit with image data of the other identification information, wherein an imaging time at which the same specific region of the inside of the subject is captured to obtain the image data of the other identification information is in a predetermined time range from an imaging time at which the same specific region is captured to obtain the image data of the one identification information, a list displaying unit that displays a list of the image data synchronized by the synchronizing unit, by the identification information, and a switching unit that switches image data to be displayed by the list displaying unit from image data of the identification information being displayed to image data of the other identification information synchronized by the synchronizing unit, wherein in the case where the image data of the other identification information synchronized with the image data of the one identification information is not selected, the synchronizing unit excludes the image data of the one identification information from image data to be displayed.

12. The image processing system according to claim 11, wherein the body-insertable apparatus includes an imaging time adding unit that adds imaging time to each image data to which identification information is added, and
the synchronizing unit synchronizes image data of the one identification information and image data of the other identification information by adding/subtracting predetermined time to/from imaging time added to the image data of the one identification information out of the image data.

13. The image processing system according to claim 11, wherein the list displaying unit displays, in different screens, a first list display region for displaying a list of the image data of the one identification information and a second list display region for displaying a list of the image data of the other identification information.

14. The image processing system according to claim 11, wherein in the case where the image data of the other identification information synchronized with the image data of the one identification information is not selected as image data to be displayed, the synchronizing unit generates null image data of the other identification information to be synchronized with the image data of the one identification information.

15. The image processing system according to claim 11, wherein the external device includes a start image selecting unit that selects image data as a start point of the synchronization, and
the synchronizing unit synchronizes image data of the one identification information and image data of the other identification information using, as a start point, image data selected by the start image selecting unit.

16. The image processing system according to claim 11, wherein the external device includes
a turn instruction input unit that inputs an instruction to turn image data displayed in a list; and a turn correcting unit that corrects the image data to which the turn instruction is input, and the list displaying unit displays the image data subjected to the turn correction, included in the list.

17. The image processing system according to claim 11, wherein the list displaying unit displays a screen including a list display region for displaying a list of image data by the identification information, and image data which cannot be displayed at a time in the list display region is displayed in a list display region in the next page.

18. The image processing system according to claim 11, wherein the list displaying unit displays a list of reduced images of the image data.

19. An image processing system comprising:

a body-insertable apparatus that includes two imaging units that capture inside of a subject to generate image data, an identification information adding unit that adds identification information for identifying an imaging unit that generates image data to the image data, and an output unit that outputs the image data to which the identification information is added to the outside; and an external device that includes an input unit that receives the image data, a selecting unit that selects image data to be displayed on the basis of a degree of similarity between successive image data, the degree of similarity being calculated from feature points of the image data in a series of image data pieces to which one identification information is added, and selects image data to be displayed on the basis of a degree of similarity between successive image data, the degree of similarity being calculated from feature points of the image data in a series of image data pieces to which the other identification information is added, to synchronize image data to which the one identification information is added with image data to which the other identification information is added, the image data to which the other identification information is added being obtained by capturing a same specific region of the inside of the subject as that corresponding to the image data to which the one identification information is added, a synchronizing unit that synchronizes the image data of the one identification information selected by the selecting unit with image data of the other identification information, wherein an imaging time at which the same specific region of the inside of the subject is captured to obtain the image data of the other identification information is in a predetermined time range from an imaging time at which the same specific region is captured to obtain the image data of the one identification information, a determining unit that determines a definition on the basis of a specific pattern or an edge of each region included in the image data of the one identification information, a list displaying unit that displays a list of the image data synchronized by the synchronizing unit, by the identification information, and a switching unit that switches image data to be displayed by the list displaying unit from image data of the identification information being displayed to image data of the other identification information synchronized by the synchronizing unit, wherein the switching unit individually switches a plurality of image data pieces to be displayed as a list, and in the case where the determining unit determines that the image data of the one identification information is unclear, the switching unit switches the image data to the image data of the other identification information synchronized with the image data of the one identification information.

20. The image processing system according to claim 19, wherein the body-insertable apparatus includes an imaging time adding unit that adds imaging time to each image data to which identification information is added, and the synchronizing unit synchronizes image data of the one identification information and image data of the other identification information by adding/subtracting predetermined time to/from imaging time added to the image data of the one identification information out of the image data.

21. The image processing system according to claim 19, wherein the list displaying unit displays, in different screens, a first list display region for displaying a list of the image data of the one identification information and a second list display region for displaying a list of the image data of the other identification information.

22. The image processing system according to claim 19, wherein in the case where the image data of the other identification information synchronized with the image data of the one identification information is not selected as image data to be displayed, the synchronizing unit generates null image data of the other identification information to be synchronized with the image data of the one identification information.

23. The image processing system according to claim 19, wherein the external device includes a start image selecting unit that selects image data as a start point of the synchronization, and the synchronizing unit synchronizes image data of the one identification information and image data of the other identification information using, as a start point, image data selected by the start image selecting unit.

24. The image processing system according to claim 19, wherein the list displaying unit displays, near image data, an image of making an imaging unit that obtains the image data displayed in a list visually identified.

25. The image processing system according to claim 19, wherein the external device includes a turn instruction input unit that inputs an instruction to turn image data displayed in a list; and a turn correcting unit that corrects the image data to which the turn instruction is input, and the list displaying unit displays the image data subjected to the turn correction, included in the list.

26. The image processing system according to claim 19, wherein the list displaying unit displays a screen including a list display region for displaying a list of image data by the identification information, and image data which cannot be displayed at a time in the list display region is displayed in a list display region in the next page.

27. The image processing system according to claim 19, wherein the list displaying unit displays a list of reduced images of the image data.

* * * * *